United States Patent [19]
Ando et al.

[11] Patent Number: 5,416,117
[45] Date of Patent: * May 16, 1995

[54] CYCLOPROPENONE DERIVATIVES

[75] Inventors: Ryoichi Ando, Machida; Yasuhiro Morinaka, Tsuchiura; Chizuko Takahashi, Yokohama; Yoshikuni Tamao, Machida; Akihiro Tobe, Yokohama, all of Japan

[73] Assignee: Mitsubishi Kasei Corporation, Japan

[*] Notice: The portion of the term of this patent subsequent to Jul. 12, 2011 has been disclaimed.

[21] Appl. No.: 202,555

[22] Filed: Feb. 28, 1994

Related U.S. Application Data

[62] Division of Ser. No. 905,544, Jun. 25, 1992, Pat. No. 5,328,909.

[30] Foreign Application Priority Data

| Jun. 25, 1991 | [JP] | Japan | 3-153500 |
| Oct. 24, 1991 | [JP] | Japan | 3-277904 |
| Dec. 24, 1991 | [JP] | Japan | 3-341497 |
| Jun. 5, 1992 | [JP] | Japan | 4-146024 |

[51] Int. Cl.[6] .................. A61K 31/165; A61K 31/18; C07C 237/20; C07C 311/18
[52] U.S. Cl. .................................... 514/604; 514/256; 514/300; 514/311; 514/330; 514/331; 514/354; 514/355; 514/356; 514/406; 514/427; 514/436; 514/443; 514/469; 514/471; 514/487; 514/489; 514/531; 514/568; 514/580; 514/601; 514/605; 514/616; 514/619; 514/626; 544/316; 544/335; 546/122; 546/168; 546/169; 546/170; 546/173; 546/234; 546/235; 546/261; 546/262; 546/263; 546/265; 548/333.5; 548/374.1; 548/561; 549/58; 549/77; 549/467; 549/496; 560/39; 560/41; 560/125; 562/448; 562/450; 562/506; 564/46; 564/59; 564/91; 564/152; 564/155; 564/164; 564/168
[58] Field of Search ........................... 564/91; 514/604

[56] References Cited

U.S. PATENT DOCUMENTS 5,055,451 10/1991 Krantz et al. ................... 514/19

FOREIGN PATENT DOCUMENTS

| 0196189 | 10/1986 | European Pat. Off. |
| 0272671 | 6/1988 | European Pat. Off. |
| 0393457 | 10/1990 | European Pat. Off. |
| 0410411 | 1/1991 | European Pat. Off. |
| 294176 | 9/1991 | German Dem. Rep. |
| 58-126879 | 7/1983 | Japan |
| 63-253061 | 10/1988 | Japan |
| 2-218610 | 8/1990 | Japan |
| 2227411 | 8/1990 | United Kingdom |

OTHER PUBLICATIONS

Taisha (Metabolism), 25, an extra number "Taisha-byo Hilight", 183 (1988).
Journal of Pharmacobio dynamics, 10, 678, (1987).
New England Journal of Medicine, 312, p. 159, (1985).
Saishin Igaku, 43, p. 783, (1988).
Arzneimittel Forschung/Drug Research, 36, p. 190, p. 671, (1986).
Brain Research, 526, p. 177, (1990).
Scientific American, (11), p. 40, (1991).
Neurochemical Research, 16, p. 483, (1991).
Journal of Neurosurgery, 65, p. 92, (1986).
Journal of Neurochemistry, 47, p. 1007, (1986).
Investigative Ophthalmology & Visual Science, 28, p. 1702, (1987).

(List continued on next page.)

Primary Examiner—Peter O'Sullivan
Attorney, Agent, or Firm—Wenderoth, Lind & Ponack

[57] ABSTRACT

A novel cyclopropenone derivative (I) which possesses a potent inhibitory activity against thiol protease such as papain, cathepsin B, cathepsin H, cathepsin L, calpain or the like with excellent properties regarding oral absorbance, tissue transference and cell membrane permeability, and are clinically useful in the treatment of various diseases such as muscular dystrophy, amyotrophy. Also provided are a process for producing the compound (I) and a pharmaceutical composition containing the same.

2 Claims, No Drawings

OTHER PUBLICATIONS

Experimental Eye Research, 34, p. 413, (1982).
Lens and Eye Toxicity Research, 6, p. 725, (1989).
Investigative Ophthalmology & Visual Science, 32, p. 533, (1991).
Journal of Biological Chemistry, 263, p. 1915, (1988).
Journal of Biochemistry, 98, p. 87, (1985).
The Journal of Antibiotics, 42, p. 1362, (1989).
Biochemical and Biophysical Research Communication, 125, p. 441, (1981).
Tumor Progression and Markers, p. 47, (1982).
Journal of Biological Chemistry, 256, p. 8536, (1984).
Thrombosis Research, 57, p. 847, (1990).
Agricultural and Biological Chemistry, 42, p. 529, (1978).
Journal of Biochemistry, 93, p. 1305, (1983).
Journal of Biochemistry, 99, p. 173, (1986).
Biochemistry, 30, p. 4678, (1991).
The Journal of Antibiotics, 22, p. 283, (1969).
Journal of Enzyme Inhibition, 3, p. 195, (1990).
Tetrahedron Letters, vol. 32, No. 10, Mar. 4, 1991, pp. 1339–1342.
Krantz et al., *Biochemistry*, 30(19), 4678–4687 (1991).
Smith et al., *J. Am. Chem. Soc.*, 110(13), 4429–4431 (1988).
Zumbrunn et al., *Biochem. J.*, 256, 989–994 (1988).
Shaw et al., *The Journal of Biological Chemistry*, 263(6), 2678–2772 (1988).
Rauber et al., *Biochem. J.*, 250, 871–876 (1988).
WPI Acc. No. 92-034226/05 (EP 468469), (Jul. 27, 1990).
WPI Acc. No. 92-065587/09 (DD 294176), (May 11, 1990).

CYCLOPROPENONE DERIVATIVES

This is a divisional application of Ser. No. 07/905,544, filed Jun. 25, 1992, now U.S. Pat. No. 5,326,909.

FIELD OF THE INVENTION

The present invention relates to novel cyclopropenone derivatives. More particularly, this invention relates to novel cyclopropenone derivatives having a potent inhibitory activity against thiol protease such as papain, cathepsin B, cathepsin H, cathepsin L, calpain or the like.

BACKGROUND OF THE INVENTION

In accordance with the elucidation of the in vivo activity of thiol protease such as papain, cathepsin B, cathepsin H, cathepsin L, calpain or the like, it has been found that their extraordinary hypersthenia causes various diseases. Further, there is increasing the report which shows thiol protease inhibitors are effective on such disease in animal models.

It is considered that thiol protease such as calpain, cathepsin B or the like take part in the initial process such as disappearance of Z line through the decomposition of muscular fiber protein in the collapse of skeletal muscle as seen in muscular disease such as muscular Dystrophy, amyotrophy or the like [Taisha (Metabolism), 25, 183 (1988)]. Furthermore, E-64-d, namely a thiol protease inhibitor, has been reported to have life-prolonging effect in experimental muscular dystrophy hamster [Journal of Pharmacobio dynamics, 10, 678 (1987)]. Accordingly, such thiol protease inhibitors are expected to be useful as therapeutic agents for the treatment of muscular dystrophy, amyotrophy or the like.

The main cause of the post-ischemic cellular disorder occurs during ischemic diseases such as cardiac infarction, stroke and the like is active oxygen produced by xanthine oxidase. It has been reported that, during the ischemia, the increase in $Ca^{2+}$ concentration results in the activation of calpain which restrictively degrade xanthine dehydrogenase, a precursor of xanthine oxidase, to give xanthine oxidase [New England Journal of Medicine, 312, p.159, (1985)]. It has also been reported that the activation of calpain may directly cause the necrosis of myocardial cells or neurocytes [Saishin Igaku, 43, p.783, (1988)]. There have been reported that NCO-700, a calpain inhibitor, is effective on cardiac infarction when tested on animal models [Arzneimittel Forschung/Drug Research, 36, p.190, p.671, (1986)], and that E-64-C inhibits the degradation of microtubule-associated protein after the brain ischemia [Brain Research, 526, p.177, (1990)]. These reports indicate that a calpain inhibitor can be useful for the treatment of ischemic diseases such as cardiac infarction, stroke and the like.

The cause of senile plaque which is found specifically in the brain of patients suffering from Alzheimer's disease is known to be the precipitated amyloid, a protein produced by the decomposition of an amyloid precursor protein (APP). Although APP does not give amyloid as a normal metabolite, it may be converted into amyloid under an abnormal metabolism where protease is extremely activated, and precipitated as senile plaque [Scientific American, (11), p.40, (1991)]. Therefore, protease inhibitor is expected to be useful for the treatment of Alzheimer's disease.

The activation of calpain has been observed in a brain trauma model of rabbit [Neurochemical Research, 16, p.483, (1991)]. It has also been observed, the administration of leupetin, a calpain inhibitor, can protect axon in brain trauma models of rat [Journal of Neurosurgery, 65, p.92, (1986)]. Thus, calpain inhibitors are considered to be useful for improving the conscious disturbance or motor disturbance caused by brain trauma.

It has also been reported that myelin-associated protein exists in dendrite of neurocytes is decomposed by calpain [Journal of Neurochemistry, 47, p.1007, (1986)], indicating that calpain inhibitors may be effective on diseases caused by the demyelination of neurocytes such as multiple sclerosis, peripheral nervous neuropathy and the like.

The main cause of the turbidity during cataract is hydrolytic products of a water-soluble protein crystallin by protease in lens. It has been observed the increase in calcium concentration in lens of cataractous animal models and some of human cataract [Investigative Ophthalmology & Visual Science, 28, p.1702, (1987); Experimental Eye Research, 34, p.413, (1982)]. The dominant protease contained in lens is calpain [Lens and Eye Toxicity Research, 6, p.725, (1989)]. These facts indicate that the abnormal sthenia of calpain can be one of the causes of cataract. There is a report that E-64, an inhibitor of calpain, is effective on cataract in animal models [Investigative Ophthalmology & Visual Science, 32, p.533, (1991)], indicating that calpain inhibitors can be useful in the treatment of cataract.

Neutrophils, which is deeply associated to inflammation, show the degranulation or production of superoxides in response to the stimulations by a chemotaxic factor or phorbol ester through a mechanism appeared to be mediated by protein kinase C (PKC). Calpain participates in the activation of PKC in the manner where it promotes the degranulation and inhibits the production of superoxides [Journal of Biological Chemistry, 263, p.1915, (1988)]. In another report, the concentration of cathepsin B in macrophage in rat is 30 to 40 times that of leukocytes and neutrophils, and the concentration of the enzyme in inflammatory macrophage is 6 times that of normal macrophages [Journal of Biochemistry, 98, p.87, (1985)]. These facts indicate that thiol protease inhibitors are useful as anti-inflammatory drugs.

The type I allergy reaction is mediated by immunoglobulin E (IgE) produced in the subject immunized with an antigen. Estatin A, a thiol protease inhibitor, has been reported to specifically inhibit the production of IgE without affecting on the production of IgG [The Journal of Antibiotics, 42, p.1362, (1989)]. Accordingly, thiol protease inhibitors are considered to be useful as antiallergic drugs.

In case of necrosis of hepatic cells, it is believed that impairment of the cell membrane leads to an increase in the permeability of $Ca^{2+}$, an increase in intracellular $Ca^{2+}$ concentration, an activation of calpain, and, as the result, the decomposition of its substrate such as skeletal protein takes place, which results in the death of cells. Accordingly, a calpain inhibitor can be used as a therapeutic agent for fulminant hepatitis.

Cathepsins such as cathepsin B and cathepsin L are involved in decomposition of bone collagen in osteoclast. It has been reported that administration of an inhibitor of cathepsins, E-64 or estatin A, to a rat which has an enhanced bone destruction by administration of parathyroid hormone leads to a decrease of calcium concentration and hydroxyproline concentration in blood [Biochemical and Biophysical Research Communication, 125, p.441, (1984): Japanese Patent Publication (kokai) No. 218610/1990]. Accordingly, it is believed that an inhibitor of cathepsins can be a therapeutic agent for osteoporosis, hypercalcemia and the like.

There exist, as a substrate for calpain, sex hormone receptors such as estrogen receptor and androgen receptor, and it is known that calpain activates these receptors. Accordingly, it is considered that an abnormal sthenia of calpain causes a disease which is suspected to be caused by an abnormal activation of the sex hormone receptors, for example, breast carcinoma, prostatic carcinoma or prostatomegaly. It is believed that an inhibitor for calpain can be a therapeutic agent for the above disease.

Receptors for epidermal growth factor (EGF) are also considered to be activated in association with the canceration of cells. It is known that calpain activates the EGF receptors as its substrate. Furthermore, it has been reported that calpain is activated in cells which have been infected with adult T cell human leukocyte virus (ATLV/HTLV-1) [Seikagaku, 57, p.1202, (1985)]. On the other hand, it is said that cathepsin B is greatly involved in a process of cancer metastasis because it accelerates decomposition of collagen which is a important step for the cancer metastasis or directly decomposes collagen, and because it has a profound correlation with plasma membrane of neoplastic cells [Tumor Progression and Markers, p.47, (1982); Journal of Biological Chemistry, 256, p.8536, (1984)]. These facts suggest that a thiol protease inhibitor has an ability to suppress the growth of cancer cells and prevent the metastasis of cancer.

Activation of platelet causes the aggregation thereof which is a cause of thrombus. It has been reported that an inhibitor of calpain, E-64-d, suppressed aggregation of platelet caused by thrombin [Thrombosis Research, 57, p.847, (1990)]. Accordingly, the inhibitor of calpain can be used as an inhibitor against aggregation of platelet.

As described above, an abnormal sthenia of thiol protease causes various diseases and a validity of several thiol protease inhibitors in animal models has been reported. However, most of known inhibitors, for example, epoxy succinate derivatives such as E-64 [Agricultural and Biological Chemistry, 42, p.529, (1978)], E-64-d [Journal of Biochemistry, 93, p.1305, (1983)], NCO-700 [Japanese Patent Publication (kokai) No. 126879/1983], and estatins A and B [The Journal of Antibiotics, 42, p.1362, (1989)], or α-substituted ketone of a peptide such as chloromethyl ketone [Journal of Biochemistry, 99, p.173, (1986)] and acyloxymethyl ketone [Biochemistry, 30, p.4678, (1991)] are irreversible inhibitors. It is generally said that the irreversible inhibitors are highly toxic because they are liable to react with non-specifically to components consisting of living body, other than target enzymes. Therefore, there have been few compounds applicable to clinical use so far. Although peptidyl aldehydes such as leupeptin [The Journal of Antibiotics, 22, p.183, (1969)] or carpeptine [Journal of Enzyme Inhibition, 3, p.195, (1990)] are known as reversible inhibitors, they also have problems in chemical and in vivo stabilities, cell membrane permeabilities and the like.

SUMMARY OF THE INVENTION

The present inventors investigated into various compounds with aim of developing reversible inhibitors against thiol protease, which have excellent properties concerning absorbance on oral administration, tissue distribution and cell membrane permeability, and have found that certain derivatives of cyclopropenone have such desired properties.

Thus, the present invention provides cyclopropenone derivatives of general formula (I):

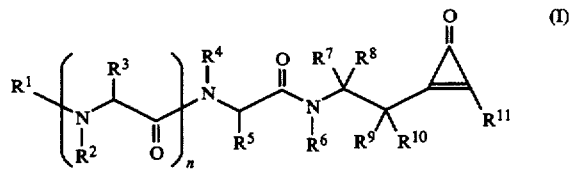

wherein $R^1$ is hydrogen atom, $R^{12}$—CO—, $R^{12}$—O—CO—, $R^{12}$—NH—CO— or $R^{12}$—SO$_2$— (in which $R^{12}$ is $C_1$-$C_{20}$ alkyl group optionally substituted by one or more substituents selected from the group consisting of $C_3$-$C_{15}$ cycloalkyl group, optionally substituted $C_6$-$C_{14}$ aryl group, $C_3$-$C_{15}$ cycloalkyloxy group, optionally substituted $C_6$-$C_{14}$ aryloxy group, optionally substituted $C_6$-$C_{14}$ arylthio group, optionally substituted $C_6$-$C_{14}$ arylsulfonyl group, optionally substituted $C_7$-$C_{20}$ aralkyloxy group, optionally substituted heterocyclic group, oxo group, hydroxyl group, $C_1$-$C_{10}$ alkoxycarbonyl group and carboxyl group; $C_3$-$C_{15}$ cycloalkyl group; optionally substituted $C_6$-$C_{14}$ aryl group or optionally substituted heterocyclic group); $R^2$, $R^4$ and $R^6$ each is independently hydrogen atom or $C_1$-$C_{10}$ alkyl group optionally substituted by $C_1$-$C_5$ alkoxy group or $C_1$-$C_5$ alkylthio group; $R^3$, $R^5$ and $R^7$ each is independently hydrogen atom, $C_1$-$C_{20}$ alkyl group optionally substituted by $C_3$-$C_{10}$ cycloalkyl group, $C_3$-$C_{10}$ cycloalkyl group or optionally substituted $C_7$-$C_{20}$ aralkyl group; $R^8$ is hydrogen atom or $C_1$-$C_{20}$ alkyl group; $R^7$ and $R^6$ taken together may form $C_3$-$C_{15}$ cycloalkyl group; $R^9$ is hydroxyl group or $C_2$-$C_{10}$ acyloxy group; $R^{10}$ is hydrogen atom; $R^9$ and $R^{10}$ taken together may form oxo group; $R^{11}$ is hydrogen atom, $C_1$-$C_{20}$ alkyl group optionally substituted by $C_3$-$C_{15}$ cycloalkyl group, $C_3$-$C_{15}$ cycloalkyl group, $C_2$-$C_{20}$ alkenyl group, optionally substituted $C_6$-$C_{14}$ aryl group, optionally substituted $C_7$-$C_{20}$ aralkyl group, optionally substituted heterocyclic group or —C($R^{13}$)($R^{14}$)—OH (in which $R^{13}$ and $R^{14}$ each is independently hydrogen atom, $C_1$-$C_{20}$ alkyl group, optionally substituted $C_7$-$C_{20}$ aralkyl group or optionally substituted $C_6$-$C_{14}$ aryl group, or $R^{13}$ and $R^{14}$ taken together may form $C_3$-$C_{15}$ cycloalkyl group); and n is 0 or 1 or pharmaceutically acceptable salts thereof.

The present invention also provides a pharmaceutical compositions containing, as an active ingredient, a cyclopropenone derivative of formula (I) or a salt thereof.

The present invention also provides a process for the preparation of cyclopropenone derivatives of formula (I).

DETAILED DESCRIPTION OF THE INVENTION

Definition

For the purpose of the invention the following terms used herein are defined as follows:

In the definition of $R^{12}$: examples of $C_1-C_{20}$ alkyl group include methyl group, ethyl group, propyl group, isopropyl group, butyl group, isobutyl group, sec-butyl group, tert-butyl group, pentyl group, isopentyl group, neopentyl group, tert-pentyl group, hexyl group, isohexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group and the like. Such an alkyl group may be optionally substituted by one or more substituents selected from the group consisting of $C_3-C_{15}$ cycloalkyl group such as cyclopropyl group, cyclobutyl group, cyclopentyl group, cyclohexyl group, cycloheptyl group, cyclooctyl group, cyclononyl group, cyclodecyl group, cycloundecyl group, cyclododecyl group, cyclotridecyl group, cyclotetradecyl group, cyclopentadecyl group or the like; $C_6-C_{14}$ aryl group such as phenyl group, naphthyl group, anthryl group; $C_3-C_{15}$ cycloalkyloxy group such as cyclopropyloxy group, cyclobutyloxy group, cyclopentyloxy group, cyclohexyloxy group, cycloheptyloxy group; cyclooctyloxy group, cyclodecyloxy group, cyclopentadecyloxy group or the like; $C_6-C_{14}$ aryloxy group such as phenoxy group, 1-naphthoxy group, 2-naphthoxy group or the like; $C_6-C_{14}$ arylthio group such as phenylthio group, 1-naphthylthio group, 2-naphthylthio group or the like; $C_6-C_{14}$ arylsulfonyl group such as phenylsulfonyl group, 1-naphthylsulfonyl group, 2-naphthylsulfonyl group or the like; $C_7-C_{20}$ aralkyloxy group such as benzyloxy group, 1-phenylethoxy group, 2-phenylethoxy group, 1-phenylpropoxy group, 2-phenylpropoxy group, 3-phenylpropoxy group, 4-phenylbutoxy group, 5-phenylpentyloxy group, 1-naphthylmethoxy group, 2-naphthylmethoxy group, 1-(1-naphthyl)ethoxy group, 2-(1-naphthyl)ethoxy group, 1-(2-naphthyl)ethoxy group, 2-(2-naphthyl)ethoxy group or the like; 5-10 membered heterocyclic group containing 1 to 4 hetero atoms selected from oxygen atom, sulfur atom and nitrogen atom to form a ring such as furan ring, dihydrofuran ring, tetrahydrofuran ring, pyran ring, dihydropyran ring, tetrahydropyran ring, benzofuran ring, isobenzofuran ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indolidine ring, indole ring, indoline ring, isoindole ring, isoindoline ring, indazole ring, benzoimidazole ring, purine ring, quinolidine ring, quinoline ring, phthalazine ring, naphthylidine ring, quinoxaline ring, quinazoline ring, cinnoline ring, pteridine ring, oxazole ring, oxazolidine ring, isoxazole ring, isoxazolidine ring, thiazole ring, thiazolidine ring, isothiazole ring, isothiazolidine ring, dioxane ring, dithian ring, morpholine ring, thiomorpholine ring or the like; $C_1-C_{10}$ alkoxycarbonyl group such as methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group, hexyloxycarbonyl group, heptyloxycarbonyl group, octyloxycarbonyl group, decyloxycarbonyl group or the like; oxo group; hydroxyl group and carboxyl group. Examples of $C_3-C_{15}$ cycloalkyl group, $C_6-C_{14}$ aryl group and heterocyclic group are the same as those illustrated in the definition of the substituents of $C_1-C_{20}$ alkyl group.

In the definition of $R^2$, $R^4$ and $R^6$, examples of $C_1-C_{10}$ alkyl group include methyl group, ethyl group, propyl group, isopropyl group, butyl group, isobutyl group, sec-butyl group, tert-butyl group, pentyl group, isopentyl group, neopentyl group, tert-pentyl group, hexyl group, isohexyl group, heptyl group, octyl group, nonyl group, decyl group and the like. Such an alkyl group may be optionally substituted by $C_1-C_5$ alkoxy group such as methoxy group, ethoxy group, propoxy group, isopropoxy group, butoxy group, isobutoxy group, tert-butoxy group, pentyloxy group, isopentyloxy group or the like or $C_1-C_5$ alkylthio group such as methylthio group, ethylthio group, propylthio group, isopropylthio group, butylthio group, isobutylthio group, tert-butylthio group, pentylthio group, isopentylthio group or the like.

In the definition of $R^3$, $R^5$ and $R^7$, examples of $C_1-C_{20}$ alkyl group optionally substituted by $C_3-C_{10}$ cycloalkyl group and $C_3-C_{10}$ cycloalkyl group are the same as those illustrated in the definition of $R^{12}$ except that cycloalkyl group is $C_3-C_{10}$ cycloalkyl group. Examples of $C_7-C_{20}$ aralkyl group are benzyl group, 1-phenethyl group, 2-phenethyl group, 1-phenylpropyl group, 2-phenylpropyl group, 3-phenylpropyl group, 4-phenylbutyl group, 5-phenylpentyl group, 1-naphthylmethyl group, 2-naphthylmethyl group, 1-(1-naphthyl)ethyl group, 1-(2-naphthyl)ethyl group, 2-(1-naphthyl)ethyl group, 2-(2-naphthyl)ethyl group and the like.

In the definition of $R^6$, examples of $C_1-C_{20}$ alkyl group are the same as those illustrated in the definition of $R^{12}$.

Examples of $C_3-C_{15}$ cycloalkyl group which $R^7$ and $R^8$ taken together may form are the same as those illustrated in the definition of $R^{12}$.

In the definition of $R^9$, examples of $C_2-C_{10}$ acyloxy group are alkylcarbonyloxy group such as acetoxy group, propionyloxy group, butyryloxy group, valeryloxy group and the like.

In the definition of $R^{11}$, examples of $C_1-C_{20}$ alkyl group optionally substituted by $C_3-C_{15}$ cycloalkyl group, $C_3-C_{15}$ cycloalkyl group, $C_6-C_{14}$ aryl group and heterocyclic group are the same as those illustrated in the definition of $R^{12}$, and examples of $C_2-C_{20}$ alkenyl group are vinyl group, 1-propenyl group, allyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group, 1-heptenyl group, 1-octenyl group, 1-nonenyl group, 1-decenyl group, 1-dodecenyl group, 1-pentadecenyl group and the like. Examples of $C_7-C_{20}$ aralkyl group are the same as those illustrated in the definition of $R^3$, $R^5$ and $R^7$.

In the definition of $R^{13}$ and $R^{14}$, examples of $C_1-C_{20}$ alkyl group and $C_6-C_{14}$ aryl group are the same as those illustrated in the definition of $R^{12}$, and examples of $C_7-C_{20}$ aralkyl group are the same as those illustrated in the definition of $R^3$, $R^5$ and $R^7$.

Examples of $C_3$-$C_{15}$ cycloalkyl group which $R^{13}$ and $R^{14}$ taken together may form are the same as those illustrated in the definition of $R^{12}$.

The aromatic and the heterocyclic groups which positioned at the end of each substituent as defined in the above may optionally have one or more substituents selected from the group consisting of halogen atom such as fluorine atom, chlorine atom, bromine atom or the like; $C_1$-$C_5$ alkyl group such as methyl group, ethyl group, propyl group, isopropyl group, butyl group, isobutyl group, sec-butyl group, tert-butyl group, pentyl group, isopentyl group, neopentyl group or the like; trifluoromethyl group; $C_1$-$C_5$ alkoxy group such as methoxy group, ethoxy group, propoxy group, isopropoxy group, butoxy group, isobutoxy group, tert-butoxy group, pentyloxy group, isopentyloxy group or the like; $C_1$-$C_5$ alkylenedioxy group such as methylenedioxy group, ethylenedioxy group, propylenedioxy group or the like; hydroxyl group; $C_2$-$C_6$ alkylcarbonyloxy group such as acetoxy group, propionyloxy group, butyryloxy group, valeryloxy group or the like; carboxyl group; $C_2$-$C_6$ alkoxycarbonyl group such as methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group or the like; oxo group; $C_2$-$C_6$ alkylcarbonyl such as acetyl group, propionyl group, butyryl group, valeryl group or the like; amino group; $C_1$-$C_5$ monoalkylamino group such as methylamino group, ethylamino group, propylamino group, isopropylamino group, butylamino group, isobutylamino group, tert-butylamino group, pentylamino group, isopentylamino group or the like; $C_2$-$C_{10}$ dialkylamino group such as dimethylamino group, ethylmethylamino group, diethylamino group, methylpropylamino group, diisopropylamino group or the like; $C_2$-$C_6$ alkylcarbonylamino group such as acetylamino group, propionylamino group, isopropionylamino group, butyrylamino group, valerylamino group or the like; carbamoyl group; $C_2$-$C_6$ alkylcarbamoyl group such as methylcarbamoyl group, ethylcarbamoyl group, propylcarbamoyl group, isopropylcarbamoyl group, butylcarbamoyl group, tert-butylcarbamoyl group, pentylcarbamoyl group or the like; $C_6$-$C_{14}$ aryl group such as phenyl group, naphthyl group or the like; and trimethylsilyl group.

Although all the compound (I) as defined above are useful for the purpose of the invention, there are some preferable compounds. Thus, compounds (I) included in the following [Group A] are preferable, and among compounds of [group A], those belong to [Group B] are particularly preferred.

Group A

Compound of formula (I), wherein $R^1$ is hydrogen atom, $R^{12}$—CO—, $R^{12}$—O—CO—, $R^{12}$—NH—CO— or $R^{12}$—SO$_2$— (in which $R^{12}$ is $C_1$-$C_{20}$ alkyl group optionally substituted by one or more substituents selected from the group consisting of $C_3$-$C_{15}$ cycloalkyl group, optionally substituted $C_6$-$C_{14}$ aryl group, optionally substituted $C_6$-$C_{14}$ aryloxy group, optionally substituted $C_6$-$C_{14}$ arylthio group, optionally substituted $C_7$-$C_{20}$ aralkyloxy group, optionally substituted heterocyclic group, oxo group, hydroxyl group, $C_1$-$C_{10}$ alkoxycarbonyl group and carboxyl group; $C_3$-$C_{15}$ cycloalkyl group, optionally substituted $C_6$-$C_{14}$ aryl group or optionally substituted heterocyclic group); $R^2$, $R^4$ and $R^6$ each is independently hydrogen atom, $C_1$-$C_{10}$ alkyl group optionally substituted by $C_1$-$C_5$ alkylthio group; $R^3$, $R^5$ and $R^7$ each is hydrogen atom, $C_1$-$C_{20}$ alkyl group optionally substituted by $C_3$-$C_{10}$ cycloalkyl group, $C_3$-$C_{10}$ cycloalkyl group or optionally substituted $C_7$-$C_{20}$ aralkyl group; $R^8$ is hydrogen atom or $C_1$-$C_{20}$ alkyl group; $R^9$ is hydroxyl group or $C_2$-$C_{10}$ acyloxy group; $R^{10}$ is hydrogen atom; or $R^9$ and $R^{10}$ taken together may form oxo group; $R^{11}$ is hydrogen atom, $C_1$-$C_{20}$ alkyl group optionally substituted by $C_3$-$C_{15}$ cycloalkyl group, $C_3$-$C_{15}$ cycloalkyl group, $C_2$-$C_{20}$ alkenyl group, optionally substituted $C_6$-$C_{14}$ aryl group, $C_7$-$C_{20}$ aralkyl group, optionally substituted heterocyclic group, or —C($R^{13}$)($R^{14}$)—OH (in which $R^{13}$ and $R^{14}$ each is independently hydrogen atom, $C_1$-$C_{20}$ alkyl group or $C_6$-$C_{14}$ aryl group; and n is 0 or 1.

Group B

Compound of formula (I), wherein $R^1$ is $R^{12}$—CO—, $R^{12}$—O—CO—, $R^{12}$—NH—CO— or $R^{12}$—SO$_2$— (in which $R^{12}$ is $C_1$-$C_{15}$ alkyl group optionally substituted by one or more substituents selected from the group consisting of $C_3$-$C_{10}$ cycloalkyl group, optionally substituted $C_6$-$C_{14}$ aryloxy group, optionally substituted $C_6$-$C_{14}$ arylthio group, optionally substituted $C_7$-$C_{20}$ aralkyloxy group, optionally substituted heterocyclic group and oxo group; $C_3$-$C_{10}$ cycloalkyl group; optionally substituted $C_6$-$C_{10}$ aryl group or optionally substituted heterocyclic group); $R^2$, $R^4$ and $R^6$ each is independently hydrogen atom or $C_1$-$C_{10}$ alkyl group; $R^3$, $R^5$ and $R^7$ each is independently hydrogen atom, $C_1$-$C_{15}$ alkyl group optionally substituted by $C_3$-$C_{10}$ cycloalkyl group, $C_3$-$C_{10}$ cycloalkyl group or optionally substituted $C_7$-$C_{20}$ aralkyl group; $R^8$ is hydrogen atom; $R^9$ is hydroxyl group or $C_2$-$C_{10}$ acyloxy group; $R^{10}$ is hydrogen atom; and $R^{11}$ is hydrogen atom, $C_1$-$C_{15}$ alkyl group optionally substituted by $C_3$-$C_{10}$ cycloalkyl group, $C_3$-$C_{10}$ cycloalkyl group, $C_7$-$C_{20}$ aralkyl group, optionally substituted $C_6$-$C_{10}$ aryl group or optionally substituted heterocyclic group.

Furthermore, among the compounds in [Group B], the compounds belong to [Group C] and [Group D] are preferred and of the compounds in [Group C], those in [Group E] and [Group F] are more preferred. Among compounds in [Group D], those in [Group G] are more preferred.

Group C

Compounds of formula (I), wherein $R^1$ is $R^{12}$—CO—, $R^{12}$—O—CO— or $R^{12}$—NH—CO— (in which $R^{12}$ is $C_1$-$C_{15}$ alkyl group optionally substituted by one or more substituents selected from the group consisting of $C_3$-$C_{10}$ cycloalkyl group, optionally substituted $C_6$-$C_{14}$ aryl group, optionally substituted $C_6$-$C_{14}$ aryloxy group, optionally substituted $C_6$-$C_{14}$ arylthio group, optionally substituted $C_7$-$C_{20}$ aralkyloxy group, optionally substituted heterocyclic group and oxo group; or optionally substituted $C_6$-$C_{10}$ aryl group); $R^2$, $R^4$ and $R^6$ each is independently hydrogen atom or $C_1$-$C_{10}$ alkyl group; $R^3$, $R^5$ and $R^7$ each hydrogen atom, $C_1$-$C_{15}$ alkyl group optionally substituted by $C_3$-$C_{10}$ cycloalkyl group, $C_3$-$C_{10}$ cycloalkyl group or $C_7$-$C_{20}$ aralkyl group; $R^8$ is hydrogen atom; $R^9$ is hydroxyl group or $C_2$-$C_{10}$ acyloxy group; $R^{10}$ is hydrogen atom; and $R^{11}$ is hydrogen atom, $C_1$-$C_{15}$ alkyl group optionally substituted by $C_3$-$C_{10}$ cycloalkyl group, $C_3$-$C_{10}$ cycloalkyl group, $C_7$-$C_{20}$ aralkyl group, optionally substituted $C_6$–$C_{10}$ aryl group or optionally substituted heterocyclic group.

Group D

Compounds of formula (I), wherein $R^1$ is $R^{12}$—$SO_2$— (in which $R^{12}$ is $C_1$–$C_{15}$ alkyl group optionally substituted by one or more substituents selected from the group consisting of $C_3$–$C_{10}$ cycloalkyl group, optionally substituted $C_6$–$C_{14}$ aryl group, optionally substituted $C_6$–$C_{14}$ aryloxy group, $C_6$–$C_{14}$ arylthio group, optionally substituted $C_7$–$C_{20}$ aralkyloxy group, optionally substituted heterocyclic group and oxo group; $C_3$–$C_{10}$ cycloalkyl group; optionally substituted $C_6$–$C_{10}$ aryl group or optionally substituted heterocyclic group); and $R^{11}$ is hydrogen atom, optionally substituted $C_6$–$C_{10}$ aryl group or optionally substituted heterocyclic group.

Group E

Compounds of formula (I), wherein $R^1$ is $R^{12}$—O—CO— (in which $R^{12}$ is $C_1$–$C_{15}$ alkyl group optionally substituted by one or more substituents selected from the group consisting of $C_3$–$C_{10}$ cycloalkyl group, $C_6$–$C_{14}$ aryl group and heterocyclic group or $C_3$–$C_{10}$ cycloalkyl group); $R^4$ and $R^6$ each is hydrogen atom; $R^{11}$ is hydrogen atom, $C_1$–$C_{15}$ alkyl group optionally substituted by $C_3$–$C_{10}$ cycloalkyl group, $C_3$–$C_{10}$ cycloalkyl group, $C_7$–$C_{20}$ aralkyl group or $C_6$–$C_{10}$ aryl group; and n is 0.

Group F

Compound of formula (I), wherein $R^1$ is $R^{12}$—O—CO— (in which $R^{12}$ is $C_1$–$C_{15}$ alkyl group optionally substituted by one or more substituents selected from the group consisting of $C_3$–$C_{10}$ cycloalkyl group, $C_6$–$C_{14}$ aryl group, and heterocyclic group); $R^4$ and $R^6$ each is hydrogen atom; $R^5$ and $R^7$ each is independently hydrogen atom, $C_1$–$C_{15}$ alkyl group optionally substituted by $C_3$–$C_{10}$ cycloalkyl group or $C_7$–$C_{20}$ aralkyl group; $R^9$ is hydroxyl group; $R^{10}$ is hydrogen atom; $R^{11}$ is optionally substituted heterocyclic group; and n is 0.

Group G

Compounds of formula (I), wherein $R^{12}$ is optionally substituted $C_6$–$C_{10}$ aryl group or optionally substituted heterocyclic group.

As will be understood from the structure, the cyclopropenone derivatives of formula (I) can form pharmaceutically acceptable salts thereof. Examples of such salts include, when an acidic group is present, metal salts such as lithium salt, sodium salt, potassium salt, magnesium salt, calcium salt or the like and ammonium salts such as ammonium salt, methylammonium salt, dimethylammonium salt, trimethylammonium salt, dicyclohexylammonium salt or the like and, when a basic group is present, mineral acid salts such as hydrochloride, hydrobromide, sulfate, nitrate, phosphate or the like and organic acid salts such as methanesulfonate, benzenesulfonate, p-toluenesulfonate, acetate, propionate, tartrate, fumarate, maleate, malate, oxalate, succinate, citrate, benzoate, mandelate, cinnamate, lactate or the like.

Considering the stereochemistry of the sites of double bond existing in the cyclopropenone derivatives of formula (I), these compounds can take (E), (Z) or (EZ) form. As to the stereochemistry of asymmetric carbon, compounds (I) can be independently in (R), (S) or (RS) form.

The following Tables 1 and 2 shows examples of the cyclopropenone derivatives of formula (I) in case of n=0 and n=1, respectively.

TABLE 1
(n = 0)

| Compd. No. | R¹ | R⁴ | R⁵ | R⁶ | R⁷ | R⁸ | R⁹ | R¹⁰ | R¹¹ |
|---|---|---|---|---|---|---|---|---|---|
| 1 | cyclohexyl-CH₂-O-C(=O)- | H | —CH₂-(phenyl) | H | —CH₃ | H | —OH | H | H |
| 2 | phenyl-O-CH₂-C(=O)- | H | —CH₂-(phenyl) | H | —CH₃ | H | —OH | H | H |
| 3 | phenyl-S(=O)₂- | H | —CH₂-(phenyl) | H | —CH₃ | H | —OH | H | H |
| 4 | cyclohexyl-CH₂-O-C(=O)- | H | —CH₂CH(CH₃)₂ | H | —CH(CH₃)₂ | H | —OH | H | H |
| 5 | phenyl-CH₂-O-C(=O)- | H | —CH₂CH(CH₃)₂ | —CH₃ | —CH(CH₃)₂ | H | —OH | H | H |
| 6 | phenyl-CH₂-O-C(=O)- | —CH₃ | —CH₂CH(CH₃)₂ | H | —CH(CH₃)₂ | H | —OH | H | H |
| 7 | phenyl-O-CH₂-C(=O)- | H | —CH₂CH(CH₃)₂ | H | —CH(CH₃)₂ | H | —OH | H | H |

TABLE 1-continued

| | | | | | | | |
|---|---|---|---|---|---|---|---|
| 8 | ~C(=O)NH-CH2-C6H5 | H | —CH2CH(CH3)2 | H | —CH(CH3)2 | H | —OH | H | H |
| 9 | —S(=O)2-C6H5 | H | —CH2CH(CH3)2 | H | —CH(CH3)2 | H | —OH | H | H |
| 10 | —C(=O)O-CH2-C6H5 | H | —CH2CH(CH3)2 | H | —CH2CH(CH3)2 | H | —OH | H | H |
| 11 | —S(=O)2-C6H5 | H | —CH2CH(CH3)2 | H | —CH2CH(CH3)2 | H | —OH | H | H |
| 12 | —C(=O)O-CH2-C6H11 | H | —CH2-C6H5 | H | —CH2CH(CH3)2 | H | —OH | H | H |
| 13 | —C(=O)O-CH2-C6H11 | H | —CH3 | H | —CH2CH2CH3 | H | —OH | H | H |
| 14 | —C(=O)O-CH2-C6H5 | H | —CH(CH3)2 | H | —CH2CH2CH3 | H | —OH | H | H |

TABLE 1-continued

| # | Structure | | | | | | | |
|---|---|---|---|---|---|---|---|---|
| 15 | cyclohexyl-CH2-O-C(=O)- | H | —CH2CH(CH3)2 | H | —CH2CH2CH2CH3 | H | —OH | H | H |
| 16 | benzyl-O-C(=O)- | H | —CH2CH(CH3)2 | H | —CH2CH2CH2CH3 | H | —OH | H | H |
| 17 | phenyl-O-CH2-C(=O)- | H | —CH2CH(CH3)2 | H | —CH2CH2CH2CH3 | H | —OH | H | H |
| 18 | phenyl-O-CH2-C(=O)- | H | —CH2CH(CH3)2 | H | —CH2CH2CH2CH3 | H | —OH | H | H |
| 19 | phenyl-SO2- | H | —CH2CH(CH3)2 | H | —CH2CH2CH2CH3 | H | —OH | H | H |
| 20 | benzyl-O-C(=O)- | H | —CH2CH(CH3)2 | H | —CH2CH2CH2CH3 | H | —OC(=O)CH3 | H | H |
| 21 | cyclohexyl-CH2-O-C(=O)- | H | —CH2CH(CH3)2 | H | —CH3 | —CH3 | —OH | H | H |
| 22 | benzyl-O-C(=O)- | H | —CH2-phenyl | H | —CH3 | —CH3 | —OH | H | H |

TABLE 1-continued

| # | R1 | | | | | | |
|---|---|---|---|---|---|---|---|
| 23 | benzyl ester (–C(=O)O–CH2–C6H5) | H | –CH2–C6H5 | H | –CH3 | =O | H |
| 24 | benzyl ester | H | –CH2CH(CH3)2 | H | –CH2CH2CH2CH2– | –OH | H |
| 25 | cyclohexylmethyl ester | H | –CH(CH3)2 | H | –CH2–C6H5 | –OH | H |
| 26 | benzyl ester | H | –CH2CH(CH3)2 | H | –CH2–C6H5 | –OH | H |
| 27 | phenylsulfonyl (C6H5–SO2–) | H | –CH2CH(CH3)2 | H | –CH2–C6H5 | –OH | H |
| 28 | cyclohexylmethyl ester | H | –CH2CH(CH3)2 | H | –CH2CH2–C6H5 | –OH | H |
| 29 | cyclohexylmethyl ester | H | –CH2CH(CH3)2 | H | –CH3 | –OH | –CH3 |

TABLE 1-continued

| | | | | | | | |
|---|---|---|---|---|---|---|---|
| 30 | cyclohexyl-CH2-O-C(=O)- | H | -CH2- (phenyl) | H | -CH3 | H | -OH | H | -CH3 |
| 31 | phenyl-CH2-O-C(=O)- | H | -CH2CH(CH3)2 | H | -CH(CH3)2 | H | -OH | H | -CH3 |
| 32 | cyclohexyl-CH2-O-C(=O)- | H | -CH2CH(CH3)2 | H | -CH2CH(CH3)2 | H | -OH | H | -CH3 |
| 33 | (CH3)3COC(=O)- | H | -CH2CH(CH3)2 | H | -CH2CH2CH3 | H | -OH | H | -CH3 |
| 34 | cyclohexyl-CH2-O-C(=O)- | H | -CH2CH(CH3)2 | H | -CH2CH2CH3 | H | -OH | H | -CH3 |
| 35 | H | | -CH2CH(CH3)2 | H | -CH2CH2CH3 | H | -OH | H | -CH3 |
| 36 | phenyl-O-CH2-C(=O)- | | -CH2CH(CH3)2 | H | -CH2CH2CH3 | H | -OH | H | -CH3 |
| 37 | phenyl-S(=O)2- | H | -CH2CH(CH3)2 | H | -CH2CH2CH3 | H | -OH | H | -CH3 |

Note: Row 30 shows -CH2- attached to phenyl (benzyl) in the R group column.

TABLE 1-continued

| # | Structure | | | | | | | | |
|---|---|---|---|---|---|---|---|---|---|
| 38 | ester-CH₂-cyclohexyl | H | —CH₂CH(CH₃)₂ | H | —CH₂—C₆H₅ | H | —OH | H | —CH₃ |
| 39 | ester-CH₂-cyclohexyl | H | —CH₂—C₆H₅ | H | —CH₃ | H | —OH | H | —CH₂CH₃ |
| 40 | ester-CH₂-phenyl | H | —CH₂CH(CH₃)₂ | H | —CH₂CH(CH₃)₂ | H | —OH | H | —CH₂CH₃ |
| 41 | ester-CH₂-cyclohexyl | H | —CH₂CH(CH₃)₂ | H | —CH₂CH₂CH₃ | H | —OH | H | —CH₂CH₃ |
| 42 | ester-CH₂-phenyl | H | —CH₂CH(CH₃)₂ | H | —CH₂CH(CH₃)₂ | H | —OH | H | —CH₂CH(CH₃)₂ |
| 43 | ester-CH₂-cyclohexyl | H | —CH₂—C₆H₅ | H | —CH₃ | H | —OH | H | —CH₂CH₂CH(CH₃)₂ |
| 44 | ester-CH₂-cyclohexyl | H | —CH₂CH(CH₃)₂ | H | —CH₂CH₂CH₃ | H | —OH | H | —CH₂CH₂CH(CH₃)₂ |

TABLE 1-continued
| | | | | | | | | |
|---|---|---|---|---|---|---|---|---|
| 45 | 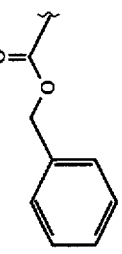 | H | —CH₂CH(CH₃)₂ | H | H | —OH | H | 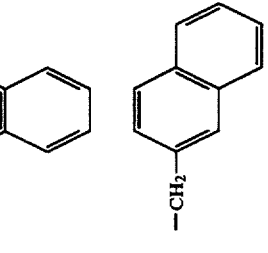 |
| 46 | 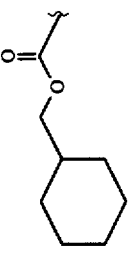 | H | 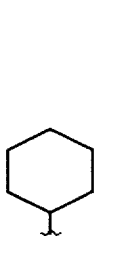 | H | —CH₂CH₂CH₂CH₃ | H | —OH | H | 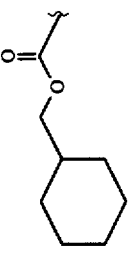 |
| 47 | 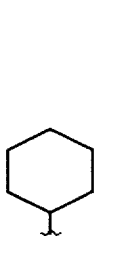 | H | —CH₂CH(CH₃)₂ | H | —CH₃ | H | —OH | H | 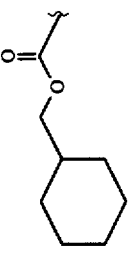 |
| 48 | 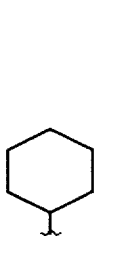 | H | 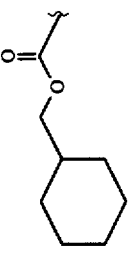 | H | —CH(CH₃)₂ | H | —OH | H | 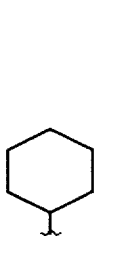 |
| 49 | 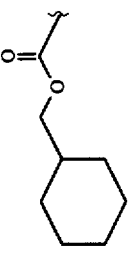 | H | —CH₂CH(CH₃)₂ | H | —CH₃ | H | —OH | H | 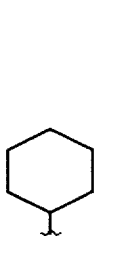 |
| 50 | 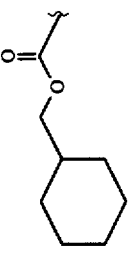 | H | —CH₂CH(CH₃)₂ | H | —CH₂CH(CH₃)₂ | H | —OH | H | 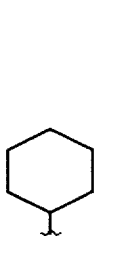 |
| 51 | 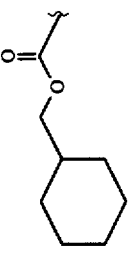 | H | 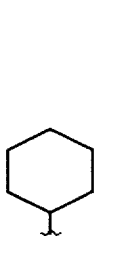 | H | —CH₂CH₂CH₂CH₃ | H | —OH | H | 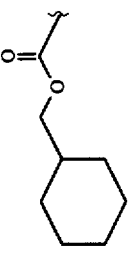 |

TABLE 1-continued

| | | | | | | | |
|---|---|---|---|---|---|---|---|
| 52 | ![ester-cyclohexyl] | H | —CH₂CH(CH₃)₂ | H | —CH(CH₃)₂ | H | H | allyl |
| 53 | ![ester-phenyl] | H | —CH₂CH(CH₃)₂ | H | —CH(CH₃)₂ | —OH | H | allyl |
| 54 | ![sulfonyl-phenyl] | H | —CH₂CH(CH₃)₂ | H | —CH(CH₃)₂ | —OH | H | allyl |
| 55 | ![ester-cyclohexyl] | H | —CH₂CH(CH₃)₂ | H | —CH₂CH₂CH₂CH₃ | —OH | H | cis-pentenyl |
| 56 | ![ester-phenyl] | H | —CH₂CH(CH₃)₂ | H | —CH₂CH₂CH₂CH₃ | —OH | H | cis-pentenyl |
| 57 | ![ester-cyclohexyl] | H | —CH₂CH(CH₃)₂ | H | —CH₂CH₂CH₂CH₃ | —OH | H | trans-pentenyl |
| 58 | ![ester-phenyl] | H | —CH₂CH(CH₃)₂ | H | —CH₂CH₂CH₂CH₃ | —OH | H | trans-pentenyl |

TABLE 1-continued

| | | | | | | | |
|---|---|---|---|---|---|---|---|
| 59 | [cyclohexylmethyl ester] | H | —CH2—[phenyl] | H | —CH3 | —OH | H | [allyl] |
| 60 | [benzyl ester] | H | —CH2CH(CH3)2 | H | —CH(CH3)2 | —OH | H | [allyl] |
| 61 | [benzyl ester] | H | —CH2CH(CH3)2 | H | —CH(CH3)2 | —OH | H | [2-butenyl] |
| 62 | [benzyl ester] | H | —CH2CH(CH3)2 | H | —CH(CH3)2 | —OH | H | [2-butenyl] |
| 63 | [cyclohexylmethyl ester] | H | —CH2CH(CH3)2 | H | —CH3 | —OH | H | [phenyl] |
| 64 | [cyclohexylmethyl ester] | H | —CH2—[phenyl] | H | —CH3 | —OH | H | [phenyl] |
| 65 | [phenylsulfonyl] | H | —CH2—[phenyl] | H | —CH3 | —OH | H | [phenyl] |

TABLE 1-continued

| | | | | | | |
|---|---|---|---|---|---|---|
| 66 | ⟡–C(=O)–O–CH₂–C₆H₅ | H | H | H | —CH(CH₃)₂ | —OH | H | ⟡–C₆H₅ |
| 67 | ⟡–C(=O)–O–CH₂–C₆H₁₁ | H | —CH₃ | H | —CH(CH₃)₂ | —OH | H | ⟡–C₆H₅ |
| 68 | ⟡–C(=O)–O–CH₂–C₆H₅ | H | —CH₃ | H | —CH(CH₃)₂ | —OH | H | ⟡–C₆H₅ |
| 69 | ⟡–C(=O)–O–CH₂–C₆H₁₁ | H | —CH(CH₃)₂ | H | —CH(CH₃)₂ | —OH | H | ⟡–C₆H₅ |
| 70 | ⟡–C(=O)–O–CH₂–C₆H₅ | H | —CH(CH₃)₂ | H | —CH(CH₃)₂ | —OH | H | ⟡–C₆H₅ |
| 71 | CH₃CH₂OC(=O)— | H | —CH₂CH(CH₃)₂ | H | —CH(CH₃)₂ | —OH | H | ⟡–C₆H₅ |
| 72 | ⟡–C(=O)–O–CH₂CH(CH₃)₂ | H | —CH₂CH(CH₃)₂ | H | —CH(CH₃)₂ | —OH | H | ⟡–C₆H₅ |

TABLE 1-continued

| | | | | | | |
|---|---|---|---|---|---|---|
| 73 | (CH₃)₃COC(O)— | H | —CH₂CH(CH₃)₂ | H | —CH(CH₃)₂ | H | H | Ph |
| 74 | isopentyl ester | H | —CH₂CH(CH₃)₂ | H | —CH(CH₃)₂ | —OH | H | Ph |
| 75 | cyclopropylmethyl ester | H | —CH₂CH(CH₃)₂ | H | —CH(CH₃)₂ | —OH | H | Ph |
| 76 | cyclopentylmethyl ester | H | —CH₂CH(CH₃)₂ | H | —CH(CH₃)₂ | —OH | H | Ph |
| 77 | cyclohexylmethyl ester | H | —CH₂CH(CH₃)₂ | H | —CH(CH₃)₂ | —OH | H | Ph |
| 78 | cyclohexylmethyl ester | H | —CH₂CH(CH₃)₂ | H | —CH(CH₃)₂ | —OC(O)CH₃ | H | Ph |
| 79 | cyclohexylmethyl ester | H | —CH₂CH(CH₃)₂ | H | —CH(CH₃)₂ | =O | | Ph |

TABLE 1-continued

| | | | | | | |
|---|---|---|---|---|---|---|
| 80 | cyclohexyl-CH2-O-C(=O)- | H | —CH2CH(CH3)2 | CH3 | —CH(CH3)2 | H | phenyl-CH2- |
| 81 | cyclopropyl-O-C(=O)- | H | —CH2CH(CH3)2 | H | —CH(CH3)2 | —OH | phenyl-CH2- |
| 82 | cyclohexyl-O-C(=O)- | H | —CH2CH(CH3)2 | H | —CH(CH3)2 | —OH | phenyl-CH2- |
| 83 | phenyl-CH2-O-C(=O)- | H | —CH2CH(CH3)2 | H | —CH(CH3)2 | —OH | phenyl-CH2- |
| 84 | phenyl-CH2-O-C(=O)- | H | —CH2CH(CH3)2 | —CH3 | —CH(CH3)2 | —OH | phenyl-CH2- |
| 85 | phenyl-CH2-O-C(=O)- | —CH3 | —CH2CH(CH3)2 | H | —CH(CH3)2 | —OH | phenyl-CH2- |
| 86 | phenyl-CH2-O-C(=O)- | —CH3 | —CH2CH(CH3)2 | —CH3 | —CH(CH3)2 | —OH | phenyl-CH2- |

TABLE 1-continued
| | | | | | | | |
|---|---|---|---|---|---|---|---|
| 87 | 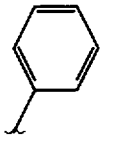 | H | —CH₂CH(CH₃)₂ | H | —CH(CH₃)₂ | H | —OH | H | 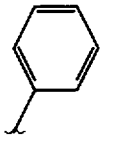 |
| 88 | 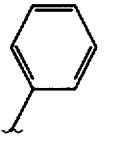 | H | —CH₂CH(CH₃)₂ | H | —CH(CH₃)₂ | H | —OH | H | 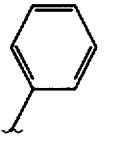 |
| 89 | 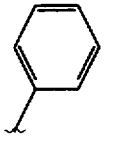 | H | —CH₂CH(CH₃)₂ | H | —CH(CH₃)₂ | H | —OH | H | 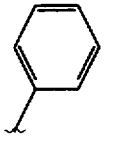 |
| 90 | 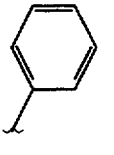 | H | —CH₂CH(CH₃)₂ | H | —CH(CH₃)₂ | H | —OH | H | 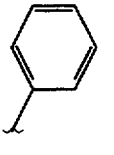 |
| 91 | 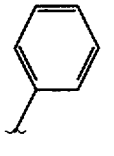 | H | —CH₂CH(CH₃)₂ | H | —CH(CH₃)₂ | H | —OH | H | 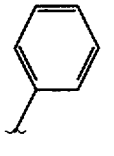 |
| 92 | 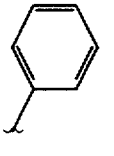 | H | —CH₂CH(CH₃)₂ | H | —CH(CH₃)₂ | H | —OH | H | 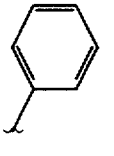 |
| 93 | 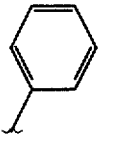 | H | —CH₂CH(CH₃)₂ | H | —CH(CH₃)₂ | H | —OH | H | 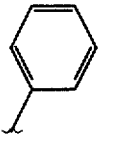 |

TABLE 1-continued

| # | R1 | | R2 | | R3 | R4 | R5 | Ar |
|---|---|---|---|---|---|---|---|---|
| 94 | 2-Cl-C6H4-CH2-O-C(=O)- | H | —CH2CH(CH3)2 | H | —CH(CH3)2 | H | —OH | H | phenyl |
| 95 | 4-Cl-C6H4-CH2-O-C(=O)- | H | —CH2CH(CH3)2 | H | —CH(CH3)2 | H | —OH | H | phenyl |
| 96 | C6H5-CH2CH2-O-C(=O)- | H | —CH2CH(CH3)2 | H | —CH(CH3)2 | H | —OH | H | phenyl |
| 97 | 2-pyridyl-CH2-O-C(=O)- | H | —CH2CH(CH3)2 | H | —CH(CH3)2 | H | —OH | H | phenyl |
| 98 | 3-pyridyl-CH2-O-C(=O)- | H | —CH2CH(CH3)2 | H | —CH(CH3)2 | H | —OH | H | phenyl |
| 99 | 4-pyridyl-CH2-O-C(=O)- | H | —CH2CH(CH3)2 | H | —CH(CH3)2 | H | —OH | H | phenyl |
| 100 | 2-furyl-CH2-O-C(=O)- | H | —CH2CH(CH3)2 | H | —CH(CH3)2 | H | —OH | H | phenyl |

TABLE 1-continued

| | | | | | | | |
|---|---|---|---|---|---|---|---|
| 101 | [thiophene-CH₂-O-C(=O)-] | H | —CH₂CH(CH₃)₂ | H | —CH(CH₃)₂ | H | H | Ph |
| 102 | [phenyl-O-C(=O)-] | H | —CH₂CH(CH₃)₂ | H | —CH(CH₃)₂ | H | —OH | Ph |
| 103 | [2-naphthyl-O-C(=O)-] | H | —CH₂CH(CH₃)₂ | H | —CH(CH₃)₂ | H | —OH | Ph |
| 104 | [2-naphthyl-O-C(=O)-] | H | —CH₂CH(CH₃)₂ | H | —CH(CH₃)₂ | H | —OH | Ph |
| 105 | H | H | —CH₂CH(CH₃)₂ | H | —CH(CH₃)₂ | H | —OH | Ph |
| 106 | $CH_3-C(=O)-$ | | —CH₂CH(CH₃)₂ | H | —CH(CH₃)₂ | H | —OH | Ph |
| 107 | $CH_3CH_2-C(=O)-$ | | —CH₂CH(CH₃)₂ | H | —CH(CH₃)₂ | H | —OH | Ph |

TABLE 1-continued

| | | | | | | | |
|---|---|---|---|---|---|---|---|
| 108 | CH₃CH₂C(=O)- (propanoyl, propyl chain) | H | —CH₂CH(CH₃)₂ | H | —CH(CH₃)₂ | H | H | Ph |
| 109 | (CH₃)₂CHC(=O)— | H | —CH₂CH(CH₃)₂ | H | —CH(CH₃)₂ | H | —OH | Ph |
| 110 | CH₃CH₂CH₂C(=O)— | H | —CH₂CH(CH₃)₂ | H | —CH(CH₃)₂ | H | —OH | Ph |
| 111 | (CH₃)₂CHCH₂C(=O)— | H | —CH₂CH(CH₃)₂ | H | —CH(CH₃)₂ | H | —OH | Ph |
| 112 | (CH₃)₃CC(=O)— | H | —CH₂CH(CH₃)₂ | H | —CH(CH₃)₂ | H | —OH | Ph |
| 113 | CH₃(CH₂)₃C(=O)— | H | —CH₂CH(CH₃)₂ | H | —CH(CH₃)₂ | H | —OH | Ph |
| 114 | (CH₃)₂CHCH₂CH₂C(=O)— | H | —CH₂CH(CH₃)₂ | H | —CH(CH₃)₂ | H | —OH | Ph |
| 115 | CH₃(CH₂)₅C(=O)— | H | —CH₂CH(CH₃)₂ | H | —CH(CH₃)₂ | H | —OH | Ph |

TABLE 1-continued
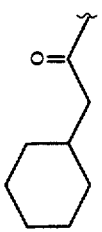
| | | | | | | | |
|---|---|---|---|---|---|---|---|
| 116 | CH₃(CH₂)₆C(=O)— | H | —CH₂CH(CH₃)₂ | H | —CH(CH₃)₂ | H | H | Ph |
| 117 | CH₃(CH₂)₇C(=O)— | H | —CH₂CH(CH₃)₂ | H | —CH(CH₃)₂ | H | —OH | Ph |
| 118 | CH₃(CH₂)₈C(=O)— | H | —CH₂CH(CH₃)₂ | H | —CH(CH₃)₂ | H | —OH | Ph |
| 119 | CH₃(CH₂)₉C(=O)— | H | —CH₂CH(CH₃)₂ | H | —CH(CH₃)₂ | H | —OH | Ph |
| 120 | CH₃(CH₂)₁₀C(=O)— | H | —CH₂CH(CH₃)₂ | H | —CH(CH₃)₂ | H | —OH | Ph |
| 121 | CH₃(CH₂)₁₂C(=O)— | H | —CH₂CH(CH₃)₂ | H | —CH(CH₃)₂ | H | —OH | Ph |
| 122 | CH₃(CH₂)₁₄C(=O)— | H | —CH₂CH(CH₃)₂ | H | —CH(CH₃)₂ | H | —OH | Ph |
| 123 | cyclohexyl-CH₂-C(=O)— | H | —CH₂CH(CH₃)₂ | H | —CH(CH₃)₂ | H | —OH | Ph |

TABLE 1-continued

| # | | | | | | | | | |
|---|---|---|---|---|---|---|---|---|---|
| 124 | (3-oxo-propyl-cyclohexyl) | H | —CH$_2$CH(CH$_3$)$_2$ | H | —CH(CH$_3$)$_2$ | H | H | H | phenyl |
| 125 | (4-oxo-butyl-cyclohexyl) | H | —CH$_2$CH(CH$_3$)$_2$ | H | —CH(CH$_3$)$_2$ | H | —OH | H | phenyl |
| 126 | cyclopropylcarbonyl | H | —CH$_2$CH(CH$_3$)$_2$ | H | —CH(CH$_3$)$_2$ | H | —OH | H | phenyl |
| 127 | cyclobutylcarbonyl | H | —CH$_2$CH(CH$_3$)$_2$ | H | —CH(CH$_3$)$_2$ | H | —OH | H | phenyl |
| 128 | cyclopentylcarbonyl | H | —CH$_2$CH(CH$_3$)$_2$ | H | —CH(CH$_3$)$_2$ | H | —OH | H | phenyl |
| 129 | cyclohexylcarbonyl | H | —CH$_2$CH(CH$_3$)$_2$ | H | —CH(CH$_3$)$_2$ | H | —OH | H | phenyl |
| 130 | cycloheptylcarbonyl | H | —CH$_2$CH(CH$_3$)$_2$ | H | —CH(CH$_3$)$_2$ | H | —OH | H | phenyl |

TABLE 1-continued

| | | | | | | | |
|---|---|---|---|---|---|---|---|
| 131 | cyclooctyl-C(=O)- | H | —CH₂CH(CH₃)₂ | H | —CH(CH₃)₂ | H | H | phenyl |
| 132 | PhCH₂-C(=O)- | H | —CH₂CH(CH₃)₂ | H | —CH(CH₃)₂ | —OH | H | phenyl |
| 133 | Ph(CH₂)₂-C(=O)- | H | —CH₂CH(CH₃)₂ | H | —CH(CH₃)₂ | —OH | H | phenyl |
| 134 | Ph(CH₂)₃-C(=O)- | H | —CH₂CH(CH₃)₂ | H | —CH(CH₃)₂ | —OH | H | phenyl |
| 135 | (2-naphthyl)CH₂-C(=O)- | H | —CH₂CH(CH₃)₂ | H | —CH(CH₃)₂ | —OH | H | phenyl |
| 136 | (1-naphthyl)CH₂-C(=O)- | H | —CH₂CH(CH₃)₂ | H | —CH(CH₃)₂ | —OH | H | phenyl |
| 137 | CH₃C(=O)CH₂CH₂-C(=O)- | H | —CH₂CH(CH₃)₂ | H | —CH(CH₃)₂ | —OH | H | phenyl |

TABLE 1-continued

| | | | | | | | |
|---|---|---|---|---|---|---|---|
| 138 | (CH3CH(OH)CH2C(O)–) | H | –CH2CH(CH3)2 | H | –CH(CH3)2 | H | H | Ph |
| 139 | (CH3C(O)CH2CH2C(O)–) | H | –CH2CH(CH3)2 | H | –CH(CH3)2 | –OH | H | Ph |
| 140 | (PhC(O)CH2CH2C(O)–) | H | –CH2CH(CH3)2 | H | –CH(CH3)2 | –OH | H | Ph |
| 141 | (PhCH(OH)CH2CH2C(O)–) | H | –CH2CH(CH3)2 | H | –CH(CH3)2 | –OH | H | Ph |
| 142 | (EtO2CCH2C(O)–) | H | –CH2CH(CH3)2 | H | –CH(CH3)2 | –OH | H | Ph |
| 143 | (HO2CCH2C(O)–) | H | –CH2CH(CH3)2 | H | –CH(CH3)2 | –OH | H | Ph |
| 144 | (HOCH2CH2C(O)–) | H | –CH2CH(CH3)2 | H | –CH(CH3)2 | –OH | H | Ph |
| 145 | (EtO2CCH2CH2C(O)–) | H | –CH2CH(CH3)2 | H | –CH(CH3)2 | –OH | H | Ph |

TABLE 1-continued

| # | R1 | | R2 | | R3 | R4 | Ar |
|---|---|---|---|---|---|---|---|
| 146 | C(=O)CH₂CH₂CH₂C(=O)OH | H | —CH₂CH(CH₃)₂ | H | —CH(CH₃)₂ | H | H | phenyl |
| 147 | C(=O)CH₂—O—cyclohexyl | H | —CH₂CH(CH₃)₂ | H | —CH(CH₃)₂ | —OH | H | phenyl |
| 148 | C(=O)CH₂—O—phenyl | H | —CH₂CH(CH₃)₂ | H | —CH(CH₃)₂ | —OH | H | phenyl |
| 149 | C(=O)CH₂—O—(2-F-phenyl) | H | —CH₂CH(CH₃)₂ | H | —CH(CH₃)₂ | —OH | H | phenyl |
| 150 | C(=O)CH₂—O—(3-F-phenyl) | H | —CH₂CH(CH₃)₂ | H | —CH(CH₃)₂ | —OH | H | phenyl |

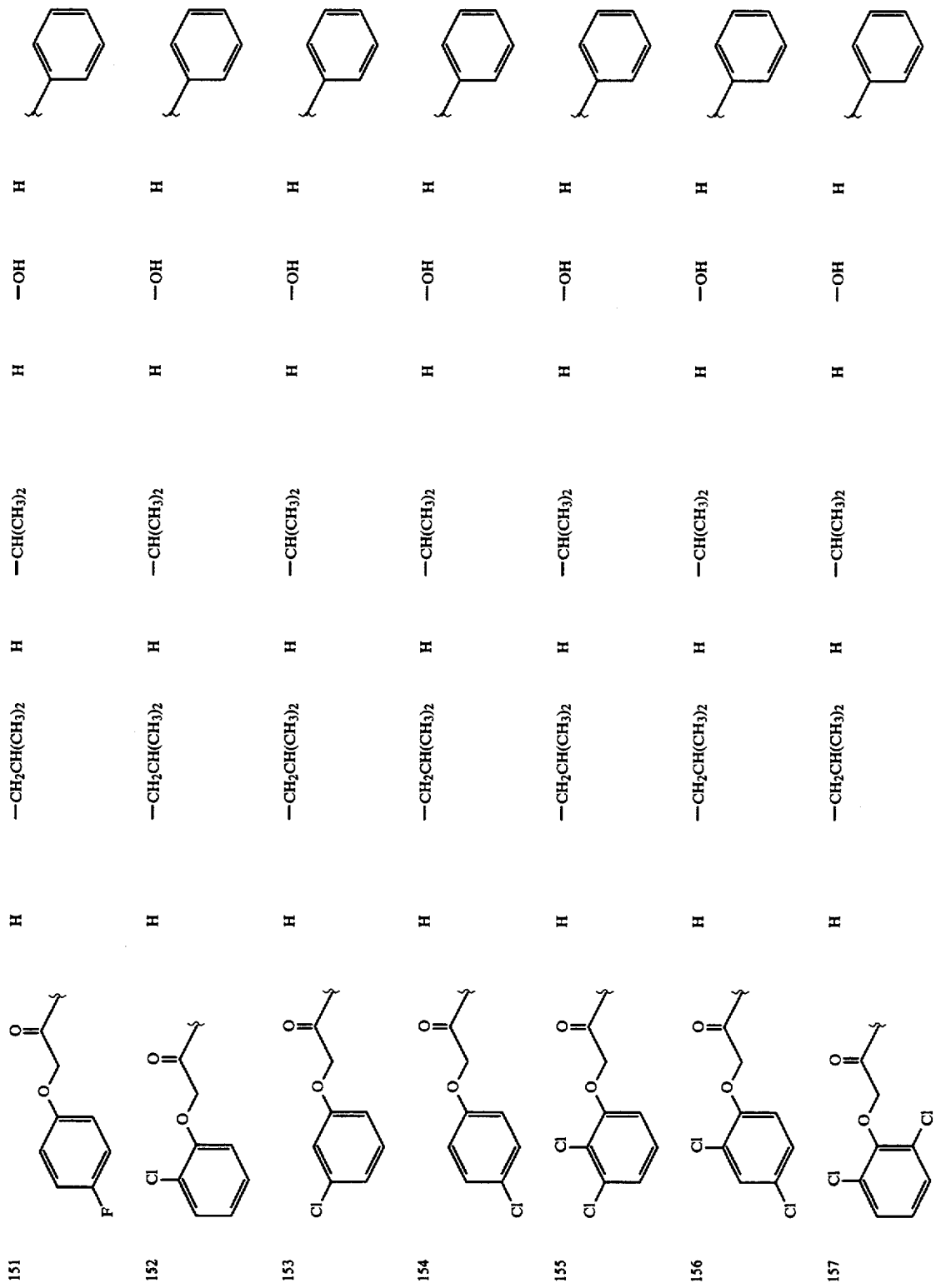

-continued

| # | Ar | R | R' | R'' | R''' | R'''' |
|---|---|---|---|---|---|---|
| 158 | Ph | H | —OH | H | —CH(CH₃)₂ | H | —CH₂CH(CH₃)₂ | H | —CH₂—C(=O)—O—(2-CH₃-C₆H₄) |
| 159 | Ph | H | —OH | H | —CH(CH₃)₂ | H | —CH₂CH(CH₃)₂ | H | —CH₂—C(=O)—O—(3-CH₃-C₆H₄) |
| 160 | Ph | H | —OH | H | —CH(CH₃)₂ | H | —CH₂CH(CH₃)₂ | H | —CH₂—C(=O)—O—(4-CH₃-C₆H₄) |
| 161 | Ph | H | —OH | H | —CH(CH₃)₂ | H | —CH₂CH(CH₃)₂ | H | —CH₂—C(=O)—O—(2-OCH₃-C₆H₄) |
| 162 | Ph | H | —OH | H | —CH(CH₃)₂ | H | —CH₂CH(CH₃)₂ | H | —CH₂—C(=O)—O—(3-OCH₃-C₆H₄) |
| 163 | Ph | H | —OH | H | —CH(CH₃)₂ | H | —CH₂CH(CH₃)₂ | H | —CH₂—C(=O)—O—(4-OCH₃-C₆H₄) |
| 164 | Ph | H | —OH | H | —CH(CH₃)₂ | H | —CH₂CH(CH₃)₂ | H | —CH₂—C(=O)—O—(2-naphthyl) |

-continued

| | 165 | 166 | 167 | 168 | 169 | 170 | 171 |
|---|---|---|---|---|---|---|---|
| Ar | Ph | Ph | Ph | Ph | Ph | Ph | Ph |
| R1 | H | H | H | H | H | H | H |
| R2 | —OH | —OH | —OH | —OH | —OH | —OH | —OH |
| R3 | H | H | H | H | H | H | H |
| R4 | —CH(CH3)2 | —CH(CH3)2 | —CH(CH3)2 | —CH(CH3)2 | —CH(CH3)2 | —CH(CH3)2 | —CH(CH3)2 |
| R5 | H | H | H | H | H | H | H |
| R6 | —CH2CH(CH3)2 | —CH2CH(CH3)2 | —CH2CH(CH3)2 | —CH2CH(CH3)2 | —CH2CH(CH3)2 | —CH2CH(CH3)2 | —CH2CH(CH3)2 |
| R7 | H | H | H | H | H | H | H |
| X | —C(O)CH2O-(2-naphthyl) | —C(O)CH2OCH2Ph | —C(O)CH2CH2OPh | —C(O)CH2SPh | —C(O)CH2CH2SPh | —C(O)CH2CH2S(O2)Ph | —C(O)Ph |

-continued
| | | | | | | |
|---|---|---|---|---|---|---|
| 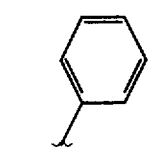 | 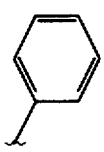 | 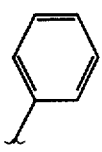 | 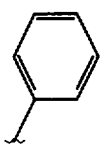 | 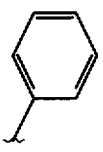 | 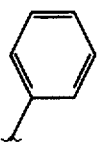 | 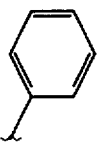 |
| H | H | H | H | H | H | H |
| —OH | —OH | —OH | —OH | —OH | —OH | —OH |
| H | H | H | H | H | H | H |
| —CH(CH$_3$)$_2$ | —CH(CH$_3$)$_2$ | —CH(CH$_3$)$_2$ | —CH(CH$_3$)$_2$ | —CH(CH$_3$)$_2$ | —CH(CH$_3$)$_2$ | —CH(CH$_3$)$_2$ |
| H | H | H | H | H | H | H |
| —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ |
| H | H | H | H | H | H | H |
| 2-F-C$_6$H$_4$-C(O)- | 3-F-C$_6$H$_4$-C(O)- | 4-F-C$_6$H$_4$-C(O)- | 2,6-F$_2$-C$_6$H$_3$-C(O)- | 2,3-F$_2$-C$_6$H$_3$-C(O)- | 2,4-F$_2$-C$_6$H$_3$-C(O)- | 2-Cl-C$_6$H$_4$-C(O)- |
| 172 | 173 | 174 | 175 | 176 | 177 | 178 |

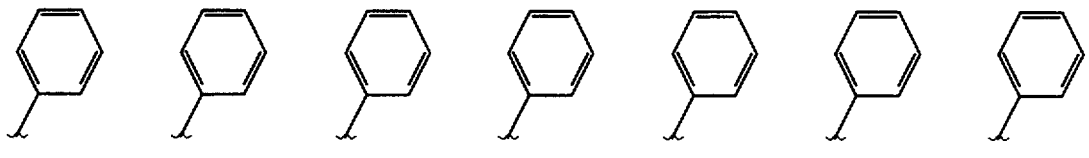

| # | | | | | | | |
|---|---|---|---|---|---|---|---|
| 186 | Ph | H | —OH | H | —CH(CH₃)₂ | H | —CH₂CH(CH₃)₂ | H | 4-CH₃-C₆H₄-C(=O)— |
| 187 | Ph | H | —OH | H | —CH(CH₃)₂ | H | —CH₂CH(CH₃)₂ | H | 2-CH₃-4-Cl-C₆H₃-C(=O)— |
| 188 | Ph | H | —OH | H | —CH(CH₃)₂ | H | —CH₂CH(CH₃)₂ | H | 2-CH₃O-C₆H₄-C(=O)— |
| 189 | Ph | H | —OH | H | —CH(CH₃)₂ | H | —CH₂CH(CH₃)₂ | H | 3-CH₃O-C₆H₄-C(=O)— |
| 190 | Ph | H | —OH | H | —CH(CH₃)₂ | H | —CH₂CH(CH₃)₂ | H | 4-CH₃O-C₆H₄-C(=O)— |
| 191 | Ph | H | —OH | H | —CH(CH₃)₂ | H | —CH₂CH(CH₃)₂ | H | 4-CH₃O-C(=O)-C₆H₄-C(=O)— |
| 192 | Ph | H | —OH | H | —CH(CH₃)₂ | H | —CH₂CH(CH₃)₂ | H | 4-HOOC-C₆H₄-C(=O)— |

-continued

| | | | | | | | |
|---|---|---|---|---|---|---|---|
| | Ph | Ph | Ph | Ph | Ph | Ph | Ph |
| | H | H | H | H | H | H | H |
| | —OH | —OH | —OH | —OH | —OH | —OH | —OH |
| | H | H | H | H | H | H | H |
| | —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ |
| | H | H | H | H | H | H | H |
| | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| | H | H | H | H | H | H | H |
| | (2-tetrahydrofuryl C=O) | (3-tetrahydrofuryl C=O) | (4-piperidyl C=O) | (N-acetyl-4-piperidyl C=O) | (2-furyl C=O) | (5-chloro-2-furyl C=O) | (3-furyl C=O) |
| | 193 | 194 | 195 | 196 | 197 | 198 | 199 |

| | | | | | | | |
|---|---|---|---|---|---|---|---|
| -continued | Ph | Ph | Ph | Ph | Ph | Ph | Ph |
| | H | H | H | H | H | H | H |
| | —OH | —OH | —OH | —OH | —OH | —OH | —OH |
| | H | H | H | H | H | H | H |
| | —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ |
| | H | H | H | H | H | H | H |
| | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| | H | H | H | H | H | H | H |
| | 2-thienoyl | 3-thienoyl | 1H-pyrazol-3-yl carbonyl | 1,3-dimethylpyrazol-5-yl carbonyl | 1H-imidazol-5-yl carbonyl | pyridin-2-yl carbonyl | pyridin-2-yl carbonyl N-oxide |
| | 200 | 201 | 202 | 203 | 204 | 205 | 206 |

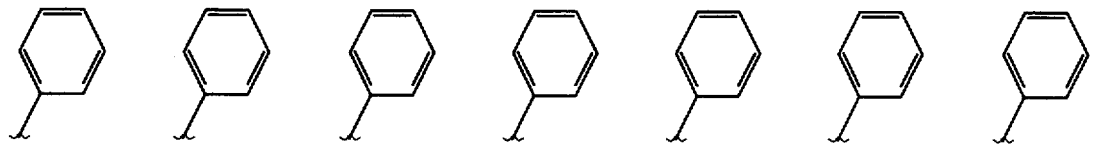

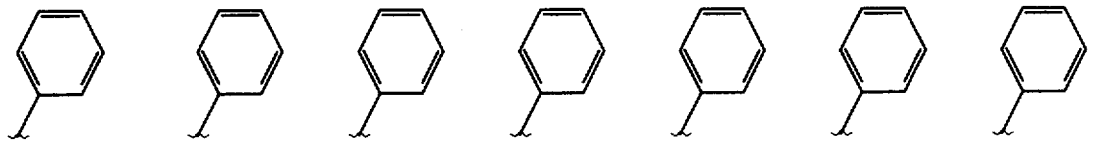

-continued
| | | | | | | | |
|---|---|---|---|---|---|---|---|
| 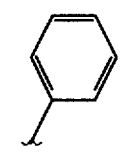 | 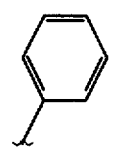 | 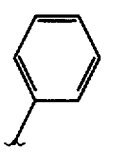 | 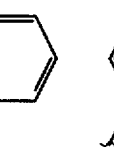 | 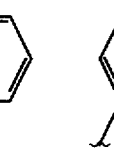 | 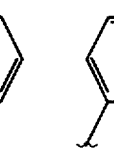 | 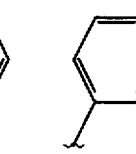 |  |
| H | H | H | H | H | H | H | H |
| —OH | —OH | —OH | —OH | —OH | —OH | —OH | —OH |
| H | H | H | H | H | H | H | H |
| —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ |
| H | H | H | H | H | H | H | H |
| —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| H | H | H | H | H | H | H | H |
| 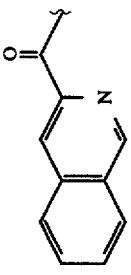 | 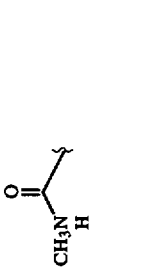 | 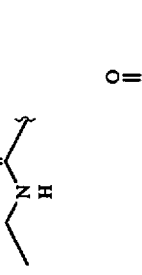 | 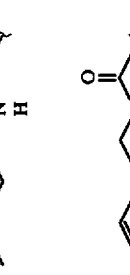 | 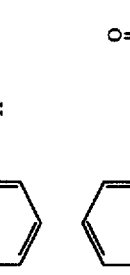 | 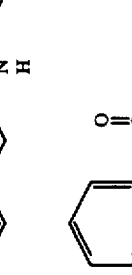 | 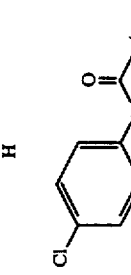 | 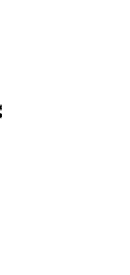 |
| 221 | 222 | 223 | 224 | 225 | 226 | 227 | 228 |

| | 229 | 230 | 231 | 232 | 233 | 234 | 235 | 236 |
|---|---|---|---|---|---|---|---|---|
| Ar | Ph | Ph | Ph | Ph | Ph | Ph | Ph | Ph |
|  | H | H | H | H | H | H | H | H |
|  | —OH | —OH | —OH | —OH | —OH | —OH | —OH | —OH |
|  | H | H | H | H | H | H | H | H |
|  | —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ |
|  | H | H | H | H | H | H | H | H |
|  | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
|  | H | H | H | H | H | H | H | H |
|  | 4-CH₃-C₆H₄-NHC(O)- | CH₃SO₂- | CH₃CH₂SO₂- | CH₃(CH₂)₂SO₂- | CH₃(CH₂)₅SO₂- | CH₃(CH₂)₁₀SO₂- | (CH₃)₃C-SO₂- | cyclohexyl-SO₂- |

| | 237 | 238 | 239 | 240 | 241 | 242 | 243 |
|---|---|---|---|---|---|---|---|
| Ar | Ph | Ph | Ph | Ph | Ph | Ph | Ph |
| | H | H | H | H | H | =O | H |
| | —OH | —OH | —OH | —OH | —OC(=O)OCH₃ | | —OH |
| | H | H | H | H | H | H | H |
| | —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ |
| | H | H | H | H | H | H | H |
| | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| | H | H | H | H | H | H | H |
| R | —SO₂CH₂Ph | —SO₂CH₂CH₂Ph | —SO₂Ph | —SO₂Ph | —SO₂Ph | —SO₂Ph | —SO₂(2-F-C₆H₄) |

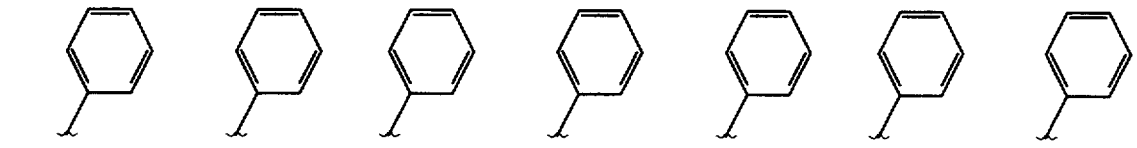
| | | | | | | |
|---|---|---|---|---|---|---|
| H | H | H | H | H | H | H |
| —OH | —OH | —OH | —OH | —OH | —OH | —OH |
| H | H | H | H | H | H | H |
| —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ |
| H | H | H | H | H | H | H |
| —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| H | H | H | H | H | H | H |
| 244 | 245 | 246 | 247 | 248 | 249 | 250 |

-continued

| | 251 | 252 | 253 | 254 | 255 | 256 | 257 | 258 |
|---|---|---|---|---|---|---|---|---|
| Ar | Ph | Ph | Ph | Ph | Ph | Ph | Ph | Ph |
| | H | H | H | H | H | H | H | H |
| | —OH | —OH | —OH | —OH | —OH | —OH | —OH | —OH |
| | H | H | H | H | H | H | H | H |
| | —CH(CH$_3$)$_2$ | —CH(CH$_3$)$_2$ | —CH(CH$_3$)$_2$ | —CH(CH$_3$)$_2$ | —CH(CH$_3$)$_2$ | —CH(CH$_3$)$_2$ | —CH(CH$_3$)$_2$ | —CH(CH$_3$)$_2$ |
| | H | H | H | H | H | H | H | H |
| | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ |
| | H | H | H | H | H | H | H | H |
| R | 4-CH$_3$-C$_6$H$_4$-SO$_2$- | 2-CF$_3$-C$_6$H$_4$-SO$_2$- | 3-CF$_3$-C$_6$H$_4$-SO$_2$- | 4-CF$_3$-C$_6$H$_4$-SO$_2$- | 2-CH$_3$O-C$_6$H$_4$-SO$_2$- | 3-CH$_3$O-C$_6$H$_4$-SO$_2$- | 4-CH$_3$O-C$_6$H$_4$-SO$_2$- | 4-iPrO-C$_6$H$_4$-SO$_2$- |

| | | | | | | |
|---|---|---|---|---|---|---|
| 259 | naphthalen-1-ylsulfonyl | —CH₂CH(CH₃)₂ | H | —CH(CH₃)₂ | H | —OH | H | Ph |
| 260 | naphthalen-2-ylsulfonyl | —CH₂CH(CH₃)₂ | H | —CH(CH₃)₂ | H | —OH | H | Ph |
| 261 | pyridin-2-ylsulfonyl | —CH₂CH(CH₃)₂ | H | —CH(CH₃)₂ | H | —OH | H | Ph |
| 262 | pyridin-3-ylsulfonyl | —CH₂CH(CH₃)₂ | H | —CH(CH₃)₂ | H | —OH | H | Ph |
| 263 | pyridin-4-ylsulfonyl | —CH₂CH(CH₃)₂ | H | —CH(CH₃)₂ | H | —OH | H | Ph |
| 264 | quinolin-5-ylsulfonyl | —CH₂CH(CH₃)₂ | H | —CH(CH₃)₂ | H | —OH | H | Ph |

-continued
| | | | | | | |
|---|---|---|---|---|---|---|
| 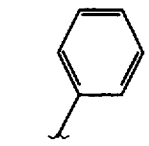 | 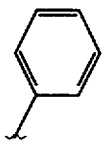 | 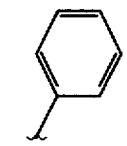 | 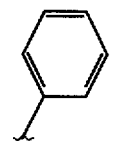 | 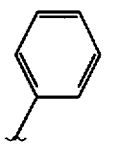 | 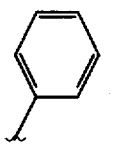 |  |
| H | H | H | H | H | H | H |
| —OH | —OH | —OH | —OH | —OH | —OH | —OH |
| H | H | H | H | H | H | H |
| —CH(CH$_3$)$_2$ | —CH(CH$_3$)$_2$ | —CH(CH$_3$)$_2$ | —CH(CH$_3$)$_2$ | —CH(CH$_3$)$_2$ | —CH(CH$_3$)$_2$ | —CH(CH$_3$)$_2$ |
| H | H | H | H | H | H | H |
| —CH$_2$CH(CH$_3$)$_2$ | —CH$_2$CH(CH$_3$)$_2$ | —CH$_2$CH$_2$CH$_2$CH$_3$ | —CH$_2$CH$_2$CH$_2$CH$_3$ | CH$_3$<br>\|<br>—CHCH$_2$CH$_3$ |  | 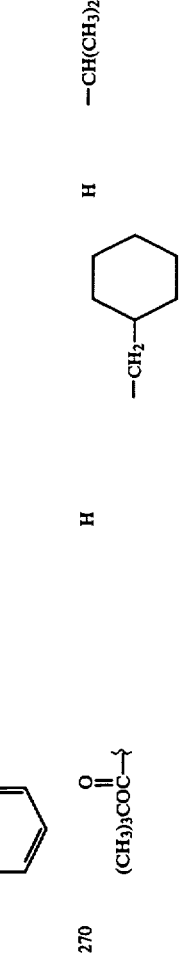 |
| H | H | H | H | H | H | H |
| 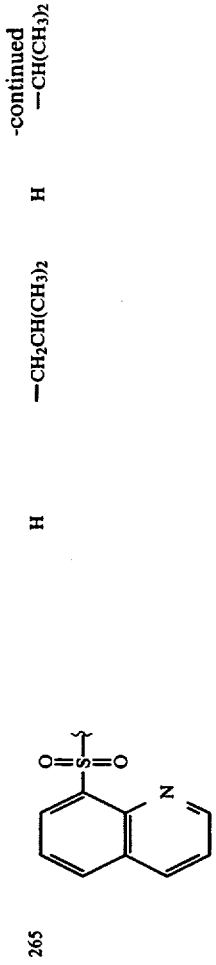 | 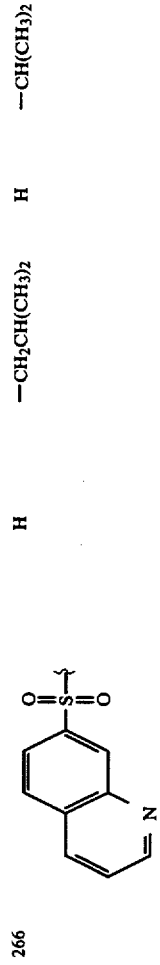 |  |  |  | 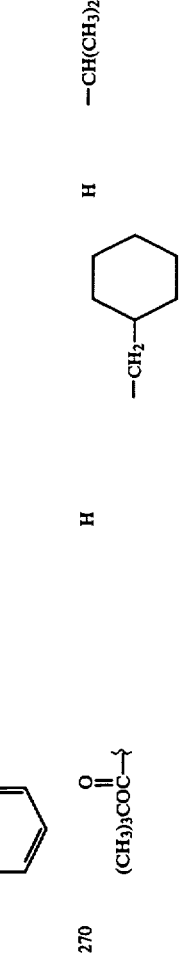 |  |
| 265 | 266 | 267 | 268 | 269 | 270 | 271 |

-continued

| 272 | 273 | 274 | 275 | 276 | 277 | 278 |
|---|---|---|---|---|---|---|
| Ph | Ph | Ph | Ph | Ph | Ph | Ph |
| H | H | H | H | H | H | H |
| —OH | —OH | —OH | —OH | —OH | —OH | —OH |
| H | H | H | H | H | H | H |
| —CH(CH₃)₂ | —CH(CH₃)₂ | —CH(CH₃)₂ | —CH(CH₃)₂ | —CH(CH₃)₂ | —CH₂CH(CH₃)₂ | —CH₂CH(CH₃)₂ |
| H | H | H | H | H | H | H |
| —CH₂-Cyclohexyl | —CH₂-Cyclohexyl | —CH₂-Cyclohexyl | —CH₂-Ph | —CH₂-Ph | —CH₂CH(CH₃)₂ | —CH₂CH(CH₃)₂ |
| H | H | H | H | H | H | H |
| H | —C(=O)CH₂-O-Ph | —S(=O)₂-Ph | —C(=O)-O-CH₂-Cyclohexyl | —C(=O)-O-CH₂-Ph | —C(=O)-O-CH₂-Cyclohexyl | —C(=O)-O-CH₂-Ph |

-continued

| | 279 | 280 | 281 | 282 | 283 | 284 | 285 |
|---|---|---|---|---|---|---|---|
| | Ph | Ph | Ph | Ph | Ph | Ph | Ph |
| | H | H | H | H | H | H | H |
| | —OH | —OH | —OH | —OH | —OH | —OH | —OH |
| | H | H | H | H | H | H | H |
| | —CH₂CH₂CH₂CH₃ | —CH₂CH₂CH₂CH₃ | —CH₂CH₂CH₂CH₃ | —CH₂CH₂CH₂CH₃ | —CH(CH₃)CH₂CH₃ | —CH(CH₃)CH₂CH₃ | —CH₂-cyclohexyl |
| | H | H | H | H | H | H | H |
| | —CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| | H | H | H | H | H | H | H |
| | —C(O)OCH₂Ph | —C(O)OCH₂-cyclohexyl | —C(O)OCH₂Ph | —C(O)OCH₂-(2-pyridyl) | —C(O)OCH₂-cyclohexyl | —C(O)OCH₂Ph | —C(O)OCH₂-cyclohexyl |

| No. | R1 | R2 | R3 | R4 | R5 | R6 | R7 | R8 |
|---|---|---|---|---|---|---|---|---|
| 286 | Ph | H | —OH | H | —CH₂(cyclohexyl) | H | —CH₂CH(CH₃)₂ | H, —C(=O)O—CH₂—Ph |
| 287 | Ph | H | —OH | H | —CH₂Ph | H | —CH₂CH(CH₃)₂ | H, —C(=O)O—CH₂(cyclohexyl) |
| 288 | Ph | H | —OH | H | —CH₂Ph | H | —CH₂CH(CH₃)₂ | H, —C(=O)O—CH₂(2-pyridyl) |
| 289 | Ph | H | —OH | —CH₃ | —CH₃ | H | —CH₂CH(CH₃)₂ | H, —C(=O)O—CH₂(cyclohexyl) |
| 290 | Ph | H | —OH | —CH₃ | —CH₃ | H | —CH₂CH(CH₃)₂ | H, —C(=O)—C(CH₃)₃ |
| 291 | Ph | H | —OH | —CH₃ | —CH₃ | H | —CH₂CH(CH₃)₂ | H, —C(=O)O—CH₂—Ph |
| 292 | Ph | H | —OH | —CH₃ | —CH₃ | H | —CH₂CH(CH₃)₂ | H, —C(=O)O—CH₂(2-pyridyl) |

-continued

| | 293 | 294 | 295 | 296 | 297 | 298 | 299 | 300 |
|---|---|---|---|---|---|---|---|---|
| Ar | Ph | Ph | Ph | Ph | Ph | Ph | Ph | Ph |
| R1 | H | H | H | H | H | H | =O | =O |
| R2 | —OH | —OH | —OH | —OH | —OH | —OH | | |
| R3 | —CH₃ | —CH₃ | —CH₃ | —CH₃ | —CH₃ | —CH₃ | —CH₃ | —CH₃ |
| R4 | —CH₃ | —CH₃ | —CH₃ | —CH₃ | —CH₃ | —CH₃ | —CH₃ | —CH₃ |
| R5 | H | H | H | H | H | H | H | H |
| R6 | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂SCH₃ / —CH₂CH(CH₃)₂ | —CH₂CH(CH₃)₂ | —CH₂CH(CH₃)₂ |
| R7 | H | H | H | H | H | H | H | H |
| R8 | 4-pyridyl-CH₂-OC(O)- | PhOCH₂C(O)- | PhC(O)- | PhSO₂- | PhSO₂- | cyclohexyl-CH₂-OC(O)- | PhOCH₂C(O)- | |

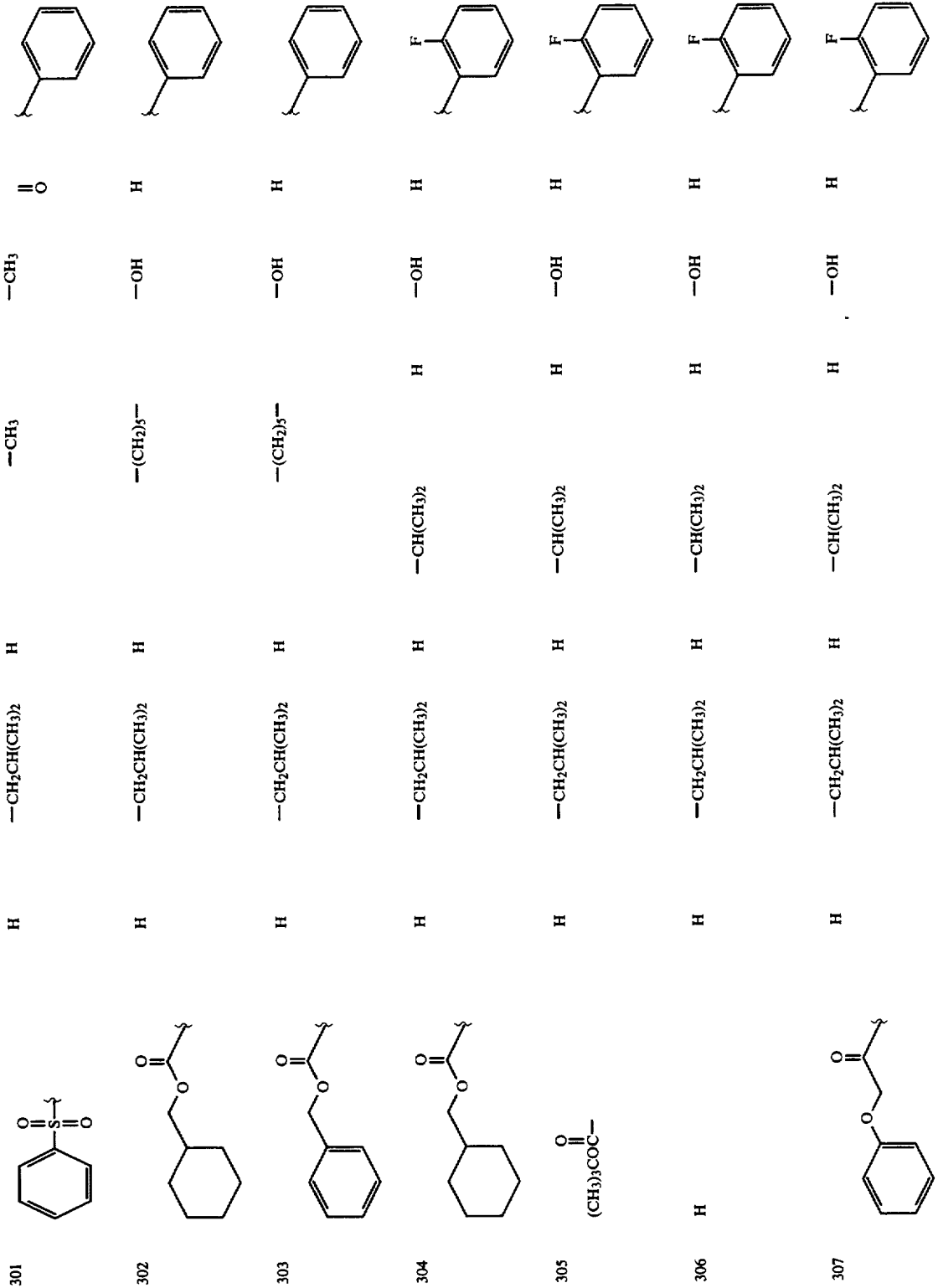

-continued

| # | Aryl | | | | | | | |
|---|---|---|---|---|---|---|---|---|
| 308 | 2-F-C6H4 | H | —OH | H | —CH(CH3)2 | —CH2CH(CH3)2 | H | —SO2C6H5 |
| 309 | 4-F-C6H4 | H | —OH | H | —CH(CH3)2 | —CH2CH(CH3)2 | H | —C(O)OCH2-cyclohexyl |
| 310 | 4-F-C6H4 | H | —OH | H | —CH(CH3)2 | —CH2CH(CH3)2 | H | —C(O)OCH2C6H5 |
| 311 | 4-F-C6H4 | H | —OH | H | —CH(CH3)2 | —CH2CH(CH3)2 | H | —C(O)OCH2-cyclohexyl |
| 312 | 4-F-C6H4 | H | —OH | H | —CH(CH3)2 | —CH2CH(CH3)2 | H | (CH3)3COC(O)— |
| 313 | 4-F-C6H4 | H | —OH | H | —CH(CH3)2 | —CH2CH(CH3)2 | H | —C(O)OCH2C6H5 |
| 314 | 4-F-C6H4 | H | —OH | H | —CH(CH3)2 | —CH2CH(CH3)2 | H | H |

-continued
| | | | | | | | |
|---|---|---|---|---|---|---|---|
| | 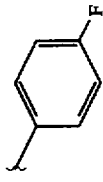 | 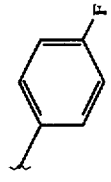 | 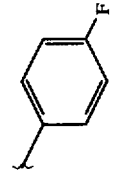 | 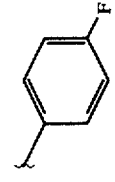 | 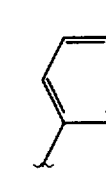 | 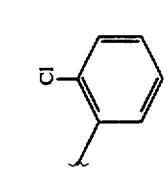 | 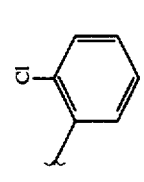 |
| | H | H | H | H | H | H | H |
| | —OH | —OH | —OH | —OH | —OH | —OH | —OH |
| | H | H | H | H | H | H | H |
| | —CH(CH₃)₂ | —CH(CH₃)₂ | —CH(CH₃)₂ | —CH₂CH₂CH₂CH₃ | —CH₂CH₂CH₂CH₃ | —CH₃ | —CH(CH₃)₂ |
| | H | H | H | H | H | H | H |
| | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂-C₆H₅ | —CH₂CH(CH₃)₂ |
| | H | H | H | H | H | H | H |
| | ![phenoxyacetyl] | ![furoyl] | ![phenylsulfonyl] | ![cyclohexylmethoxycarbonyl] | ![benzyloxycarbonyl] | ![benzyloxycarbonyl] | ![benzyloxycarbonyl] |
| | 315 | 316 | 317 | 318 | 319 | 320 | 321 |

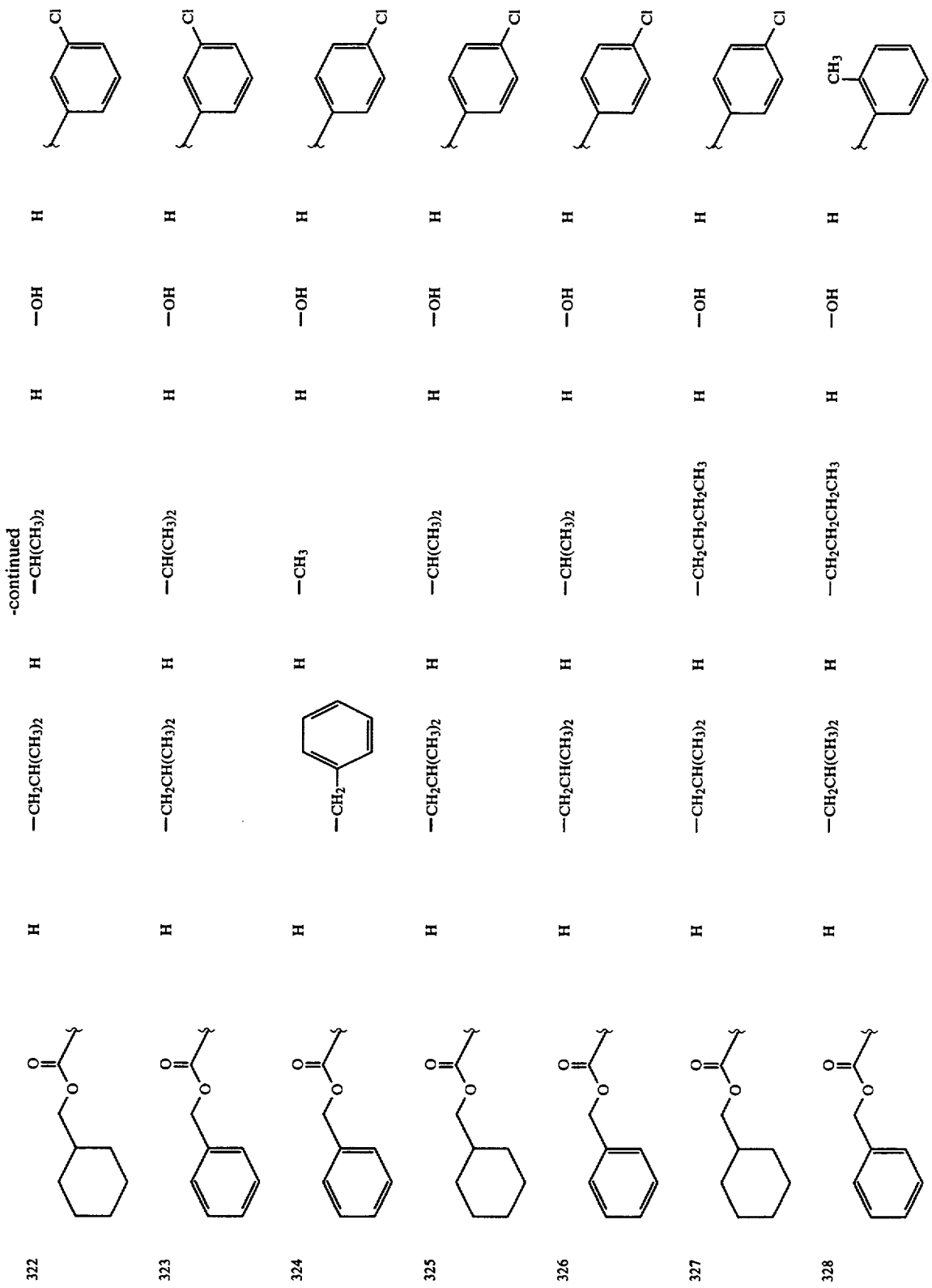

-continued

| No. | Ar | R1 | R2 | R3 | R4 | R5 | R6 |
|---|---|---|---|---|---|---|---|
| 329 | 2-CH₃-C₆H₄ | H | —OH | H | —CH₂CH₂CH₃ | H | —CH₂CH(CH₃)₂ | H | —C(O)OCH₂C₆H₅ |
| 330 | 3-CH₃-C₆H₄ | H | —OH | H | —CH₂CH₂CH₃ | H | —CH₂CH(CH₃)₂ | H | —C(O)OCH₂-cyclohexyl |
| 331 | 3-CH₃-C₆H₄ | H | —OH | H | —CH₂CH₂CH₃ | H | —CH₂CH(CH₃)₂ | H | —C(O)OCH₂C₆H₅ |
| 332 | 4-CH₃-C₆H₄ | H | —OH | H | —CH(CH₃)₂ | H | —CH₂CH(CH₃)₂ | H | (CH₃)₃COC(O)— |
| 333 | 4-CH₃-C₆H₄ | H | —OH | H | —CH(CH₃)₂ | H | —CH₂CH(CH₃)₂ | H | H |
| 334 | 4-CH₃-C₆H₄ | H | —OH | H | —CH(CH₃)₂ | H | —CH₂CH(CH₃)₂ | H | —C(O)CH₂OC₆H₅ |
| 335 | 4-CH₃-C₆H₄ | H | —OH | H | —CH(CH₃)₂ | H | —CH₂CH(CH₃)₂ | H | —S(O)₂C₆H₅ |

| 336 | 337 | 338 | 339 | 340 | 341 | 342 |
|---|---|---|---|---|---|---|
| 4-CH₃-C₆H₄- | 2-OCH₃-C₆H₄- | 2-OCH₃-C₆H₄- | 3-OCH₃-C₆H₄- | 3-OCH₃-C₆H₄- | 3-F-4-OCH₃-C₆H₃- | 3-F-4-OCH₃-C₆H₃- |
| H | H | H | H | H | H | H |
| —OH | —OH | —OH | —OH | —OH | —OH | —OH |
| H | H | H | H | H | H | H |
| —CH₂CH₂CH₂CH₃ | —CH(CH₃)₂ | —CH(CH₃)₂ | —CH(CH₃)₂ | —CH(CH₃)₂ | —CH₃ | —CH₂CH(CH₃)₂ |
| H | H | H | H | H | H | H |
| —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂-C₆H₅ | —CH₂CH(CH₃)₂ |
| H | H | H | H | H | H | H |
| —C(O)OCH₂-cyclohexyl | —C(O)OCH₂-cyclohexyl | —C(O)OCH₂-C₆H₅ | —C(O)OCH₂-cyclohexyl | —C(O)OCH₂-C₆H₅ | —C(O)OCH₂-C₆H₅ | —C(O)OCH₂-cyclohexyl |

-continued

| # | Ar | R1 | R2 | R3 | R4 | R5 | R6 | Ester |
|---|---|---|---|---|---|---|---|---|
| 343 | 3-F-4-OCH₃-phenyl | H | —OH | H | —CH₂CH(CH₃)₂ | H | —CH₂CH(CH₃)₂ | H | —C(O)O-CH₂-phenyl |
| 344 | 3,4-di-OCH₃-phenyl | H | —OH | H | —CH(CH₃)₂ | H | —CH₂CH(CH₃)₂ | H | —C(O)O-CH₂-cyclohexyl |
| 345 | 3,4-di-OCH₃-phenyl | H | —OH | H | —CH(CH₃)₂ | H | —CH₂CH(CH₃)₂ | H | —C(O)O-CH₂-phenyl |
| 346 | 2-naphthyl | H | —OH | H | —CH₃ | H | —CH₂-phenyl | H | —C(O)O-CH₂-cyclohexyl |
| 347 | 2-naphthyl | H | —OH | H | —CH₃ | H | —CH₂-phenyl | H | —C(O)O-CH₂-phenyl |
| 348 | 2-naphthyl | H | —OH | H | —CH(CH₃)₂ | H | —CH₂CH(CH₃)₂ | H | —C(O)O-CH₂-cyclohexyl |
| 349 | 2-naphthyl | H | —OH | H | —CH(CH₃)₂ | H | —CH₂CH(CH₃)₂ | H | —C(O)O-CH₂-phenyl |

-continued
| | | | | | |
|---|---|---|---|---|---|
| 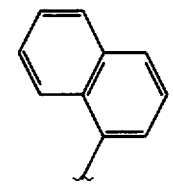 | 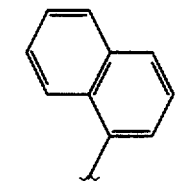 | 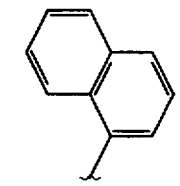 | 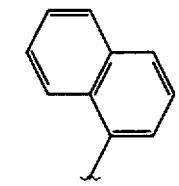 |  |  |
| H | H | H | H | H | H |
| —OH | —OH | —OH | —OH | —OH | —OH |
| H | H | H | H | H | H |
| —CH$_3$ | —CH$_3$ | —CH(CH$_3$)$_2$ | —CH(CH$_3$)$_2$ | —CH$_3$ | —CH$_3$ |
| H | H | H | H | H | H |
| 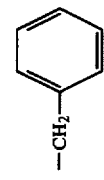 | 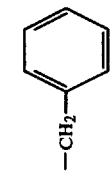 | —CH$_2$CH(CH$_3$)$_2$ | —CH$_2$CH(CH$_3$)$_2$ | 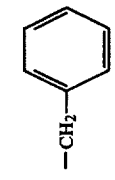 | 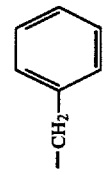 |
| H | H | H | H | H | H |
| 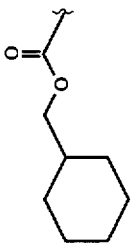 | 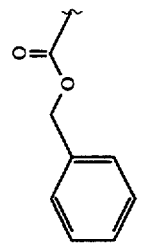 | 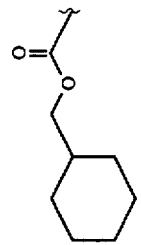 | 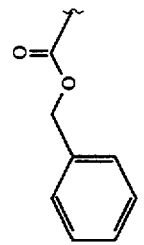 | 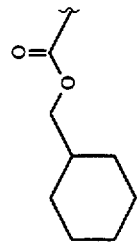 | 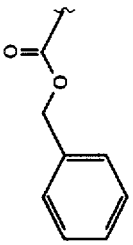 |
| 350 | 351 | 352 | 353 | 354 | 355 |

-continued

| # | Col1 | Col2 | Col3 | Col4 | Col5 | Col6 | Col7 |
|---|------|------|------|------|------|------|------|
| 356 | furyl | H | —OH | H | —CH$_3$ | H | —CH$_2$CH(CH$_3$)$_2$ | H | benzyl ester (—C(O)OCH$_2$Ph) |
| 357 | furyl | H | —OH | H | —CH(CH$_3$)$_2$ | H | —CH$_2$CH(CH$_3$)$_2$ | H | cyclohexylmethyl ester |
| 358 | furyl | H | —OH | H | —CH(CH$_3$)$_2$ | H | —CH$_2$CH(CH$_3$)$_2$ | H | (CH$_3$)$_3$COC(O)— |
| 359 | furyl | H | —OH | H | —CH(CH$_3$)$_2$ | H | —CH$_2$CH(CH$_3$)$_2$ | H | H |
| 360 | furyl | H | —OH | H | —CH(CH$_3$)$_2$ | H | —CH$_2$CH(CH$_3$)$_2$ | H | —C(O)CH$_2$OPh |
| 361 | furyl | H | —OH | H | —CH(CH$_3$)$_2$ | H | —CH$_2$CH(CH$_3$)$_2$ | H | 2-furoyl |
| 362 | furyl | H | —OH | H | —CH(CH$_3$)$_2$ | H | —CH$_2$CH(CH$_3$)$_2$ | H | PhSO$_2$— |
| 363 | furyl | H | —OH | H | —CH$_2$CH$_2$CH$_2$CH$_3$ | H | —CH$_2$CH(CH$_3$)$_2$ | H | benzyl ester |

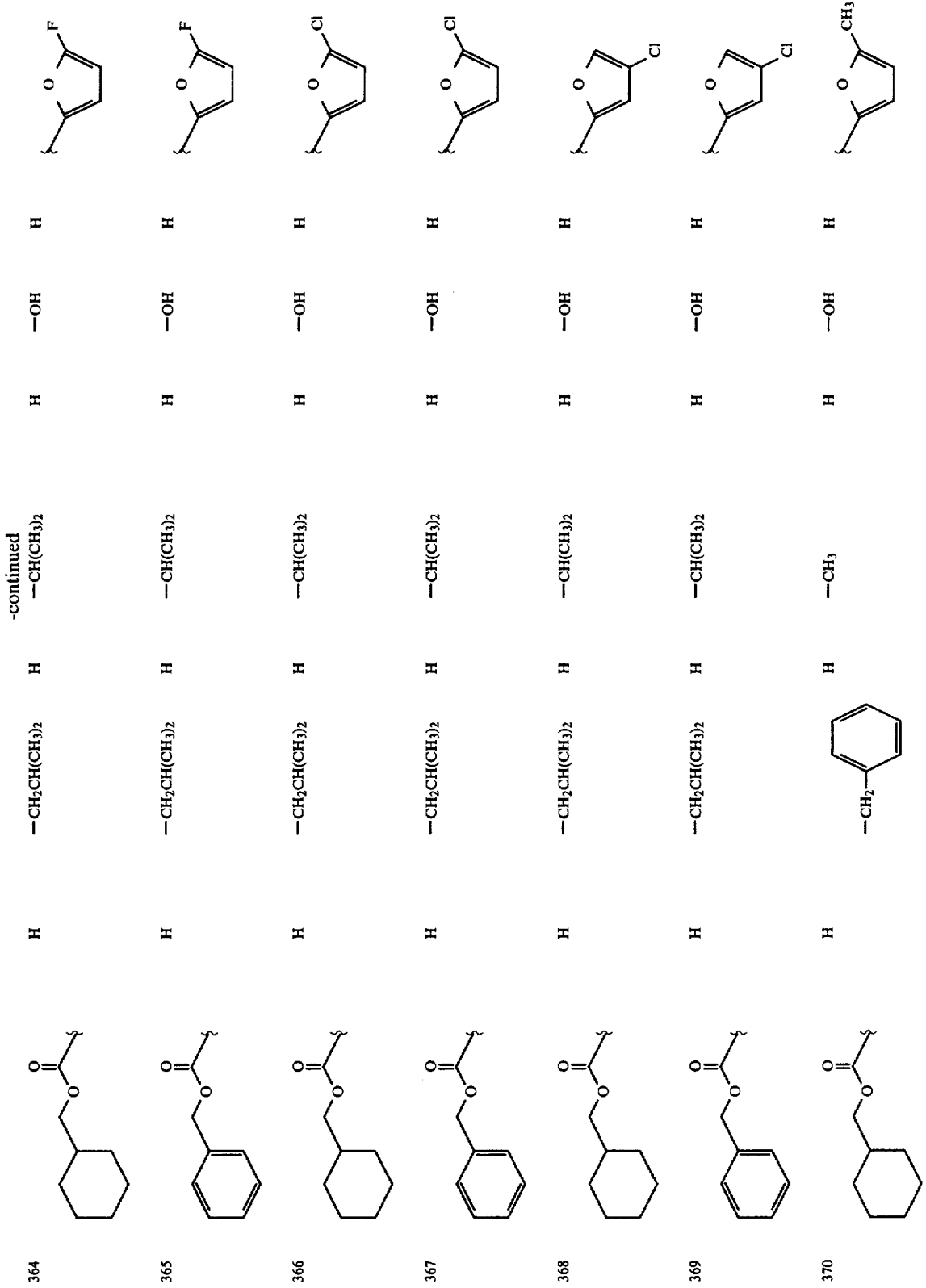

-continued

| | | | | | | |
|---|---|---|---|---|---|---|
| 5-methylfuran-2-yl | 5-methylfuran-2-yl | 5-methylfuran-2-yl | 5-methoxyfuran-2-yl | 5-methoxyfuran-2-yl | 5-(Si(CH₃)₃)furan-2-yl | 5-(Si(CH₃)₃)furan-2-yl |
| H | H | H | H | H | H | H |
| —OH | —OH | —OH | —OH | —OH | —OH | —OH |
| H | H | H | H | H | H | H |
| —CH₃ | —CH(CH₃)₂ | —CH(CH₃)₂ | —CH(CH₃)₂ | —CH(CH₃)₂ | —CH₂CH₂CH₃ | —CH₂CH₂CH₃ |
| H | H | H | H | H | H | H |
| —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| H | H | H | H | H | H | H |
| —C(=O)O–CH₂–cyclohexyl | —C(=O)O–CH₂–cyclohexyl | —C(=O)O–CH₂–phenyl | —C(=O)O–CH₂–cyclohexyl | —C(=O)O–CH₂–phenyl | —C(=O)O–CH₂–cyclohexyl | —C(=O)O–CH₂–phenyl |
| 371 | 372 | 373 | 374 | 375 | 376 | 377 |

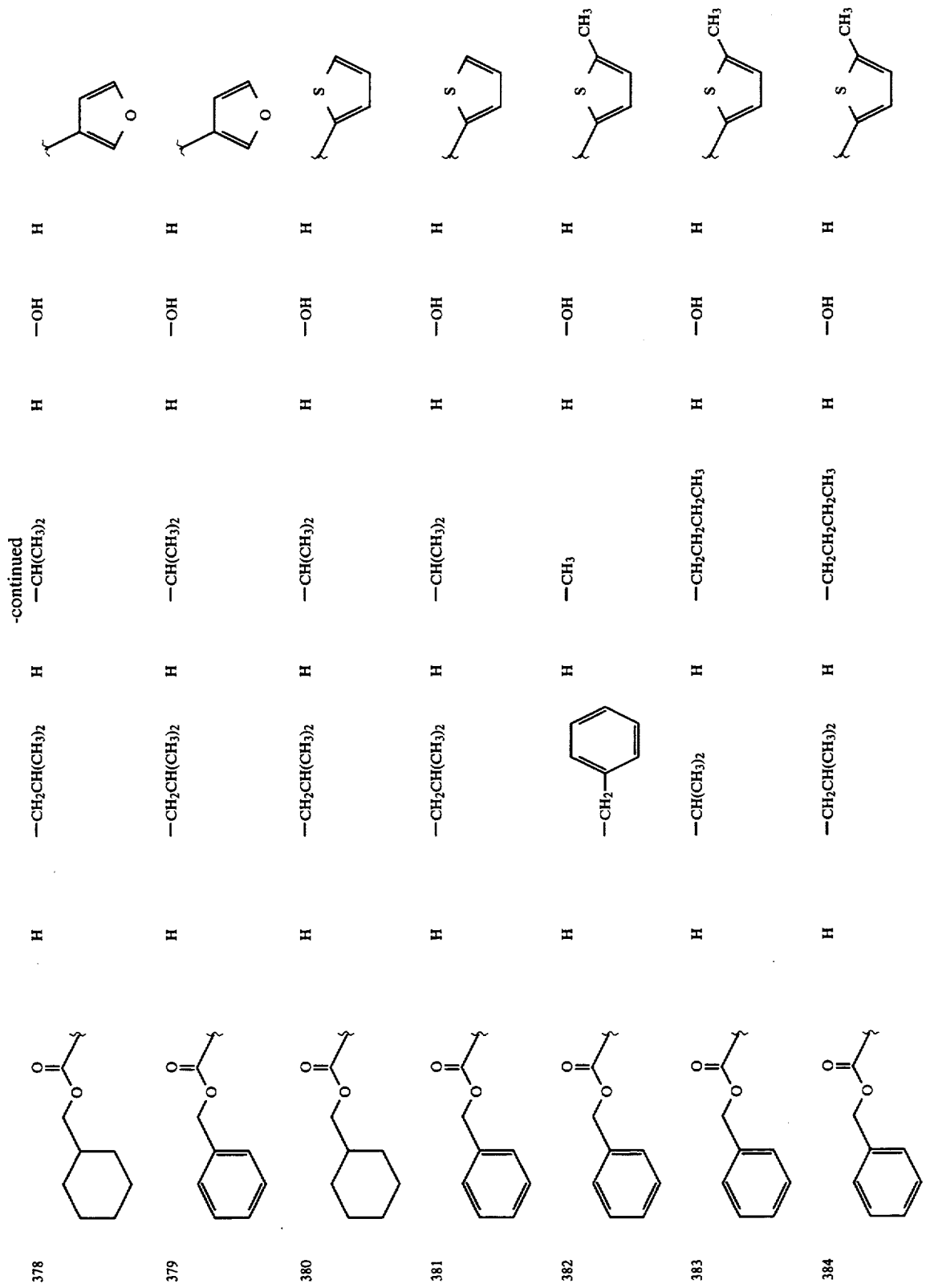

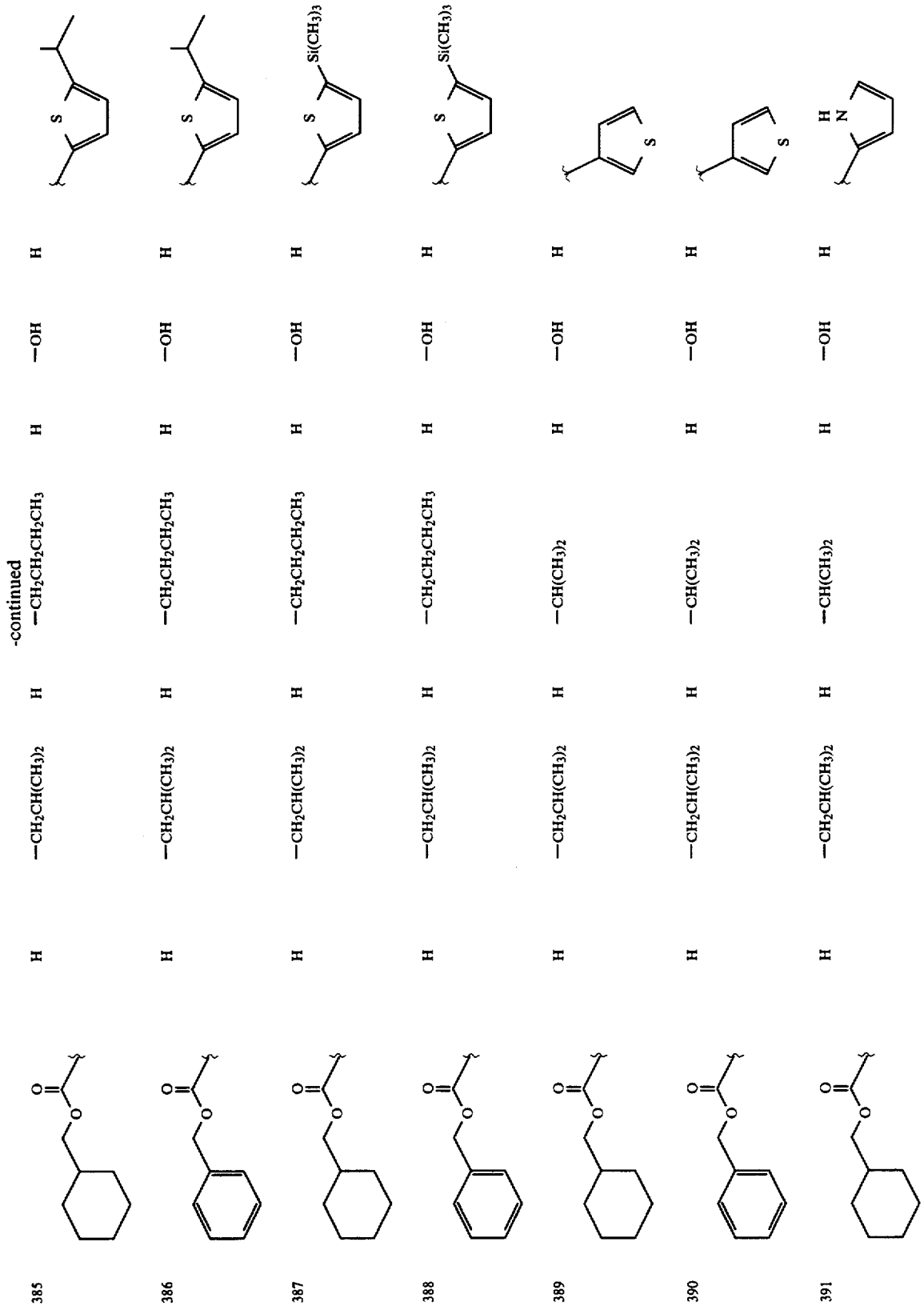

-continued

| | | | | | | |
|---|---|---|---|---|---|---|
| pyrrole (NH) | pyridin-2-yl | pyridin-2-yl | pyridin-3-yl | pyridin-3-yl | pyridin-4-yl | pyridin-4-yl |
| H | H | H | H | H | H | H |
| —OH | —OH | —OH | —OH | —OH | —OH | —OH |
| H | H | H | H | H | H | H |
| —CH(CH₃)₂ | —CH(CH₃)₂ | —CH(CH₃)₂ | —CH(CH₃)₂ | —CH(CH₃)₂ | —CH(CH₃)₂ | —CH(CH₃)₂ |
| H | H | H | H | H | H | H |
| —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ | —CH₂CH(CH₃)₂ |
| H | H | H | H | H | H | H |
| —C(O)O—CH₂—Ph | —C(O)O—CH₂—Cy | —C(O)O—CH₂—Ph | —C(O)O—CH₂—Cy | —C(O)O—CH₂—Ph | —C(O)O—CH₂—Cy | —C(O)O—CH₂—Ph |
| 392 | 393 | 394 | 395 | 396 | 397 | 398 |

-continued

| # | Ar | R1 | R2 | R3 | R4 | R5 | R6 |
|---|----|----|----|----|----|----|----|
| 399 | benzofuran-2-yl | H | —OH | H | —CH₃ | H | —CH₂-phenyl | H | cyclohexylmethyl-O-C(=O)- |
| 400 | benzofuran-2-yl | H | —OH | H | —CH₃ | H | —CH₂CH(CH₃)₂ | H | cyclohexylmethyl-O-C(=O)- |
| 401 | benzofuran-2-yl | H | —OH | H | —CH(CH₃)₂ | H | —CH₂CH(CH₃)₂ | H | cyclohexylmethyl-O-C(=O)- |
| 402 | benzofuran-2-yl | H | —OH | H | —CH(CH₃)₂ | H | —CH₂CH(CH₃)₂ | H | benzyl-O-C(=O)- |
| 403 | benzofuran-2-yl | H | —OH | H | —CH(CH₃)₂ | H | —CH₂CH(CH₃)₂ | H | (pyridin-2-yl)methyl-O-C(=O)- |
| 404 | benzothiophen-2-yl | H | —OH | H | —CH(CH₃)₂ | H | —CH₂CH(CH₃)₂ | H | cyclohexylmethyl-O-C(=O)- |
| 405 | benzothiophen-2-yl | H | —OH | H | —CH(CH₃)₂ | H | —CH₂CH(CH₃)₂ | H | benzyl-O-C(=O)- |

| No. | R1 | | R2 | | R3 | | R4 | | R5 |
|---|---|---|---|---|---|---|---|---|---|
| 406 | cyclohexyl-CH2-O-C(=O)- | H | —CH2CH(CH3)2 | H | —CH2CH2CH2CH3 | H | —OH | H | 2-quinolinyl |
| 407 | phenyl-CH2-O-C(=O)- | H | —CH2CH(CH3)2 | H | —CH2CH2CH2CH3 | H | —OH | H | 2-quinolinyl |
| 408 | cyclohexyl-CH2-O-C(=O)- | H | —CH2CH(CH3)2 | H | —CH2CH2CH2CH3 | H | —OH | H | 2-quinolinyl |
| 409 | cyclohexyl-CH2-O-C(=O)- | H | —CH2CH(CH3)2 | H | —CH3 | H | —OH | H | —CH2OH |
| 410 | cyclohexyl-CH2-O-C(=O)- | H | —CH2-phenyl | H | —CH3 | H | —OH | H | —CH2OH |
| 411 | cyclohexyl-CH2-O-C(=O)- | H | —CH2CH(CH3)2 | H | —CH(CH3)2 | H | —OH | H | —CH2OH |
| 412 | phenyl-CH2-O-C(=O)- | H | —CH2CH(CH3)2 | H | —CH(CH3)2 | H | —OH | H | —CH2OH |

-continued
| | 413 | 414 | 415 | 416 | 417 | 418 | 419 |
|---|---|---|---|---|---|---|---|
| | 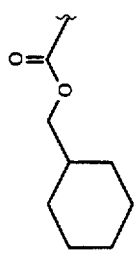 | 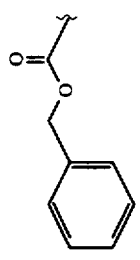 | 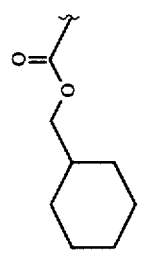 | 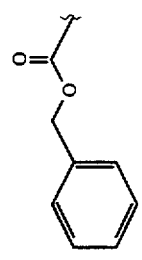 | 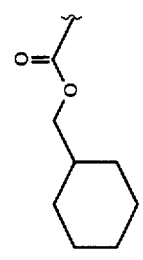 | 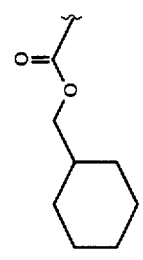 | 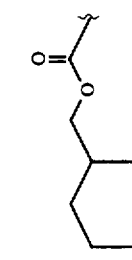 |
| | H | H | H | H | H | H | H |
| | —OH | —OH | —OH | —OH | —OH | —OH | —OH |
| | H | H | H | H | H | H | H |
| | —CH(CH$_3$)$_2$ | —CH(CH$_3$)$_2$ | —CH(CH$_3$)$_2$ | —CH(CH$_3$)$_2$ | —CH$_3$ | —CH$_3$ | —CH(CH$_3$)$_2$ |
| | H | H | H | H | H | H | H |
| | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | 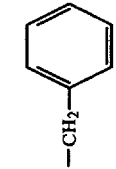 | —CH(CH$_3$)$_2$ |
| | H | H | H | H | H | H | H |

| | | | | | | |
|---|---|---|---|---|---|---|
| 420 | (CH₃)₃OC(=O)- | H | -CH₂CH(CH₃)₂ | H | -CH(CH₃)₂ | H | -OH | H | -C(CH₃)₂OH |
| 421 | cyclohexyl-CH₂-O-C(=O)- | H | -CH₂CH(CH₃)₂ | H | -CH(CH₃)₂ | H | -OH | H | -C(CH₃)₂OH |
| 422 | phenyl-CH₂-O-C(=O)- | H | -CH₂CH(CH₃)₂ | H | -CH(CH₃)₂ | H | -OH | H | -C(CH₃)₂OH |
| 423 | (2-pyridyl)-CH₂-O-C(=O)- | H | -CH₂CH(CH₃)₂ | H | -CH(CH₃)₂ | H | -OH | H | -C(CH₃)₂OH |
| 424 | H | H | -CH₂CH(CH₃)₂ | H | -CH(CH₃)₂ | H | -OH | H | -C(CH₃)₂OH |
| 425 | phenyl-CH₂-O-C(=O)- | H | -CH₂CH(CH₃)₂ | H | -CH(CH₃)₂ | H | -OH | H | -C(CH₃)₂OH |
| 426 | 2-furyl-C(=O)- | H | -CH₂CH(CH₃)₂ | H | -CH(CH₃)₂ | H | -OH | H | -C(CH₃)₂OH |
| 427 | phenyl-SO₂- | H | -CH₂CH(CH₃)₂ | H | -CH(CH₃)₂ | H | -OH | H | -C(CH₃)₂OH |

-continued

| | | | | | | | |
|---|---|---|---|---|---|---|---|
| 428 | 429 | 430 | 431 | 432 | 433 | 434 |
|  |  |  | 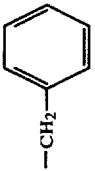(CH$_3$)$_3$COC(=O)− |  |  | H |
| H | H | H | H | H | H | H |
| −CH$_2$CH(CH$_3$)$_2$ | −CH$_2$CH(CH$_3$)$_2$ | −CH$_2$CH(CH$_3$)$_2$ | −CH$_2$CH(CH$_3$)$_2$ | −CH$_2$CH(CH$_3$)$_2$ | −CH$_2$CH(CH$_3$)$_2$ | −CH$_2$CH(CH$_3$)$_2$ |
| H | H | H | H | H | H | H |
| −CH$_2$CH$_2$CH$_2$CH$_3$ | −CH$_2$CH$_2$CH$_2$CH$_3$ | −CH$_2$−C$_6$H$_5$ | −CH(CH$_3$)$_2$ | −CH(CH$_3$)$_2$ | −CH(CH$_3$)$_2$ | −CH(CH$_3$)$_2$ |
| H | H | H | H | H | H | H |
| −OH | −OH | −OH | −OH | −OH | −OH | −OH |
| H | H | H | H | H | H | H |
| (CH$_3$)$_2$C(OH)− | (CH$_3$)$_2$C(OH)− | (CH$_3$)$_2$C(OH)− | cyclohexyl-C(OH)− | cyclohexyl-C(OH)− | cyclohexyl-C(OH)− | cyclohexyl-C(OH)− |

-continued

| 435 | 436 | 437 | 438 | 439 | 440 | 441 |
|---|---|---|---|---|---|---|
| 1-hydroxycyclohexyl | 1-hydroxycyclohexyl | 1-hydroxycyclohexyl | 1-hydroxycyclohexyl | 1-hydroxycyclohexyl | 1-hydroxycyclohexyl | 2-hydroxy-3-phenyl |
| H | H | H | H | H | H | H |
| —OH | —OH | —OH | —OH | —OH | | —OH |
| H | H | H | H | H | H | H |
| —CH(CH$_3$)$_2$ | —CH(CH$_3$)$_2$ | —CH(CH$_3$)$_2$ | —CH$_2$CH$_2$CH$_2$CH$_3$ | —CH$_2$CH$_2$CH$_2$CH$_3$ | —CH$_2$CH$_2$CH$_2$CH$_3$ | —CH(CH$_3$)$_2$ |
| H | H | H | H | H | H | H |
| —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ | —CH$_2$CH(CH$_3$)$_2$ |
| H | H | H | H | H | H | H |
| benzyl carbonate | benzoyl | phenylsulfonyl | cyclohexylmethyl carbonate | benzyl carbonate | (pyridin-3-yl)methyl carbonate | cyclohexylmethyl carbonate |

-continued

| No. | Ester group | | | | | | Alcohol group |
|---|---|---|---|---|---|---|---|
| 442 | benzyl ester | H | —CH₂CH(CH₃)₂ | H | —CH(CH₃)₂ | —OH | H | CH₂-CH(OH)-Ph |
| 443 | cyclohexylmethyl ester | H | —CH₂CH(CH₃)₂ | H | —CH(CH₃)₂ | —OH | H | CH(OH)-Ph |
| 444 | benzyl ester | H | —CH₂CH(CH₃)₂ | H | —CH(CH₃)₂ | —OH | H | CH(OH)-Ph |
| 445 | cyclohexylmethyl ester | H | —CH(CH₃)₂ | H | —CH₂CH(CH₃)₂ | —OH | H | CH(OH)-Ph |
| 446 | cyclohexylmethyl ester | H | —CH₂CH(CH₃)₂ | H | —CH₂CH(CH₃)₂ | —OH | H | CH(OH)-Ph |
| 447 | cyclohexylmethyl ester | H | —CH₂CH(CH₃)₂ | H | —CH(CH₃)₂ | —OH | H | CH(OH)-Ph |
| 448 | benzyl ester | H | —CH₂CH(CH₃)₂ | H | —CH(CH₃)₂ | —OH | H | C(OH)-Ph |

TABLE 2

(n = 1)

| Compd. No. | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|
| 449 | cyclohexyl-CH₂-O-C(O)- | H | —CH₂CH(CH₃)₂ | H | —CH₂CH(CH₃)₂ | H | —CH₃ | H | —OH | H | H |
| 450 | cyclohexyl-CH₂-O-C(O)- | H | —CH₂CH(CH₃)₂ | H | —CH₂-C₆H₅ | H | —CH₃ | H | —OH | H | H |
| 451 | phenyl-CH₂-O-C(O)- | H | —CH₂CH(CH₃)₂ | H | —CH₂-C₆H₅ | H | —CH₃ | H | —OH | H | H |
| 452 | phenyl-CH₂-O-C(O)- | H | —CH(CH₃)₂ | H | —CH₂CH(CH₃)₂ | H | —CH(CH₃)₂ | H | —OH | H | H |
| 453 | cyclohexyl-CH₂-O-C(O)- | H | —CH₂CH(CH₃)₂ | H | —CH₂CH(CH₃)₂ | H | —CH(CH₃)₂ | H | —OH | H | H |
| 454 | cyclohexyl-CH₂-O-C(O)- | H | —CH₂-C₆H₅ | H | —CH₂CH(CH₃)₂ | H | —CH(CH₃)₂ | H | —OH | H | H |
| 455 | cyclohexyl-CH₂-O-C(O)- | H | —CH(CH₃)₂ | H | —CH₂CH(CH₃)₂ | H | —CH₂CH₂CH₃ | H | —OH | H | H |

TABLE 2-continued (n = 1)

| Compd. No. | R¹ | R² | R³ | R⁴ | R⁵ | R⁶ R⁷ | R⁸ | R⁹ | R¹⁰ | R¹¹ |
|---|---|---|---|---|---|---|---|---|---|---|
| 456 | cyclohexylmethyl ester | H | —CH₂CH(CH₃)₂ | H | —CH₂CH(CH₃)₂ | H —CH₂CH₂CH₂CH₃ | H | —OH | H | H |
| 457 | benzyl ester | H | —CH₂CH(CH₃)₂ | H | —CH₂CH(CH₃)₂ | H —CH₂CH₂CH₂CH₃ | H | —OH | H | H |
| 458 | (2-pyridyl)methyl ester | H | —CH₂CH(CH₃)₂ | H | —CH₂CH(CH₃)₂ | H —CH₂CH₂CH₂CH₃ | H | —OH | H | H |
| 459 | cyclohexylmethyl ester | H | —CH₂CH(CH₃)₂ | H | —CH₂CH(CH₃)₂ | H —CH₂-phenyl | H | —OH | H | H |
| 460 | cyclohexylmethyl ester | H | —CH₂CH(CH₃)₂ | H | —CH₂CH(CH₃)₂ | H —CH₂CH₂CH₂CH₃ | H | —OH | H | —CH₃ |
| 461 | benzyl ester | H | —CH₂CH(CH₃)₂ | H | —CH₂CH(CH₃)₂ | H —CH₂CH₂CH₂CH₃, | H | —OH | H | —CH₃ |

TABLE 2-continued (n = 1)

| Compd. No. | R$^1$ | R$^2$ | R$^3$ | R$^4$ | R$^5$ | R$^6$ | R$^7$ | R$^8$ | R$^9$ | R$^{10}$ | R$^{11}$ |
|---|---|---|---|---|---|---|---|---|---|---|---|
| 469 | 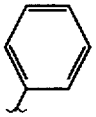 | H | —CH$_2$CH(CH$_3$)$_2$ | H | —CH$_2$CH(CH$_3$)$_2$ | H | —CH(CH$_3$)$_2$ | H | —OH | H |  |
| 470 | 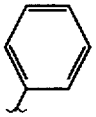 | H | —CH$_2$CH(CH$_3$)$_2$ | H | —CH$_2$CH(CH$_3$)$_2$ | H | —CH(CH$_3$)$_2$ | H | —OH | H |  |
| 471 | 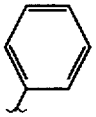 | H | —CH$_2$CH(CH$_3$)$_2$ | —CH$_3$ | —CH$_2$CH(CH$_3$)$_2$ | H | —CH(CH$_3$)$_2$ | H | —OH | H |  |
| 472 | 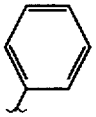 | H | —CH$_2$CH(CH$_3$)$_2$ | H | —CH$_2$CH(CH$_3$)$_2$ | H | —CH(CH$_3$)$_2$ | H | —OH | H |  |
| 473 | H | H | —CH$_2$CH(CH$_3$)$_2$ | H | —CH$_2$CH(CH$_3$)$_2$ | H | —CH(CH$_3$)$_2$ | H | —OH | H |  |
| 474 | 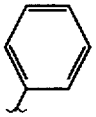 | H | —CH$_2$CH(CH$_3$)$_2$ | H | —CH$_2$CH(CH$_3$)$_2$ | H | —CH(CH$_3$)$_2$ | H | —OH | H |  |
| 475 | 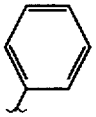 | H | —CH$_2$CH(CH$_3$)$_2$ | H | —CH$_2$CH(CH$_3$)$_2$ | H | —CH(CH$_3$)$_2$ | H | —OH | H |  |

TABLE 2-continued (n = 1)

| Compd. No. | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|
| 476 | −S(=O)₂−C₆H₅ | H | −CH₂CH(CH₃)₂ | H | −CH₂CH(CH₃)₂ | H | −CH(CH₃)₂ | H | −OH | H | C₆H₁₁ |
| 477 | −C(=O)O−CH₂−C₆H₁₁ | H | −CH₂−C₆H₅ | H | −CH₂CH(CH₃)₂ | H | −CH(CH₃)₂ | H | −OH | H | C₆H₁₁ |
| 478 | −C(=O)O−CH₂−C₆H₁₁ | H | −CH₂−C₆H₅ | H | −CH₂CH(CH₃)₂ | H | −CH(CH₃)₂ | H | −OH | H | C₆H₁₁ |
| 479 | −C(=O)O−CH₂−C₆H₁₁ | H | −CH₂CH(CH₃)₂ | H | −CH₂CH(CH₃)₂ | H | −CH(CH₃)₂ | H | −OH | H | C₆H₁₁ |
| 480 | −C(=O)O−CH₂−C₆H₁₁ | H | −CH₃ | H | −CH₂−C₆H₅ | H | −CH(CH₃)₂ | H | −OH | H | C₆H₁₁ |
| 481 | −C(=O)O−CH₂−C₆H₁₁ | H | −CH₂CH(CH₃)₂ | H | −CH₂−C₆H₅ | H | −CH(CH₃)₂ | H | −OH | H | C₆H₁₁ |
| 482 | −C(=O)O−CH₂−C₆H₁₁ | H | −CH₂CH(CH₃)₂ | H | −CH(CH₃)₂ | H | −CH₂CH₂CH₂CH₃ | H | −OH | H | C₆H₁₁ |

TABLE 2-continued
(n = 1)

| Compd. No. | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|
| 483 | -CH₂-cyclohexyl-C(=O)O- | H | -CH₂CH(CH₃)₂ | H | -CH₂CH(CH₃)₂ | H | -CH₂CH₂CH₂CH₃ | H | -OH | H | phenyl |
| 484 | -CH₂-phenyl-C(=O)O- | H | -CH₂-phenyl | H | -CH₂CH(CH₃)₂ | H | -CH₂CH₂CH₂CH₃ | H | -OH | H | phenyl |
| 485 | -CH₂-cyclohexyl-C(=O)O- | H | -CH₂CH(CH₃)₂ | H | -CH₂-phenyl | H | -CH₂CH₂CH(CH₃)₂ | H | -OH | H | phenyl |
| 486 | -CH₂-cyclohexyl-C(=O)O- | H | -CH₂CH(CH₃)₂ | H | -CH₃ | H | -CH₂-phenyl | H | -OH | H | phenyl |
| 487 | -CH₂-cyclohexyl-C(=O)O- | H | -CH₂CH(CH₃)₂ | H | -CH(CH₃)₂ | H | -CH₂-phenyl | H | -OH | H | phenyl |
| 488 | -CH₂-phenyl-C(=O)O- | H | -CH₃ | H | -CH₂CH(CH₃)₂ | H | -CH₂-phenyl | H | -OH | H | phenyl |
| 489 | -CH₂-phenyl-C(=O)O- | H | -CH(CH₃)₂ | H | -CH₂CH(CH₃)₂ | H | -CH₂-phenyl | H | -OH | H | phenyl |

TABLE 2-continued
(n = 1)
| Compd. No. | R¹ | R² | R³ | R⁴ | R⁵ | R⁶ | R⁷ | R⁸ | R⁹ | R¹⁰ | R¹¹ |
|---|---|---|---|---|---|---|---|---|---|---|---|
| 490 |  | H | —CH₂CH(CH₃)₂ | H | —CH₂CH(CH₃)₂ | H | —CH₂ | H | —OH | H | 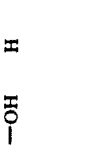 |
| 491 | 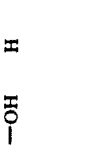 | H | —CH₂CH(CH₃)₂ | H | —CH₂CH(CH₃)₂ | H | —CH₂ | H | —OH | H |  |
| 492 | 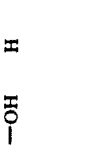 | —CH₃ | —CH₂CH(CH₃)₂ | H | —CH₂CH(CH₃)₂ | H | —CH₂ | H | —OH | H |  |
| 493 |  | H | —CH₂CH(CH₃)₂ | H | —CH₂CH(CH₃)₂ | H | —CH₂CH₂CH₂CH₃ | H | —OH | H |  |
| 494 |  | H | —CH₂CH(CH₃)₂ | H | —CH₂CH(CH₃)₂ | H | —CH₂CH₂CH₂CH₃ | H | —OH | H |  |
| 495 |  | H | —CH₂CH(CH₃)₂ | H | —CH₂CH(CH₃)₂ | H | —CH(CH₃)₂ | H | —OH | H |  |
| 496 |  | H | —CH₂CH(CH₃)₂ | H | —CH₂CH(CH₃)₂ | H | —CH(CH₃)₂ | H | —OH | H |  |

The compound (I) of the invention can be prepared using any of known methods. However, there are some preferable methods as will be hereinafter explained in detail.

Production 1

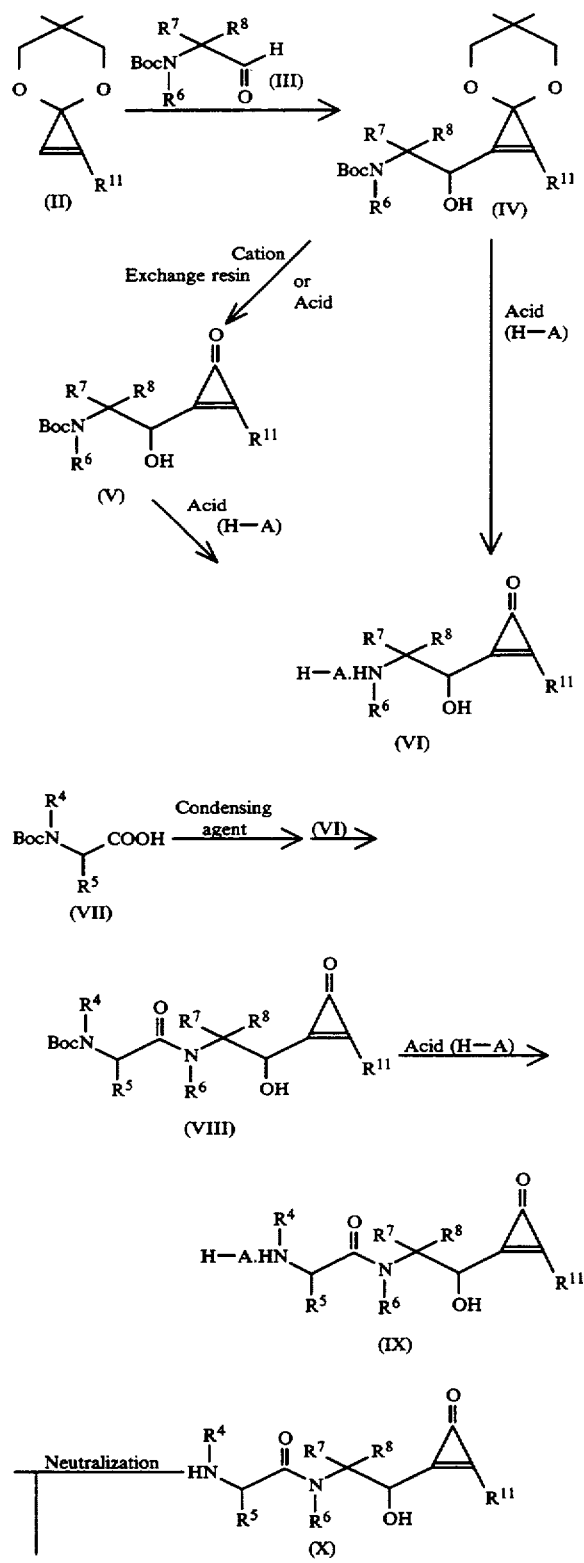

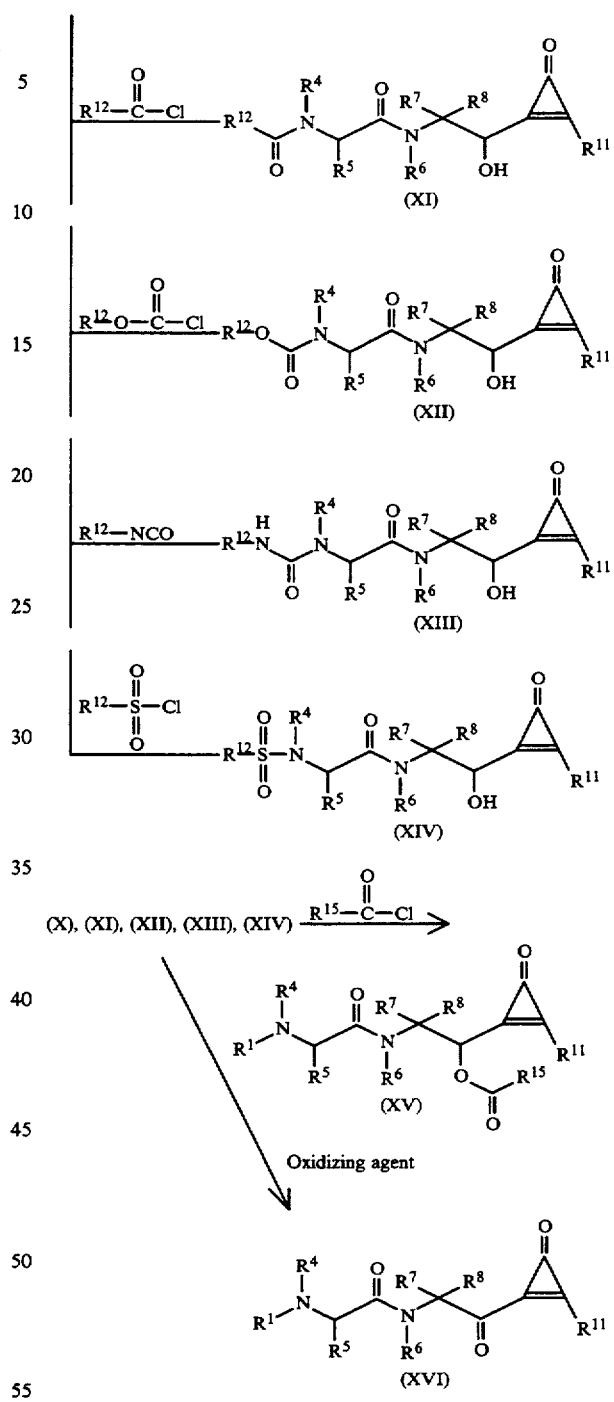

(wherein $R^1$, $R^4$, $R^5$, $R^6$, $R^7$, $R^8$, $R^{11}$ and $R^{12}$ are as defined above, and $R^{15}$ is $C_1$-$C_9$ alkyl group, Boc is tert-butoxycarbonyl group).

The compound of the general formula (IV) above can be prepared by dissolving the cyclopropenone ketal of the general formula (II) above, readily available by known method [Tetrahedron Letters, 32, 1339 (1991)], in ethereal solvent such as tetrahydrofuran, diethyl ether or the like and adding strong base such as n-butyllithium, methyllithium, lithium diisopropylamide or the like in the presence of an additive such as N,N,N', N'-tetramethylethylenediamine, hexamethylphosphoric triamide, 1,3-dimethyl-2-imidazolidone or the like at −40° C. to −100° C. to give a lithio compound, which is followed by the addition of tert-butoxycarbonylaminoaldehyde derivative of formula (III). In this reaction, the aldehyde of the general formula (III) above may be added to the cerium salt of lithio compound which previously produced by adding a suspension of anhydrous cerium chloride in tetrahydrofuran, n-hexane or the like to said lithio compound.

Then, the compound (IV) is treated with a cation exchange resin such as Amberlist 15$^R$ or with a mineral acid such as dilute sulfuric acid in order to selective deprotection of ketal so that the cyclopropenone derivative of the general formula (V) above can be obtained. Further, the compound (V) is allowed to react with a mineral acid such as hydrochloric acid, sulfuric acid or the like or an organic acid such as p-toluenesulfonic acid, methanesulfonic acid or the like, in a solvent such as dichloromethane, chloroform, dioxane, ethyl acetate or the like to isolate an amine salt (VI) as a stable compound.

Alternatively, the amine salt (VI) can be prepared in one step by reacting the compound of the general formula (IV) above with a mineral acid such as hydrogen chloride, hydrogen bromide, sulfuric acid or the like or an organic acid such as p-toluenesulfonic acid, methanesulfonic acid or the like in a solvent such as dichloromethane, chloroform, dioxane, ethyl acetate or the like with simultaneous deprotection of both of the ketal and tert-butoxycarbonyl group.

Then, the cyclopropenone derivatives of the general formula (VIII) above can be prepared by activating the N-substituted amino acid derivative of the general formula (VII) above with a condensing agent such as isobutyl chloroformate, diphenylphosphorylazide, carbonyldiimidazole, oxalyl chloride, dicyclohexylcarbodiimide or the like, if necessary, in the presence of an amine such as triethylamine, pyridine or the like, reacting it with the amine salt of the general formula (VI) obtained above and a base such as triethylamine, pyridine or the like.

Further, the amine salt of the general formula (IX) above can be obtained by treating with a mineral acid such as hydrogen chloride, hydrogen bromide, sulfuric acid, nitric acid or the like or an organic acid such as p-toluenesulfonic acid, methanesulfonic acid or the like to deprotect the tert-butoxycarbonyl group. Then, the compound of the general formula (XI) above can be prepared by reacting the compound (IX) with the acyl chloride of the formula $R^{12}$—CO—Cl in the presence of an amine such as triethylamine, pyridine or the like in an organic solvent such as chloroform, methylene chloride, ethyl acetate, dimethylformamide or the like.

Similarly, the compound (XII) can be prepared by reacting the compound (IX) with the chloroformic acid derivative of the formula $R^{12}$—O—CO—Cl and the compound (XIII) by reacting the compound (IX) with the isocyanate of the formula $R^{12}$—NCO, and the compound (XIV) by reacting the compound (IX) with the sulfonyl chloride of the formula $R^{12}$—SO$_2$—Cl. The compound (X) can be prepared by neutralizing the compound (IX) with an alkali such as lithium hydroxide, potassium hydroxide, sodium hydroxide or the like or an anion exchange resin.

Further, the compound of the general formula (XV) above can be prepared by reacting the compound (X)–(XIV) with the acyl chloride of the formula $R^{15}$—CO—Cl in the presence of an amine such as triethylamine, pyridine or the like in a solvent such as dichloromethane, chloroform, 1,2-dichloroethane or the like. The cyclopropenone derivative of the general formula (XVI) above can be prepared by oxidizing the hydroxy group of cyclopropenone derivative of formula (X)–(XIV) with a conventional oxidizing agent such as sulfur trioxide-pyridine complex-dimethyl sulfoxide, oxalyl chloride-dimethyl sulfoxide, acetic anhydride-dimethyl sulfoxide, N-chlorosuccinimide, chromium chloride-pyridine complex or the like.

Production 2

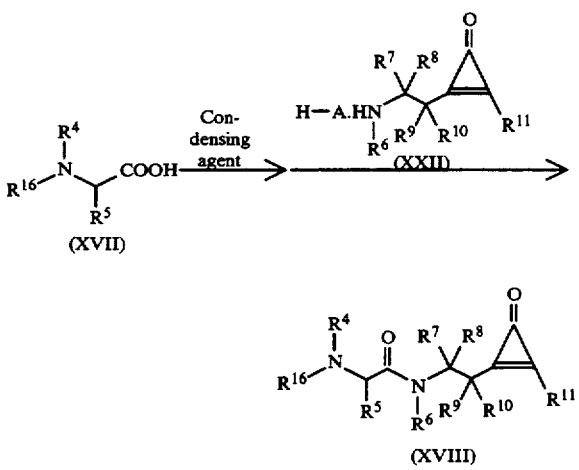

wherein $R^4$, $R^5$, $R^6$, $R^7$, $R^8$, $R^9$, $R^{10}$ and $R^{11}$ are as defined above, and $R^{16}$ is $R^{12}$—CO—, $R^{12}$—O—CO—, $R^{12}$—NH—CO— or $R^{12}$—SO$_2$— (in which $R^{12}$ is as defined above).

The cyclopropenone derivative of the general formula (XVIII) above can be prepared by activating carboxyl group of the N-substituted amino acid derivative of formula (XVII) by adding a condensing agent such as isobutyl chloroformate, diphenylphosphoryl azide, carbonyl diimidazole, oxalyl chloride, dicyclohexyl carbodiimide or the like, if necessary, in the presence of an amine such as triethylamine, pyridine or the like and then reacting with amine of formula (XXII) above and a base such as triethylamine, pyridine or the like.

Production 3

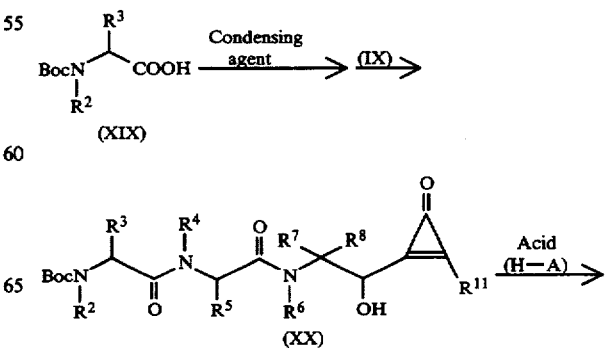

-continued

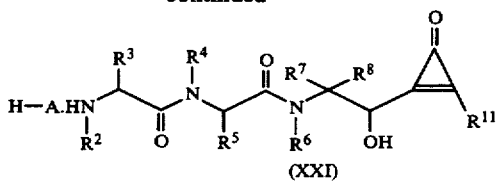

(XXI)

wherein $R^2$, $R^3$, $R^4$, $R^5$, $R^6$, $R^7$, $R^8$, $R^{11}$ and Boc are as defined above.

The N-protected amino acid of the general formula (XIX) above is activated with a condensing agent as described in the Production 1 and then allowed to react a compound (IX) in the presence of a base to give a compound of formula (XX) above. The product (XX) can be converted into an amine salt of formula (XXI) by treating with an acid selected from those described in the Production 1. Similarly, the amino group and hydroxyl group can be converted according to the process described in the Production 1.

As will be seen from the results of Experiments below, the compounds (I) of the invention proved to possess a potent inhibitory activity against thiol protease such as papain, cathepsin B, cathepsin H, cathepsin L, calpain or the like with excellent properties regarding oral absorbance, tissue transference and cell membrane permeability, indicating that they are clinically useful in the treatment of various diseases such as muscular dystrophy, amyotrophy, cardiac infarction, stroke, Alzheimer's disease, conscious disturbance and motor disturbance caused by brain trauma, multiple sclerosis, neuropathy of peripheral nerve, cataract, inflammation, allergy, fulminant hepatitis, osteoporosis, hypercalcemia, breast carcinoma, prostatic carcinoma, prostatomegaly or the like, and can be used as cancer growth inhibitors, cancer metastasis preventive agents or platelet-aggregation inhibitors.

When the compounds (I) of the present invention are clinically applied, they can be administered to subjects to be treated after formulating into appropriate forms containing, as an active ingredient, a therapeutically effective amount of compound (I) together with carriers therefor. The appropriate ratio of the active ingredient to carriers may vary from about 1% by weight to about 90% by weight. For example, the compounds of the present invention may be orally administered after formulating into an appropriate form such as granules, fine granules, powders, tablets, hard capsules, soft capsules, syrups, emulsions, suspensions, solutions or the like. They can be administered intravenously, intramuscularly or subcutaneously in the form of injections. Furthermore, they may be formulated in the form of suppositories, or powders which are prepared for injections at the time of use.

Formulations of the invention can be prepared using any of known methods in the art employing conventional carriers including organic or inorganic, solid or liquid, pharmaceutical carriers or diluents suitable for oral, enteral or parenteral administration. Examples of excipient usable for preparing solid formulations are lactose, sucrose, starch, talc, cellulose, dextrin, kaolin, calcium carbonate and the like. Liquid formulations for oral administration such as emulsion, syrups, suspensions, solutions or the like include generally usable inert diluents such as water, vegetable oils or the like. These formulations may further include adjuncts such as humectants, suspension aids, edulcorants, aromatics, tinctions or preservatives in addition to the inert diluents. The compound (I) can be formulated into solutions which are filled in absorbable carriers such as hard or soft gelatin capsules. Examples of solvents and suspending agents usable for preparing pharmaceutical formulations such as injections, suppositories or the like are water, propylene glycol, polyethylene glycol, benzyl alcohol, ethyl oleate, lecithin and the like. Examples of the base usable for suppositories are cacao butter, emulsified cacao butter, lauric acid, Wittep sol and the like.

The dose of compound (I) may vary depending on various factors such as age, conditions or symptoms of the patient to be treated and the like. Appropriate daily dosage of the compound (I) of the present invention on oral administration to adult is generally about 0.01–1000 mg though, it is preferable to adjust appropriately for each case according to the conditions as mentioned above. The daily dosage of the compound (I) may be administered once or in two or three divisions at appropriate intervals or intermittently.

Additionally, when the compound (I) is administered in the form of injections, one dosage of 0.001–100 mg of said compound can be preferably administered to adult continuously or intermittently.

The following Examples further describe the present invention in more detail, but these are illustrative only and are not intended to limit the scope of the invention.

REFERENCE EXAMPLE 1

Preparation of
2-{(2S)-2-tert-butoxycarbonylamino-1-hydroxy-3-methylbutyl}-3-phenylcyclopropenone
2,2-dimethyl-1,3-propanediyl ketal To a solution of 3.51 g of 2-phenylcyclopropenone 2,2-dimethyl-1,3-propanediyl ketal in 30 ml of tetrahydrofuran was added 3.8 g of N,N,N',N'-tetramethylethyldiamine. To the reaction solution chilled at −78° C. was added a 1.55 mol/l solution of n-butyllithium in 10.5 ml of hexane, and the mixture was stirred for 20 minutes. Then, 30 ml of a tetrahydrofuran suspension of anhydrous cerium chloride prepared by drying 8.0 g of cerium chloride heptahydrate at 140° C./1 mm Hg for 2 hours was added to the mixture, which was stirred for 20 minutes. A solution of 1.82 g of N-tert-butoxycarbonyl-L-valinal in 20 ml of tetrahydrofuran was added, and the resultant mixture was stirred at −78° C. for 2 hours. A solution of 1 ml of water in 5 ml of tetrahydrofuran was added to the reaction mixture, which was allowed to warm at room temperature and filtered through celite. The celite was washed well with ethyl acetate, and the filtrate was dried over sodium sulfate, filtered, concentrated and chromatographed on a column of silica gel, eluting with hexane containing 20% ethyl acetate as a developing solvent to give 2.71 g of the titled product.

Yield: 72% IR(KBr, cm$^{-1}$): 3430, 2960, 1855, 1800, 1710, 1690 NMR(CD$_3$OD, δ): 0.95–1.60(m, 12H), 1.38(s, 3H), 1.42(s, 6H), 1.95–2.15(m, 1H), 3.60–3.75(m, 1H), 3.75–3.95(m, 4H), 5.0–5.10(m, 1H), 6.03(d, J=10 Hz, 0.33H), 6.23(d, J=10 Hz, 0.67H), 7.40–7.65(m, 3H), 7.70–7.90(m, 2H)

REFERENCE EXAMPLE 2

Preparation of 2-{(2S)-2-amino-1-hydroxy-3-methylbutyl}-3-phenyl-cyclopropenone hydrochloride To 8 ml of a dioxane solution of 3.12 g of 2-{(2S)-2-tert-butoxycarbonylamino-1-hydroxy-3-methylbutyl}-3-phenylcyclopropenone 2,2-dimethyl-1,3-propanediyl ketal obtained in Reference Example 1 were added 0.2 ml of water and 24 ml of a dioxane solution of 4N hydrogen chloride, and the mixture was stirred for 20 minutes. The resulting crystals were filtered and washed with dioxane to give 1.87 g of the titled product.

Yield: 94% IR(KBr, cm$^{-1}$): 3200, 1855, 1618 NMR(CD$_3$OD, δ): 1.21(t, J=7 Hz, 4.5H), 1.24(t, J=7 Hz, 1.5H), 2.0–2.2(m, 0.25H), 2.2–2.4(m, 0.75H), 3.38(t, J=6 Hz, 0.25H), 3.45(t, J=6 Hz, 0.75H), 5.21(d, J=6 Hz, 0.75H), 5.45(d, J=6 Hz, 0.25H), 7.60–7.80(m, 3H), 8.10–8.20(m, 2H)

EXAMPLE 1

Preparation of 2-[(1S,2S)-2-{(s)-2-cyclohexylmethoxycarbonylamino-4-methylvalerylamino}-1-hydroxy-3-methylbuthyl]-3-phenylcyclopropenone (Comp. No. 77 in Table 1)

To a solution of 2.46 g of N-cyclohexylmethoxycarbonyl-(S)-leucine in 40 ml of methylene chloride chilled at −5° C. were added 0.92 g of triethylamine and 1.15 g of isobutyl chloroformate, and the resultant mixture was stirred for 15 minutes. Further, 1.87 g of 2-{(2S)-2-amino-1-hydroxy-3-methylbutyl)-3-phenylcyclopropenone hydrochloride prepared in Reference Example 2 and 0.97 g of triethylamine were added, and one hour later 10 ml of 0.5N hydrochloric acid was added. The resultant mixture was shaken with methylene chloride, and the organic layer was washed with water, saturated aqueous sodium bicarbonate and saturated brine in that order, dried over magnesium sulfate and filtered. The filtrate was concentrated and chromatographed on a column of silica gel, eluting with hexane:ethyl acetate (1:1) as developing solvent, and the product was recrystallized from diethyl ether to give 1.86 g of the titled product.

Yield: 55% mp: 85°–89° C. IR(KBr, cm$^{-1}$): 3330, 1858, 1695, 1658, 1625 NMR(CDCl$_3$, δ): 0.65–1.80(m, 26H), 2.25–2.45(m, 1H), 3.55–3.85(m, 3H), 4.0–4.15(m, 1H), 5.12(d, J=4 Hz, 1H), 5.30–5.45(m, 1H), 7.40–7.65(m, 4H), 7.95–8.05(m, 2H)

EXAMPLE 2

Preparation of 2-[(1R, 2S)-2-{(S)-2-cyclohexylmethoxycarbonylamino-4-methylvalerylamino}-1-hydroxy-3-methylbutyl]-3-phenylcyclopropenone (Comp. No. 77 in Table 1)

The titled isomer was obtained as a product of the chromatography on a column of silica gel in Example 1.

Yield: 18% mp: 148°–149° C. IR(KBr, cm$^{-1}$): 3350, 3260, 1860, 1825, 1715, 1653, 1625 NMR(CDCl$_3$, δ): 0.60–1.80(m, 26H), 2.05–2.25(m, 1H), 3.60–3.85(m, 2H), 4.05–4.20(m, 2H), 5.15(d, J=3 Hz, 1H), 5.20–5.40(m, 1H), 7.05(d, J=8 Hz, 1H), 7.45–7.60(m, 3H), 7.95–8.05(m, 2H)

EXAMPLE 3

Preparation of 2-[(1R,2S)-1-acetoxy-2-{(S)-2-cyclohexylmethoxycarbonylamino-4-methylvalerylamino}-3methylbutyl]-3-phenylcyclopropenone (Comp. No. 78 in Table 1)

To 5 ml of a methylene chloride solution of 149 mg of 2-[(1R,2S)-2-{(S)-2-cyclohexylmethoxycarbonylamino-4-methylvalerylamino}-1-hydroxy-3-methylbutyl]-3-phenylcyclopropenone obtained in Example 2 were added 81 mg of acetyl chloride and 102 mg of triethylamine. The resultant mixture was stirred at room temperature for 3 hours, mixed with diluted hydrochloric acid and shaken with methylene chloride. The organic layer was washed with water, saturated aqueous sodium bicarbonate and saturated brine in that order, dried over magnesium sulfate and filtered. The filtrate was concentrated and chromatographed on a column of silica gel, eluting with hexane:ethyl acetate (1:1) to give 73 mg of the titled product.

Yield: 45% IR(KBr, cm$^{-1}$): 3350, 3280, 1868, 1758, 1720, 1704, 1670, 1635 NMR(CDCl$_3$, δ): 0.79(d, J=7.0 Hz, 3H), 0.81(d, J=6.3 Hz, 3H), 0.70–0.95(m, 2H), 1.02(d, J=6.6 Hz, 3H), 1.15(d, J=6.6 Hz, 3H), 1.05–1.35(m, 4H), 1.35–1.85(m, 8H), 2.03(m, 1H), 2.20(s, 3H), 3.75(s, 2H), 4.10(m, 1H), 4.31(m, 1H), 5.06(d, J=8.0 Hz, 1H), 6.12(d, J=4.2 Hz, 1H), 6.52(d, J=8.1 Hz, 1H), 7.45–7.65(m, 3H), 7.84(d, J=7.1 Hz, 2H)

The compounds in the following Examples 4–120 were prepared by the same manner as in Reference Examples 1–2 and Examples 1, 2 and 3. Physicochemical properties of each compound are shown below.

EXAMPLE 4 Preparation of 2-[(2S)-2-((S)-2-cyclohexylmethoxycarbonylamino-4-methylvalerylamino)-1-hydroxy-3-methylbutyl]cyclopropenone (compd. No. 4 in Table 1)

IR(KBr, cm$^{-1}$): 3310, 1825, 1690, 1650 NMR(CDCl$_3$, δ): 0.80–1.80(m, 26H), 1.90–2.35(m, 2H), 3.60–4.25(m, 4H), 4.87–5.05(m, 1H), 5.05–5.45(m, 1H), 6.85–7.03(m, 0.3H), 7.35–7.52(m, 0.7H), 8.54(s, 0.7H), 8.62(s, 0.3H)

EXAMPLE 5

Preparation of 2-[(2S)-2-((S)-2-benzyloxycarbonylamino-4-methylvalerylamino)-1-hydroxy-4-methylpentyl]cyclopropenone (compd. No. 10 in Table 1)

IR(KBr, cm$^{-1}$): 3320, 1825, 1697, 1652 NMR(CDCl$_3$, δ): 0.90–1.05(m, 12H), 1.40–1.80(m, 6H), 4.05–4.32(m, 2H), 4.68–4.87(m, 1H), 5.09(s, 2H), 4.90–5.60(m, 2H), 6.85–7.10(m, 1H), 7.34(s, 5H), 8.43(s, 0.95H), 8.62(s, 0.05H)

EXAMPLE 6

Preparation of 2-[(2S)-2-((S)-2-cyclohexylmethoxycarbonylamino-4-methylvalerylamino)-1-hydroxyhexyl]cyclopropenone (compd. No. 15 in Table 1)

IR(KBr, cm$^{-1}$): 3340, 1830, 1690, 1650 NMR(CDCl$_3$, δ): 0.80–1.05(m, 11H), 1.10–1.88(m, 18H), 2.24(s, 1H), 3.73–3.95(m, 2H), 4.05–4.30(m, 2H), 4.80–4.93(m, 1H), 5.20–5.35(m, 0.2H), 5.35–5.55(m, 0.8H), 5.55–5.75(m, 0.8H), 6.95–7.05(m, 0.2H), 8.57(s, 0.8H), 8.68(s, 0.2H)

EXAMPLE 7

Preparation of
2-[(2S)-2-((S)-2-benzyloxycarbonylamino-4-methyl-
valerylamino)-1-hydroxyhexyl]cyclopropenone
(compd. No. 16 in Table 1)

IR(KBr, cm⁻¹): 3320, 1828, 1690, 1645
NMR(CDCl₃, δ): 0.75-1.0(m, 9H), 1.15-1.85(m, 9H), 2.25(s, 1H), 3.98-4.27(m, 2H), 4.68-4.87(m, 1H), 5.07(s, 2H), 5.45-5.80(m, 1.8H), 6.95-7.05(m, 0.2H), 7.32(s, 5H), 8.43(s, 0.8H), 8.57(s, 0.2H)

EXAMPLE 8

Preparation of
2-[(2S)-1-acetoxy-2-((S)-2-benzyloxycarbonylamino-4-methylvalerylamino)hexyl]cyclopropenone (compd. No. 20 in Table 1)

IR(neat, cm⁻¹): 3320, 1845, 1755, 1725, 1710, 1668
NMR(CDCl₃, δ): 0.80-1.0(m, 9H), 1.20-1.75(m, 9H), 2.15(s, 0.45H), 2.20(s, 2.55H), 4.08-4.23(m, 1H), 4.35-4.50(m, 1H), 5.20(s, 2H), 5.18(d, J=7 Hz, 0.85H), 5.22(d, J=7 Hz, 0.15H), 5.70(d, J=4 Hz, 0.85H), 6.78(d, J=4 Hz, 0.15H), 6.43(d, J=8 Hz, 0.15H), 6.46(d, J=8 Hz, 0.85H), 7.35(s, 5H), 8.49(s, 0.85H), 8.52(s, 0.15H)

EXAMPLE 9

Preparation of
2-[(2S)-2-((S)-2-benzyloxycarbonylamino-4-methyl-
valerylamino)-1-hydroxy-3-phenylpropyl]cyclopropenone (compd. No. 26 in Table 1)

IR(KBr, cm⁻¹): 3330, 1830, 1700, 1655
NMR(CDCl₃, δ): 0.65-0.95(m, 6H), 1.10-1.65(m, 3H), 1.93(s, 1H), 2.75-3.25(m, 2H), 3.90-4.55(m, 2H), 4.60-4.83(m, 1H), 5.05(s, 2H), 5.15-5.85(m, 2H), 7.05-7.45(m, 10H), 8.39(s, 0.8H), 8.53(s, 0.2H)

EXAMPLE 10

Preparation of
2-[(2S)-2-((S)-2-cyclohexylmethoxycarbonylamino-4-methylvalerylamino)-1-hydroxyhexyl]-3-methylcyclopropenone (compd. No. 34 in Table 1)

IR(KBr, cm⁻¹): 3320, 1845, 1690, 1653, 1630
NMR(CDCl₃, δ): 0.85-1.10(m, 11H), 1.10-1.95(m, 18H), 2.33(s, 3H), 2.49(s, 1H), 3.75-3.97(m, 2H), 3.97-4.28(m, 2H), 4.73-4.90(m, 1H), 5.20-5.85(m, 1.6H), 7.10-7.50(m, 0.4H)

EXAMPLE 11

Preparation of
2-[(2S)-2-((S)-2-benzyloxycarbonylamino-4-methyl-
valerylamino)-1-hydroxy-4methylpentyl]-3-ethylcyclopropenone (compd. No. 40 in Table 1)

IR(neat, cm⁻¹): 3330, 1845, 1700, 1658, 1625
NMR(CDCl₃, δ): 0.85-1.05(m, 12H), 1.30(q, J=7 Hz, 3H), 1.40-1.75(m, 6H), 1.83(s, 1H), 2.58-2.78(m, 2H), 3.80-4.30(m, 2H), 4.65-4.85(m, 1H), 4.90-5.03(m, 0.5H), 5.09(m, 2H), 5.37-5.65(m, 1.5H), 5.70-5.85(m, 0.5H), 7.05-7.25(m, 0.5H), 7.34(s, 5H)

EXAMPLE 12

Preparation of
2-[(2S)-2-((S)-2-cyclohexylmethoxycarbonylamino-4-methylvalerylamino)-1-hydroxyhexyl]-3-isopentylcyclopropenone (compd. No. 44 in Table 1)

IR(KBr, cm⁻¹): 3310, 1838, 1720, 1698, 1652, 1620
NMR(CDCl₃, δ): 0.85-1.10(m, 17H), 1.10-1.85(m, 21H), 2.45-2.55(m, 1H), 2.55-2.70(m, 2H), 3.73-3.93(m, 2H), 3.93-4.25(m, 2H), 4.70-4.85(m, 1H), 5.25-5.85(m, 1.6H), 7.30-7.45(m, 0.4H)

EXAMPLE 13

Preparation of
2-[(1S,2S)-2-((S)-2-cyclohexylmethoxycarbonylamino-4-methylvalerylamino)-1-hydroxyhexyl]-3-((Z)-1-hexenyl)cyclopropenone (compd. No. 55 in Table 1)

mp: 138°-140° C. IR(KBr, cm⁻¹): 3290, 1838, 1711, 1655, 1630 NMR(CDCl₃, δ): 0.83-1.08(m, 14H), 1.10-2.05(m, 22H), 2.56(m, 2H), 3.85(s, 2H), 4.02(m, 1H), 4.15(m, 1H), 4.82(m, 1H), 5.22-5.48(m, 2H), 6.26(d, J=10 Hz, 1H), 6.48(m, 1H), 7.08(m, 1H)

EXAMPLE 14

Preparation of
2-[(1s,2S)-2-((S)-2-benzyloxycarbonylamino-4-methyl-
valerylamino)-1-hydroxyhexyl]-3-((Z)-1-hexenyl)cyclopropenone (compd. No. 56 in Table 1)

mp: 87°-94° C. IR(KBr, cm⁻¹): 3300, 1836, 1689, 1645 NMR(CDCl₃, δ): 0.80-1.03(m, 12H), 1.22-1.80(m, 13H), 2.56(m, 2H), 4.01(m, 1H), 4.17(m, 1H), 4.77(m, 1H), 5.08(s, 2H), 5.19(m, 1H), 5.45(m, 1H), 6.24(d, J=9.9 Hz, 1H), 6.46(m, 1H), 7.04(d, J=7.7 Hz, 1H), 7.33(s, 5H)

EXAMPLE 15

Preparation of
2-[(1S,2S)-2-((S)-2-benzyloxycarbonylamino-4-methyl-
valerylamino)-1-hydroxyhexyl]-3-((E)-1-hexenyl)cyclopropenone (compd. No. 58 in Table 1)

mp: 116° C. IR(KBr, cm⁻¹): 3308, 1842, 1698, 1655 NMR(CDCl₃, δ): 0.85-1.0(m, 12H), 1.15-1.90(m, 13H), 2.27(dt, J=6.8 Hz, 6.5 Hz, 2H), 3.97(m, 1H), 4.17(m, 1H), 4.75(m, 1H), 5.08(s, 2H), 5.57(d, J=6.5 Hz, 1H), 6.24(d, J=16 Hz, 1H), 6.90(dt, J=16 Hz, 6.8 Hz, 1H), 7.10(d, J=6.8 Hz, 1H), 7.32(s, 5H)

EXAMPLE 16

Preparation of
2-[(1S,2S)-2-((S)-2-benzyloxycarbonylaminopro-
pionylamino)-1-hydroxy-3-methylbutyl]-3-phenylcyclopropenone (compd. No. 68 in Table 1)

mp: 156°-158° C. IR(KBr, cm⁻¹): 3290, 1850, 1690, 1643, 1618 NMR(CDCl₃, δ): 0.98(d, J=5.9 Hz, 3H), 1.07(d, J=6.6 Hz, 3H), 1.19(d, J=7.0 Hz, 3H), 2.36(m, 1H), 3.61(m, 1H), 4.18(m, 1H), 4.90-5.15(m, 3H), 5.47(m, 1H), 7.31(s, 5H), 7.25-7.65(m, 5H), 7.95(d, J=7.4 Hz, 2H)

EXAMPLE 17

Preparation of
2-[(2S)-2-((S)-2-benzyloxycarbonylaminopro-
pionylamino)-1-hydroxy-3-methylbutyl]-3-phenylcyclopropenone (compd. No. 68 in Table 1)

IR(KBr, cm⁻¹): 3280, 1852, 1696, 1642, 1618 NMR(CDCl₃, δ): 0.85-1.30(m, 9H), 2.11(m, 0.4H), 2.34(m, 0.6H), 3.64(m, 0.6H), 4.02-4.28(m, 1.4H), 4.85-5.20(m, 3H), 5.49(m, 0.4H), 5.62(m, 0.6H), 6.99(d, J=7.7 Hz, 0.6H), 7.15-7.38(m, 5.4H), 7.15-7.65(m, 4H), 7.88-8.05(m, 2H)

EXAMPLE 18

Preparation of 2-[(1S, 2S)-2-((S)-2-benzyloxycarbonylamino-3-methylbutyrylamino)-1-hydroxy-3-methylbutyl]-3-phenylcyclopropenone (compd. No. 70 in Table 1)

mp: 157°-158° C. IR(KBr, cm$^{-1}$): 3310, 1850, 1697, 1643, 1618 NMR(CDCl$_3$, δ): 0.74(d, J=6.8 Hz, 3H), 0.85(d, J=6.7 Hz, 3H), 0.98(d, J=6.5 Hz, 3H), 1.08(d, J=6.6 Hz, 3H), 2.04(m, 1H), 2.36(m, 1H), 3.69(m, 1H), 4.01(m, 1H), 4.90-5.10(m, 3H), 5.47(d, J=8.2 Hz, 1H), 6.15(d, J=8.2 Hz, 1H), 7.30(s, 5H), 7.40-7.60(m, 4H), 7.93-8.0(m, 2H)

EXAMPLE 19

Preparation of 2-[(1R, 2S)-2-((S)-2-benzyloxycarbonylamino-3-methylbutyrylamino)-1-hydroxy-3-methylbutyl]-3-phenylcyclopropenone (compd. No. 70 in Table 1)

mp: 63°-71° C. IR(KBr, cm$^{-1}$): 3310, 1860, 1700, 1660, 1630 NMR(CDCl$_3$, δ): 0.79(d, J=6.8 Hz, 3H), 0.80(d, J=6.9 Hz, 3H), 1.05(d, J=6.7 Hz, 3H), 1.13(d, J=6.6 Hz, 3H), 1.98(m, 1H), 2.14(m, 1H), 3.90-4.15(m, 2H), 4.92(d, J=12 Hz, 1H), 5.03(d, J=12 Hz, 1H), 5.13(m, 1H), 5.42(d, J=7.0 Hz, 1H), 6.96(d, J=7.2 Hz, 1H), 7.30(s, 5H), 7.40-7.63(m, 4H), 7.97(d, J=7.0 Hz, 2H)

EXAMPLE 20 preparation of 2-[(1S, 2S)-1-hydroxy-2-((S)-2-isobutoxycarbonylamino-4-methylvalerylamino)-3-methylbutyl]-3-phenylcyclopropenone (compd. No. 72 in Table 1)

mp: 145°-146° C. IR(KBr, cm$^{-1}$): 3320, 1848, 1692, 1644, 1620 NMR(CDCl$_3$, δ): 0.77(d, J=4.3 Hz, 6H), 0.87(d, J=6.7 Hz, 6H), 1.01(d, J=6.5 Hz, 3H), 1.09(d, J=6.5 Hz, 3H), 1.29(m, 2H), 1.52(m, 1H), 1.84(m, 1H), 2.39(m, 1H), 3.60-3.87(m, 3H), 4.10(m, 1H), 5.12(d, J=3.5 Hz, 1H), 5.29(m, 1H), 6.20(s, 1H), 7.38-7.60(m, 4H), 7.98(d, J=6.9 Hz, 2H)

EXAMPLE 21

Preparation of 2-[(1R, 2S)-1-hydroxy-2-((S)-2-isobutoxycarbonylamino-4-methylvalerylamino)-3-methylbutyl]-3-phenylcyclopropenone (compd. No. 72 in Table 1)

mp: 173°-174° C. IR(KBr, cm$^{-1}$): 3400, 3260, 1863, 1828, 1722, 1655, 1626 NMR(CDCl$_3$, δ): 0.71(d, J=4.1 Hz, 6H), 0.84(d, J=6.6 Hz, 6H), 1.08(d, J=6.5 Hz, 3H), 1.14(d, J=6.6 Hz, 3H), 1.30-1.60(m, 2H), 1.60-1.90(m, 2H), 2.13(m, 1H), 3.55-3.90(m, 2H), 3.98-4.18(m, 2H), 5.03-5.18(m, 3H), 6.79(m, 1H), 7.40-7.63(m, 3H), 7.99(d, J=7.8 Hz, 2H)

EXAMPLE 22

Preparation of 2-[(1S, 2S)-2-((S)-2-tert-butoxycarbonylamino-4-methylvalerylamino)-1-hydroxy-3-methylbutyl]-3-phenylcyclopropenone (compd. No. 73 in Table 1)

mp: 158°-161° C. IR(KBr, cm$^{-1}$): 3330, 1858, 1685, 1655, 1625 NMR(CDCl$_3$,δ): 0.75(d, J=6.4 Hz, 6H), 1.02(d, J=6.7 Hz, 3H), 1.09(d, J=6.6 Hz, 3H), 1.17-1.60(m, 3H), 1.39(s, 9H), 2.39(m, 1H), 3.65(m, 1H), 4.04(m, 1H), 5.02-5.18(m, 2H), 6.25(m, 1H), 7.33(m, 1H), 7.45-7.60(m, 3H), 7.95-8.05(m, 2H)

EXAMPLE 23

Preparation of 2-[(1R, 2S)-2-((S)-2-tert-butoxycarbonylamino-4-methylvalerylamino)-1-hydroxy-3-methylbutyl]-3-phenylcyclopropenone (compd. No. 73 in Table 1)

mp: 182°-183° C. IR(KBr, cm$^{-1}$): 3380, 3260, 1860, 1825, 1708, 1655, 1625 NMR(CDCl$_3$, δ): 0.68(d, J=5.6 Hz, 6H), 1.08(d, J=6.6 Hz, 3H), 1.11(d, J=6.7 Hz, 3H), 1.25-1.55(m, 3H), 1.38(s, 9H), 2.13(m, 1H), 3.98-4.13(m, 2H), 5.04(d, J=5.9 Hz, 1H), 5.13(dd, J=6.4 Hz, 3.0 Hz, 1H), 5.35(d, J=6.4 Hz, 1H), 8.95(d, J=7.0 Hz, 1H), 7.45-7.65(m, 3H), 7.98-8.07(m, 2H)

EXAMPLE 24

Preparation of 2-[(1S, 2S)-2-{N-((S)-2-cyclohexylcarbonylamino-4-methylvaleryl)-N-methylamino}-1-hydroxy-3-methylbutyl]-3-phenylcyclopropenone (compd. No. 80 in Table 1)

IR(KBr, cm$^{-1}$): 3416, 1856, 1716, 1640 NMR(CDCl$_3$, δ): 0.86(d, J=7.1 Hz, 3H), 0.92(d, J=7.1 Hz, 3H), 0.97(d, J=6.5 Hz, 3H), 1.10(d, J=6.6 Hz, 3H), 0.65-1.80(m, 14H), 2.64(m, 1H), 3.22(s, 3H), 3.05-3.40(m, 2H), 3.53(dd, J=11 Hz, 7.0 Hz, 1H), 4.45(m, 1H), 4.87(d, J=8.7 Hz, 1H), 5.10(dd, J=9.1 Hz, 4.3 Hz, 1H), 6.80(m, 1H), 7.35-7.60(m, 3H), 7.93(d, J=7.2 Hz, 2H)

EXAMPLE 25

Preparation of 2-[(1S, 2S)-2-((S)-2-benzyloxycarbonylamino-4-methylvalerylamino)-1-hydroxy-3-methylbutyl]-3-phenylcyclopropenone (compd. No. 83 in Table 1)

mp: 84°-94° C. IR(KBr, cm$^{-1}$): 3320, 1855, 1700, 1655, 1625 NMR(CDCl$_3$, δ): 0.60-0.85(m, 6H), 0.97(d, J=6 Hz, 3H), 1.07(d, J=6 Hz, 3H), 1.20-1.60(m, 3H), 1.85-2.25(m, 1H), 2.25-2.45(m, 1H), 3.55-3.70(m, 1H), 4.0-4.10(m, 1H), 4.85-5.15(m, 3H), 5.53(d, J=8 Hz, 1H), 7.29(s, 5H), 7.40-7.60(m, 4H), 7.90-8.05(m, 2H)

EXAMPLE 26

Preparation of 2-[(2S)-2-((S)-2-benzyloxycarbonylamino-4-methylvalerylamino)-1-hydroxy-3-methylbutyl]-3-phenylcyclopropenone (compd. No. 83 in Table 1)

IR(KBr, cm$^{-1}$): 3300, 1855, 1700, 1655, 1625 NMR(CDCl$_3$, δ): 0.60-1.55(m, 15H), 2.05-2.25(m, 1.6H), 2.25-2.45(m, 0.4H), 3.55-3.70(m, 0.4H), 3.95-4.25(m, 1.6H), 4.85-5.20(m, 3H), 5.53(d, J=8 Hz, 0.6H), 5.62(d, J=8 Hz, 0.4H), 7.08(d, J=8 Hz, 0.6H), 7.50(s, 5H), 7.40-7.65(m, 3.4H), 7.90-8.10(m, 2H)

EXAMPLE 27

Preparation of 2-[(1S, 2S)-2-{(S)-2-(N-benzyloxycarbonyl-N-methylamino)-4-methylvalerylamino{-1-hydroxy-3-methylbutyl]-3-phenylcyclopropenone (compd. No. 85 in Table 1)

mp: 117° C.

IR(KBr, cm$^{-1}$): 3335, 3298, 1858, 1699, 1672, 1628 NMR(CDCl$_3$, δ): 0.70-0.90(m, 6H), 0.96(d, J=6.6 Hz, 3H), 1.03(d, J=6.6 Hz, 3H), 1.25-1.65(m, 3H), 2.35(m, 1H), 2.57(s, 3H), 3.62(m, 1H), 4.64(m, 1H), 5.07(d, J=4.9 Hz, 1H), 5.15(s, 2H), 7.04(d, J=7.5 Hz, 1H), 7.36(s, 5H), 7.38-7.58(m, 3H), 7.94(d, J=6.5 Hz, 2H)

EXAMPLE 28

Preparation of 2-[(1R, 2S)-2-{(S)-2-(N-benzyloxycarbonyl-N-methylamino)-4-methylvalerylamino}-1-hydroxy-3-methylbutyl]-3-phenylcyclopropenone (compd. No. 85 in Table 1)

mp: 112° C. IR(KBr, cm$^{-1}$): 3320, 3283, 1863, 1703, 1661, 1632 NMR(CDCl$_3$, δ): 0.70(d, J=8.4 Hz, 3H), 0.73(d, J=6.7 Hz, 3H), 0.96(d, J=5.1 Hz, 3H), 1.09(d, J=6.4 Hz, 3H), 1.28(m, 1H), 1.40-1.70(m, 2H), 2.05(m, 1H), 2.80(s, 3H), 3.94(m, 1H), 4.48(t, J=7.3 Hz, 1H), 4.94-5.20(m, 3H), 6.65(m, 1H), 7.33(s, 5H), 7.38-7.62(m, 3H), 7.98(d, J=6.4 Hz, 2H)

EXAMPLE 29

Preparation of 2-[(1S, 2S)-1-hydroxy-3-methyl-2-{(S)-4-methyl-2-(2-pyridylmethoxycarbonylamino)valerylamino}butyl]-3-phenylcyclopropenone hydrochloride (compd. No. 97 in Table 1)

mp: 158°-160° C.(dec.) IR(KBr, cm$^{-1}$): 3279, 1854, 1738, 1676, 1630, 1615 NMR (CD$_3$OD, δ): 0.52(d, J=6.6 Hz, 3H), 0.64(d, J=6.5 Hz, 3H), 0.90(d, J=6.7 Hz, 3H), 0.95-1.33(m, 2H), 1.07(d, J=6.7 Hz, 3H), 1.46(m, 1H), 2.05(m, 1H), 3.97-4.16(m, 2H), 5.21(d, J=2.4 Hz, 1H), 5.28(d, J=15 Hz, 1H), 5.43(d, J=15 Hz, 1H), 7.50-7.70(m, 3H), 7.97-8.15(m, 4H), 8.61(td, J=8.0 Hz, 1.5 Hz, 1H), 8.81(d, J=5.2 Hz, 1H)

EXAMPLE 30

Preparation of 2-[(1R, 2S)-1-hydroxy-3-methyl-2-{(S)-4-methyl-2-(2-pyridylmethoxycarbonylamino)valerylamino}butyl]-3-phenylcyclopropenone (compd. No. 97 in Table 1)

mp: 52°-59° C. IR (KBr, cm$^{-1}$): 3300, 1858, 1715, 1660, 1630 NMR(CDCl$_3$, δ): 0.71(d, J=7.4 Hz, 6H), 1.03(d, J=6.3 Hz, 3H), 1.11(d, J=6.4 Hz, 3H), 1.38-1.65(m, 3H), 2.42(m, 1H), 4.09(m, 1H), 4.20(m, 1H), 4.95-5.28(m, 3H), 5.43(m, 1H), 5.78(d, J=7.7 Hz, 1H), 7.15-7.38(m, 3H), 7.38-7.62(m, 3H), 7.62-7.78(m, 1H), 7.97(d, J=7.0 Hz, 2H), 8.54(s, 1H)

EXAMPLE 31

Preparation of 2-[(1S, 2S)-1-hydroxy-3-methyl-2-{(S)-4-methyl-2-(4-pyridylmethoxycarbonylamino)valerylamino}butyl]-3-phenylcyclopropenone hydrochloride (compd. No. 99 in Table 1)

mp: 122°-129° C.(dec.) IR(KBr, cm$^{-1}$): 3260, 1858, 1720, 1650, 1640, 1615 NMR(CD$_3$OD, δ): 0.53(d, J=6.6 Hz, 3H), 0.64(d, J=6.5 Hz, 3H), 0.91(d, J=6.7 Hz, 3H), 1.08(d, J=6.7 Hz, 3H), 0.79-1.20(m, 2H), 1.53(m, 1H), 2.10(m, 1H), 4.0-4.18(m, 2H), 5.21(s, 1H), 5.24(d, J=20 Hz, 1H), 5.30(d, J=20 Hz, 1H), 7.53-7.70(m, 3H), 7.95-8.15(m, 4H), 8.82(d, J=6.8 Hz, 2H)

EXAMPLE 32

Preparation of 2-[(1S, 2S)-1-hydroxy-3-methyl-2-{(S)-4-methyl-2-(4-pyridylmethoxycarbonylamino)valerylamino}butyl]-3-phenylcyclopropenone hydrochloride (compd. No. 99 in Table 1)

mp: 116°-134° C.(dec.) IR(KBr, cm$^{-1}$): 3260, 1857, 1720, 1660, 1635, 1620 NMR(CD$_3$OD, δ): 0.82(d, J=6.3 Hz, 6H), 0.84(d, J=6.4 Hz, 6H), 1.53(m, 2H), 1.73(m, 1H), 2.13(m, 1H), 4.0-4.25(m, 2H), 5.05(d, J=7.0 Hz, 1H), 5.32(d, J=17 Hz, 1H), 5.43(d, J=17 Hz, 1H), 7.53-7.70(m, 3H), 7.90-8.10(m, 4H), 8.82(d, J=6.8 Hz, 2H)

EXAMPLE 33

Preparation of 2-[(1S, 2S)-1-hydroxy-3-methyl-2-((S-4-methyl-2-phenoxycarbonylamino)valerylamino]-3-phenylcyclopropenone (compd. No. 102 in Table 1)

mp: 105°-115° C. IR(KBr, cm$^{-1}$): 3304, 1856, 1717, 1657, 1626 NMR(CDCl$_3$, δ): 0.75(d, J=6.1 Hz, 3H), 0.77(d, J=6.3 Hz, 3H), 1.0(d, J=6.6 Hz, 3H), 1.04(d, J=6.7 Hz, 3H), 1.35(m, 2H), 1.56(m, 1H), 2.33(m, 1H), 3.70(m, 1H), 4.17(m, 1H), 5.09(dd, J=8.3 Hz, 4.1 Hz, 1H), 6.17(d, J=9.1 Hz, 1H), 6.21(d, J=8.3 Hz, 1H), 7.02(d, J=7.7 Hz, 2H), 7.16(t, J=7.2 Hz, 1H), 7.30(t, J=7.4 Hz, 2H), 7.42-7.62(m, 3H), 7.70(d, J=7.9 Hz, 1H), 7.94(d, J=6.7 Hz, 2H)

EXAMPLE 34

Preparation of 2-[(1S, 2S)-2-((S)-2-amino-4-methylvalerylamino)-1-hydroxy-3-methylbutyl]-3-phenylcyclopropenone hydrochloride (compd. No. 105 in Table 1)

mp: 147°-153° C.(dec.) IR(KBr, cm$^{-1}$): 3260, 1858, 1675, 1616 NMR(CD$_3$OD, δ): 0.47(d, J=6.5 Hz, 3H), 0.71(d, J=6.5 Hz, 3H), 1.02(d, J=6.7 Hz, 3H), 1.12(d, J=6.7 Hz, 3H), 1.20(m, 2H), 1.42(m, 1H), 2.10(m, 1H), 3.81(dd, J=8.9 Hz, 6.1 Hz, 1H), 4.11(dd, J=9.7 Hz, 2.2 Hz, 1H), 5.23(d, J=2.2 Hz, 1H), 7.55-7.70(m, 3H), 8.03-8.13(m, 2H)

EXAMPLE 35

Preparation of 2-[(1R, 2S)-2-((S)-2-amino-4-methylvalerylamino)-1-hydroxy-3-methylbutyl]-3-phenylcyclopropenone hydrochloride (compd. No. 105 in Table 1)

mp: 133°-136° C. IR(KBr, cm$^{-1}$): 3260, 1860, 1675, 1620 NMR(CD$_3$OD, δ): 0.82(d, J=5.6 Hz, 3H), 0.85(d, J=5.7 Hz, 3H), 1.04(d, J=6.7 Hz, 3H), 1.10(d, J=6.8 Hz, 3H), 1.58-1.80(m, 3H), 2.16(m, 1H), 3.84(m, 1H), 4.03(t, J=7.0 Hz, 1H), 5.18(d, J=6.6 Hz, 1H), 7.55-7.70(m, 3H), 8.07(d, J=6.9 Hz, 2H)

EXAMPLE 36

Preparation of 2-[(1S, 2S)-2-((S)-2-acetylamino-4-methylvalerylamino)-1-hydroxy-3-methylbutyl]-3-phenylcyclopropenone (compd. No. 106 in Table 1)

mp: 94°-105° C. IR(KBr, cm$^{-1}$): 3280, 1858, 1645-1620 NMR(CDCl$_3$, δ): 0.73(d, J=6.3 Hz, 6H), 0.99(d, J=7.1 Hz, 3H), 1.09(d, J=7.0 Hz, 3H), 1.27-1.55(m, 3H), 2.03(s, 3H), 2.28(m, 1H), 3.79(m, 1H), 4.39(m, 1H), 5.14(d, J=3.3 Hz, 1H), 6.22(m, 1H), 6.69(d, J=8.3 Hz, 1H), 7.45-7.60(m, 3H), 7.72(d, J=8.6 Hz, 1H), 7.97(dd, J=8.0 Hz, 1.5 Hz, 2H)

EXAMPLE 37

Preparation of 2-[(1S, 2S)-1-hydroxy-2-((S)-2-isohexanoylamino-4-methylvalerylamino)-3-methylbutyl]-3-phenylcyclopropenone (compd. No. 114 in Table 1)

mp: 148°-151° C. IR(KBr, cm$^{-1}$): 3293, 1856, 1640 NMR(CDCl$_3$, δ): 0.73(d, J=5.9 Hz, 3H), 0.74(d, J=6.0 Hz, 3H), 0.85(d, J=6.2 Hz, 6H), 0.98(d, J=6.7 Hz, 3H), 1.08(d, J=6.6 Hz, 3H), 1.30-1.60(m, 6H), 2.11(t, J=6.7

Hz, 2H), 2.27(m, 1H), 3.83(m, 1H), 4.43(m, 1H), 5.13(dd, J=7.9 Hz, 4.2 Hz, 1H), 6.16(d, J=7.9 Hz, 1H), 6.53(d, J=7.9 Hz, 1H), 7.45–7.55(m, 3H), 7.62(d, J=8.3 Hz, 1H), 7.98(dd, J=7.7 Hz, 1.4 Hz, 2H)

EXAMPLE 38

Preparation of 2-[(1S, 2S)-1-hydroxy-2-((S)-2-lauroylamino-4-methylvalerylamino)-3-methylbutyl]-3-phenylcyclopropenone (compd. No. 120 in Table 1)

mp: 123°–127° C. IR(KBr, cm$^{-1}$): 3293, 1856, 1640 NMR(CDCl$_3$, δ): 0.71(d, J=5.9 Hz, 3H), 0.73(d, J=5.9 Hz, 3H), 0.87(t, J=6.2 Hz, 3H), 0.97(d, J=6.6 Hz, 3H), 1.08(d, J=6.6 Hz, 3H), 1.15–1.45(m, 16H), 1.45–1.80(m, 5H), 2.10(t, J=7.6 Hz, 2H), 2.24(m, 1H), 3.84(m, 1H), 4.42(m, 1H), 5.13(dd, J=7.9 Hz, 3.9 Hz, 1H), 6.22(d, J=8.3 Hz, 1H), 6.64(d, J=7.9 Hz, 1H), 7.42–7.60(m, 3H), 7.67(d, J=8.3 Hz, 1H), 7.98(dd, J=8.0 Hz, 1.7 Hz, 2H)

EXAMPLE 39

Preparation of 2-[(1S, 2S)-2-{(S)-2-{(3-cyclohexylpropionylamino)-4-methylvalerylamino)-1-hydroxy-3-methylbutyl]-3-phenylcyclopropenone (compd. No. 124 in Table 1)

mp: 126°–128° C. IR(KBr, cm$^{-1}$): 3300, 1858, 1640 NMR(CDCl$_3$, δ): 0.74(d, J=6.3 Hz, 3H), 0.75(d, J=6.3 Hz, 3H), 0.70–0.95(m, 2H), 0.98(d, J=7.0 Hz, 3H), 1.08(d, J=7.0 Hz, 3H), 1.05–1.35(m, 4H), 1.35–1.55(m, 5H), 1.55–1.75(m, 5H), 2.11(t, J=8.7 Hz, 2H), 2.27(m, 1H), 3.80(m, 1H), 4.41(m, 1H), 5.13(m, 1H), 6.11(s, 1H), 6.42(d, J=8.5 Hz, 1H), 7.45–7.65(m, 4H), 7.99(dd, J=8.0 Hz, 1.4 Hz, 2H)

EXAMPLE 40

Preparation of 2-[(1S, 2S)-2-((S)-2-cyclohexylcarbonylamino-4-methylvalerylamino)-1-hydroxy-3-methylbutyl]-3-phenylcyclopropenone (compd. No. 129 in Table 1)

mp: 116°–120° C. IR(KBr, cm$^{-1}$): 3297, 1856, 1640 NMR(CDCl$_3$, δ): 0.72(d, J=5.4 Hz, 3H), 0.74(d, J=4.2 Hz, 3H), 0.97(d, J=6.6 Hz, 3H), 1.07(d, J=6.6 Hz, 3H), 0.95–1.55(m, 8H), 1.55–1.80(m, 5H), 2.05(m, 1H), 2.24(m, 1H), 3.83(m, 1H), 4.39(m, 1H), 5.13(dd, J=7.8 Hz, 4.1 Hz, 1H), 6.21(d, J=8.0 Hz, 1H), 6.46(d, J=7.8 Hz, 1H), 7.38–7.55(m, 3H), 7.62(d, J=8.5 Hz, 1H), 7.98(dd, J=7.8 Hz, 1.5 Hz, 2H)

EXAMPLE 41

Preparation of 2-[(1S, 2S)-1-hydroxy-3-methyl-2-((S)-4-methyl-2-phenylacetylaminovalerylamino)butyl]-3-phenylcyclopropenone (compd. No. 132 in Table 1)

mp: 152°–154° C. IR(KBr, cm$^{-1}$): 3280, 1856, 1635 NMR(CDCl$_3$, δ): 0.68(d, J=5.5 Hz, 6H), 0.91(d, J=6.7 Hz, 3H), 1.03(d, J=6.6 Hz, 3H), 1.18–1.43(m, 3H), 2.23(m, 1H), 3.39(d, J=15 Hz, 1H), 3.47(d, J=15 Hz, 1H), 3.72(m, 1H), 4.38(m, 1H), 5.07(m, 1H), 6.03(m, 1H), 6.37(d, J=7.8 Hz, 1H), 7.08–7.19(m, 2H), 7.19–7.30(m, 3H), 7.40–7.60(m, 4H), 7.96(dd, J=7.7 Hz, 1.2 Hz, 2H)

EXAMPLE 42

Preparation of 2-[(1S, 2S)-1-hydroxy-3-methyl-2-{((S)-4-methyl-2-(3-phenylpropionylamino)valerylamino}butyl]-3-phenylcyclopropenone (compd. No. 133 in Table 1)

mp: 148° C. IR(KBr, cm$^{-1}$): 3287, 1854, 1640 NMR(CDCl$_3$, δ): 0.67(d, J=3.9 Hz, 6H), 0.95(d, J=6.8 Hz, 3H), 1.06(d, J=6.8 Hz, 3H), 1.18–1.40(m, 3H), 2.27(m, 1H), 2.43(t, J=7.9 Hz, 2H), 3.70–3.90(m, 2H), 3.74(m, 1H), 4.39(m, 1H), 5.09(m, 1H), 6.19(d, J=8.3 Hz, 1H), 6.59(d, J=8.2 Hz, 1H), 7.07–7.30(m, 5H), 7.40–7.60(m, 4H), 7.96(dd, J=6.6 Hz, 1.7 Hz, 2H)

EXAMPLE 43

Preparation of 2-[(1S, 2S)-1-hydroxy-3-methyl-2-{(S)-4-methyl-2-(4-phenylbutyrylamino)valerylamino}butyl]-3-phenylcyclopropenone (compd. No. 134 in Table 1)

mp: 91°–96° C. IR(KBr, cm$^{31}$ $^1$): 3293, 1856, 1640 NMR(CDCl$_3$, δ): 0.72(d, J=5.1 Hz, 6H), 0.97(d, J=6.6 Hz, 3H), 1.06(d, J=6.5 Hz, 3H), 1.25–1.55(m, 3H), 1.84(m, 2H), 2.11(m, 2H), 2.27(m, 1H), 2.55(t, J=7.5 Hz, 2H), 3.80(m, 1H), 4.42(m, 1H), 5.10(m, 1H), 6.19(d, J=8.1 Hz, 1H), 6.62(d, J=7.7 Hz, 1H), 7.05–7.35(m, 5H), 7.40–7.60(m, 3H), 7.66(d, J=8.3 Hz, 1H), 7.96(d, J=6.4 Hz, 2H)

EXAMPLE 44

Preparation of 2-[(1S, 2S)-1-hydroxy-3-methyl-2-[(S)-4-methyl-2-(4-oxovalerylamino)valerylamino]-3-phenylcyclopropenone (compd. No. 137 in Table 1)

mp: 89°–93° C. IR(KBr, cm$^{-1}$): 3299, 1856, 1719, 1643 NMR(CDCl$_3$, δ): 0.76(d, J=6.1 Hz, 3H), 0.77(d, J=5.8 Hz, 3H), 0.95(d, J=6.7 Hz, 3H), 1.08(d, J=6.6 Hz, 3H), 1.28(m, 1H), 1.48(m, 2H), 2.16(s, 3H), 2.27–2.50(m, 3H), 2.65–2.80(m, 1H), 2.85–3.05(m, 1H), 3.66(m, 1H), 4.35(m, 1H), 5.10(m, 1H), 6.18(d, J=8.5 Hz, 1H), 6.55(d, J=7.6 Hz, 1H), 7.45–7.60(m, 3H), 7.62(d, J=8.0 Hz, 1H), 7.98(dd, J=7.9 Hz, 1.7 Hz, 2H)

EXAMPLE 45

Preparation of 2-[(1S, 2S)-2-{(S)-2-(3-benzoylpropionylamino)-4-methylvalerylamino}-1-hydroxy-3-methylbutyl]-3-phenylcyclopropenone (compd. No. 140 in Table 1)

mp: 83°–88° C. IR(KBr, cm$^{-1}$): 3292, 1856, 1684, 1641 NMR(CDCl$_3$, δ): 0.78(d, J=6.1 Hz, 3H), 0.79(d, J=5.9 Hz, 3H), 0.90(d, J=6.7 Hz, 3H), 1.05(d, J=6.6 Hz, 3H), 1.31(m, 1H), 1.48–1.68(m, 2H), 2.40(m, 1H), 2.54(m, 2H), 3.22–3.48(m, 1H), 3.42–3.75(m, 2H), 4.38(m, 1H), 5.05(m, 1H), 6.09(m, 1H), 6.57(d, J=7.5 Hz, 1H), 7.35–7.60(m, 6H), 7.74(d, J=7.8 Hz, 1H), 7.90–8.05(m, 4H)

EXAMPLE 46

Preparation of 2-[(1S, 2S)-2-{(S)-2-(3-ethoxycarbonylpropionylamino)-4-methylvalerylamino}-1-hydroxy-3-methylbutyl]-3-phenylcyclopropenone (compd. No. 142 in Table 1)

mp: 111°–112° C. IR(KBr, cm$^{-1}$): 3293, 1856, 1738, 1643 NMR(CDCl$_3$, δ): 0.70–0.90(m, 6H), 0.97(d, J=6.6 Hz, 3H), 1.08(d, J=6.6 Hz, 3H), 1.15–1.35(m, 1H), 1.25(t, J=7.2 Hz, 3H), 1.40–1.60(m, 2H), 2.30–2.65(m, 4H), 2.70–2.90(m, 1H), 3.57(m, 1H), 4.09(m, 2H), 4.39(m, 1H), 5.09(m, 1H), 6.12(s, 1H), 6.47(d, J=7.1 Hz, 1H), 7.45-7.60(m, 3H), 7.66(d, J=7.5 Hz, 1H), 7.99(dd, J=7.5 Hz, 1.0 Hz, 2H) 2H)

EXAMPLE 47

Preparation of 2-[(1S, 2S)-1-hydroxy-3-methyl-2-((S)-4-methyl-2-succinylaminovalerylamino)butyl]-3-phenylcyclopropenone (compd. No. 143 in Table 1)

mp: 104°-106° C.(dec.) IR(KBr, cm⁻¹): 3297, 1858, 1719, 1650, 1630 NMR(CD₃OD, δ): 0.56(d, J=6.7 Hz, 3H), 0.63(d, J=6.7 Hz, 3H), 0.97(d, J=6.9 Hz, 3H), 1.08(d, J=6.8 Hz, 3H), 1.05-1.33(m, 2H), 1.40(m, 1H), 2.09(m, 1H), 2.35-2.60(m, 4H), 4.0(m, 1H), 4.22(m, 1H), 5.20(d, J=2.9 Hz, 1H), 7.47-7.65(m, 3H), 7.90-8.10(m, 3H)

EXAMPLE 48

Preparation of 2-[(1S, 2S)-1-hydroxy-3-methyl-2-((S)-4-methyl-2-phenoxyacetylaminovalerylamino)butyl]-3-phenylcyclopropenone (compd. No. 148 in Table 1)

mp: 138°-139° C. IR(KBr, cm⁻¹): 3290, 1856, 1648, 1620 NMR(CDCl₃, δ): 0.78(d, J=5.8 Hz, 6H), 1.02(d, J=6.7 Hz, 3H), 1.09(d, J=6.6 Hz, 3H), 1.30-1.60(m, 3H), 2.38(m, 1H), 3.64(m, 1H), 4.26(d, J=15 Hz, 1H), 4.37(d, J=15 Hz, 1H), 4.49(m, 1H), 5.14(m, 1H), 6.12(m, 1H), 6.84(d, J=8.8 Hz, 2H), 6.90(d, J=8.8 Hz, 1H), 7.01(t, J=7.4 Hz, 1H), 7.25-7.38(m, 2H), 7.38-7.53(m, 3H), 7.66(d, J=7.6 Hz, 1H), 7.85-7.98(m, 2H)

EXAMPLE 49

Preparation of 2-[(1R, 2S)-1-hydroxy-3-methyl-2-((S)-4-methyl-2-phenoxyacetylaminovalerylamino)butyl]-3-phenylcyclopropenone (compd. No. 148 in Table 1)

mp: 74°-84° C. IR(KBr, cm⁻¹): 3300, 1859, 1658, 1627 NMR(CDCl₃, δ): 0.64(d, J=6.3 Hz, 6H), 1.06(d, J=6.6 Hz, 3H), 1.15(d, J=6.7 Hz, 3H), 1.30-1.65(m, 3H), 2.14(m, 1H), 4.03(m, 1H), 4.39(d, J=15 Hz, 1H), 4.47(d, J=15 Hz, 1H), 4.51(m, 1H), 5.15(dd, J=6.6 Hz, 2.8 Hz, 1H), 5.26(d, J=6.6 Hz, 1H), 6.85-6.95(m, 3H), 7.02(t, J=7.4 Hz, 1H), 7.20-7.40(m, 3H), 7.45-7.60(m, 3H), 8.01(dd, J=7.8 Hz, 1.3 Hz, 2H)

EXAMPLE 50

Preparation of 2-[(1S, 2S)-2-{(S)-2-(2-chlorophenoxyacetylamino)-4-methylvalerylamino}-1-hydroxy-3-methylbutyl]-3-phenylcyclopropenone (compd. No. 152 in Table 1)

mp: 101° C. IR(KBr, cm⁻¹): 3287, 1856, 1653, 1624 NMR(CDCl₃, δ): 0.80(d, J=5.2 Hz, 3H), 0.82(d, J=5.1 Hz, 3H), 1.03(d, J=6.6 Hz, 3H), 1.10(d, J=6.6 Hz, 3H), 1.35-1.60(m, 3H), 2.38(m, 1H), 3.68(m, 1H), 4.30(d, J=15 Hz, 1H), 4.40(d, J=15 Hz, 1H), 4.45(m, 1H), 5.14(dd, J=7.8 Hz, 4.1 Hz, 1H), 6.17(d, J=8.4 Hz, 1H), 6.81(d, J=8.2 Hz, 1H), 6.97(t, J=7.7 Hz, 1H), 7.07(d, J=7.7 Hz, 1H), 7.22(t, J=7.6 Hz, 1H), 7.32-7.48(m, 4H), 7.71(d, J=7.7 Hz, 1H), 7.85-7.95(m, 2H)

EXAMPLE 51

Preparation of 2-[(1S, 2S)-2-{(S)-2-(4-chlorophenoxyacetylamino)-4-methylvalerylamino}-1-hydroxy-3-methylbutyl]-3-phenylcyclopropenone (compd. No. 154 in Table 1)

mp: 88°-90° C. IR(KBr, cm⁻¹): 3295, 1856, 1653, 1624 NMR(CDCl₃, δ): 0.79(d, J=3.7 Hz, 6H), 1.02(d, J=6.6 Hz, 3H), 1.10(d, J=6.6 Hz, 3H), 1.33-1.60(m, 3H), 2.36(m, 1H), 3.65(m, 1H), 4.21(d, J=15 Hz, 1H), 4.34(d, J=15 Hz, 1H), 4.51(m, 1H), 5.14(dd, J=8.3 Hz, 4.1 Hz, 1H), 6.12(d, J=8.3 Hz, 1H), 6.78(d, J=8.9 Hz, 2H), 6.88(d, J=8.3 Hz, 1H), 7.24(d, J=8.9 Hz, 2H), 7.35-7.55(m, 3H), 7.69(d, J=8.0 Hz, 1H), 7.90(dd, J=6.6 Hz, 2.5 Hz, 2H)

EXAMPLE 52

Preparation of 2-[(1S, 2S)-2-{(S)-2-(2,3-dichlorophenoxyacetylamino)-4-methylvalerylamino}-1-hydroxy-3-methylbutyl]-3-phenylcyclopropenone (compd. No. 155 in Table 1)

mp: 121°-123° C. IR(KBr, cm⁻¹): 3291, 1856, 1651, 1624 NMR(CDCl₃, δ): 0.81(d, J=5.0 Hz, 3H), 0.83(d, J=5.1 Hz, 3H), 1.03(d, J=6.6 Hz, 3H), 1.11(d, J=6.6 Hz, 3H), 1.38-1.63(m, 3H), 2.38(m, 1H), 3.67(m, 1H), 4.31(d, J=14 Hz, 1H), 4.40(d, J=14 Hz, 1H), 4.45(m, 1H), 5.15(dd, J=8.3 Hz, 4.0 Hz, 1H), 6.20(d, J=8.3 Hz, 1H), 6.73(m, 1H), 7.03(d, J=8.3 Hz, 1H), 7.07-7.22(m, 2H), 7.35-7.55(m, 3H), 7.74(d, J=8.2 Hz, 1H), 7.88(d, J=5.2 Hz, 2H)

EXAMPLE 53

Preparation of 2-[(1S, 2S)-1-hydroxy-2-{(S)-2-(2-methoxyphenoxyacetylamino)-4-methylvalerylamino}-3-methylbutyl]-3-phenylcyclopropenone (compd. No. 161 in Table 1)

mp: 106°-108° C. IR(KBr, cm⁻¹): 3278, 1854, 1672, 1645 NMR(CDCl₃, δ): 0.70-0.85(m, 6H), 0.96(d, J=6.7 Hz, 3H), 1.05(d, J=6.6 Hz, 3H), 1.30-1.55(m, 3H), 2.36(m, 1H), 3.57(m, 1H), 3.84(s, 3H), 4.41(m, 1H), 4.41(d, J=15 Hz, 1H), 4.49(d, J=15 Hz, 1H), 5.10(dd, J=7.3 Hz, 4.6 Hz, 1H), 6.08(d, J=8.2 Hz, 1H), 6.82-6.95(m, 3H), 6.95-7.08(m, 1H), 7.33-7.57(m, 5H), 7.94(dd, J=6.1 Hz, 1.7 Hz, 2H)

EXAMPLE 54

Preparation of 2-[(1S, 2S)-2-((S)-2-benzyloxyacetylamino-4-methylvalerylamino)-1-hydroxy-3-methylbutyl]-3-phenylcyclopropenone (compd. No. 166 in Table 1)

mp: 59°-69° IR(KBr, cm⁻¹): 3293, 1856, 1651, 1623 NMR(CDCl₃, δ): 0.65-0.85(m, 6H), 0.99(d, J=6.6 Hz, 3H), 1.06(d, J=6.6 Hz, 3H), 1.30-1.60(m, 3H), 2.29(m, 1H), 3.75(m, 1H), 3.76(d, J=15 Hz, 1H), 3.88(d, J=15 Hz, 1H), 4.30-4.55(m, 3H), 5.08(m, 1H), 6.12(m, 1H), 6.95(d, J=8.4 Hz, 1H), 7.20-7.40(m, 5H), 7.40-7.60(m, 3H), 7.69(d, J=8.1 Hz, 1H), 7.93(d, J=6.5 Hz, 2H)

EXAMPLE 55

Preparation of 2-[(1S, 2S)-1-hydroxy-3-methyl-2{(S)-4-methyl-2-(3-phenoxypropionylamino)valerylamino}butyl]-3-phenylcyclopropenone (compd. No. 167 in Table 1)

mp: 92°-95° C. IR(KBr, cm⁻¹): 3291, 1856, 1643, 1605 NMR(CDCl₃, δ): 0.73(d, J=6.3 Hz, 6H), 0.89(d, J=6.7 Hz, 3H), 0.99(d, J=6.6 Hz, 3H), 1.25-1.58(m,

3H), 2.31(m, 1H), 2.59(t, J=4.0 Hz, 2H), 3.51(m, 1H), 4.16(m, 2H), 4.41(m, 1H), 5.07(dd, J=8.1 Hz, 4.2 Hz, 1H), 6.28(d, J=8.3 Hz, 1H), 6.69(d, J=8.1 Hz, 1H), 6.87(d, J=8.7 Hz, 2H), 6.95(t, J=7.6 Hz, 1H), 7.19-7.35(m, 2H), 7.40-7.60(m, 4H), 7.96(dd, J=6.8 Hz, 1.4 Hz, 2H)

EXAMPLE 56 preparation of 2-[(1S, 2S)-1-hydroxy-3-methyl-2-((S)-4-methyl-2-phenylthioacetylaminovalerylamino}butyl]-3-phenylcyclopropenone (compd. No. 168 in Table 1)

mp: 133° C. IR(KBr, cm$^{-1}$): 3287, 1854, 1643, 1625 NMR(CDCl$_3$, δ): 0.55–0.80(m, 6H), 0.93(d, J=6.6 Hz, 3H), 1.06(d, J=6.6 Hz, 3H), 1.05–1.40(m, 3H), 2.28(m, 1H), 3.43(d, J=17 Hz, 1H), 3.58(d, J=17 Hz, 1H), 3.62(m, 1H), 4.33(m, 1H), 5.11(dd, J=8.3 Hz, 4.1 Hz, 1H), 6.15(m, 1H), 7.08–7.35(m, 6H), 7.35–7.60(m, 4H), 7.95(dd, J=7.5 Hz, 1.6 Hz, 2H)

EXAMPLE 57

Preparation of 2-[(1S, 2S)-1-hydroxy-3-methyl-2-{(S)-4-methyl-2-(3-phenylsulfonylpropionylamino)-valerylamino}butyl]-3-phenylcyclopropenone (compd. No. 170 in Table 1)

mp: 100°–106° C. IR(KBr, cm$^{-1}$): 3295, 1856, 1644 NMR(CDCl$_3$, δ): 0.74(d, J=4.2 Hz, 6H), 0.99(d, J=6.8 Hz, 3H), 1.07(d, J=6.8 Hz, 1.25–1.65(m, 3H), 2.38(m, 1H), 2.69(m, 2H), 3.27–3.43(m, 1H), 3.43–3.65(m, 2H), 4.37(m, 1H), 5.14(dd, J=8.9 Hz, 5.0 Hz, 1H), 6.18(d, J=8.9 Hz, 1H), 7.18(d, J=7.6 Hz, 1H), 7.40–7.60(m, 5H), 7.67(t, J=7.4 Hz, 2H), 7.90(d, J=7.2 Hz, 2H), 7.98(d, J=6.4 Hz, 2H)

EXAMPLE 58

Preparation of 2-[(1S, 2S)-2-((S)-2-benzoylamino-4-methylvalerylamino)-1-hydroxy-3-methylbutyl]-3-phenylcyclopropenone (compd. No. 171 in Table 1)

mp: 150°–154° C. IR(KBr, cm$^{-1}$): 3297, 1856, 1632 NMR(CDCl$_3$, δ): 0.63–0.80(m, 6H), 0.91(d, J=6.5 Hz, 3H), 0.93(d, J=6.5 Hz, 3H), 1.35–1.65(m, 3H), 2.22(m, 1H), 3.42(m, 1H), 4.48(m, 1H), 4.78(m, 1H), 6.23(d, J=7.8 Hz, 1H), 7.28–7.55(m, 6H), 7.60–7.68(m, 3H), 7.81(d, J=8.2 Hz, 1H), 7.85–7.95(m, 2H)

EXAMPLE 59

Preparation of 2-[(1S, 2S)-2-{(S)-2-(2,6-difluorobenzoylamino)-4-methylvalerylamino}-1-hydroxy-3-methylbutyl]-3-phenylcyclopropenone (compd. No. 175 in Table 1)

mp: 111°–122° C. IR(KBr, cm$^{-1}$): 3300, 1858, 1647, 1626 NMR(CDCl$_3$, δ): 0.72(d, J=6.3 Hz, 3H), 0.74(d, J=6.2 Hz, 3H), 1.04(d, J=6.8 Hz, 3H), 1.10(d, J=6.7 Hz, 3H), 1.30–1.65(m, 3H), 2.33(m, 1H), 3.73(m, 1H), 4.57(m, 1H), 5.01(d, J=4.0 Hz, 1H), 6.82(dd, J=8.0 Hz, 7.9 Hz, 2H), 7.26(m, 1H), 7.37–7.55(m, 4H), 7.64(d, J=8.3 Hz, 1H), 7.91(d, J=6.7 Hz, 2H)

EXAMPLE 60

Preparation of 2-[(1S, 2S)-2-{(S)-2-(2-chlorobenzoylamino)-4-methyl-valerylamino}-1-hydroxy-3-methylbutyl]-3-phenylcyclopropenone (compd. No. 178 in Table 1)

mp: 99°–104° C. IR(KBr, cm$^{-1}$): 3297, 1856, 1637 NMR(CDCl$_3$, δ): 0.76(d, J=5.7 Hz, 3H), 0.78(d, J=5.1 Hz, 3H), 1.04(d, J=6.6 Hz, 3H), 1.09(d, J=6.6 Hz, 3H), 1.38–1.65(m, 3H), 2.32(m, 1H), 3.72(m, 1H), 4.59(m, 1H), 5.05(dd, J=8.4 Hz, 4.3 Hz, 1H), 6.14(d, J=8.4 Hz, 1H), 7.05–7.35(m, 4H), 7.35–7.58(m, 4H), 7.71(d, J=8.2 Hz, 1H), 7.91(d, J=6.7 Hz, 2H)

EXAMPLE 61

Preparation of 2-[(1S, 2S)-2-{(S)-2-(3-chlorobenzoylamino)-4-methyl-valerylamino}-1-hydroxy-3-methylbutyl]-3-phenylcyclopropenone (compd. No. 179 in Table 1)

mp: 179° C. IR(KBr, cm$^{-1}$): 3297, 1856, 1634 NMR(CDCl$_3$, δ): 0.71(d, J=6.2 Hz, 3H), 0.74(d, J=6.4 Hz, 3H), 0.90(d, J=6.7 Hz, 3H), 0.93(d, J=8.8 Hz, 3H), 1.30–1.70(m, 3H), 2.19(m, 1H), 3.44(m, 1H), 4.46(m, 1H), 4.83(m, 1H), 6.20(m, 1H), 7.15–7.35(m, 1H), 7.35–7.55(m, 4H), 7.64(d, J=7.7 Hz, 1H), 7.75(s, 1H), 7.80–8.03(m, 4H)

EXAMPLE 62

Preparation of 2-[(1S, 2S)-2-{(S)-2-(4-chlorobenzoylamino)-4-methyl-valerylamino}-1-hydroxy-3-methylbutyl]-3-phenylcyclopropenone (compd. No. 180 in Table 1)

mp: 116°–120° C. IR(KBr, cm$^{-1}$): 3297, 1856, 1631 NMR(CDCl$_3$, δ): 0.71(d, J=5.5 Hz, 3H), 0.73(d, J=5.4 Hz, 3H), 0.89(d, J=6.6 Hz, 3H), 0.95(d, J=6.6 Hz, 3H), 1.30–1.65(m, 3H), 2.21(m, 1H), 3.51(m, 1H), 4.49(m, 1H), 4.87(m, 1H), 6.26(d, J=8.6 Hz, 1H), 7.28(d, J=7.5 Hz, 2H), 7.38–7.58(m, 3H), 7.67(d, J=7.5 Hz, 2H), 7.70–7.95(m, 4H)

EXAMPLE 63

Preparation of 2-[(1S, 2S)-1-hydroxy-3-methyl-2-{(S)-4-methyl-2-(2-toluoylamino)valerylamino}butyl]-3-phenylcyclopropenone (compd. No. 184 in Table 1)

mp: 101°–105° C. IR(KBr, cm$^{-1}$): 3295, 1856, 1656 NMR(CDCl$_3$, δ): 0.75(d, J=5.9 Hz, 3H), 0.76(d, J=5.8 Hz, 3H), 1.02(d, J=6.7 Hz, 3H), 1.06(d, J=6.7 Hz, 3H), 1.40–1.65(m, 3H), 2.25(m, 1H), 2.30(s, 3H), 3.66(m, 1H), 4.52(m, 1H), 4.88(dd, J=8.9 Hz, 4.0 Hz, 1H), 6.14(d, J=8.9 Hz, 1H), 7.01–7.08(m, 3H), 7.08–7.32(m, 2H), 7.38–7.60(m, 3H), 7.78(d, J=7.1 Hz, 1H), 7.87(dd, J=8.2 Hz, 1.5 Hz, 2H)

EXAMPLE 64

Preparation of 2-[(1S, 2S)-1-hydroxy-2-{2-(4-methoxybenzoylamino)-4-methylvalerylamino}-3-methylbutyl]-3-phenylcyclopropenone (compd. No. 190 in Table 1)

IR(KBr, cm$^{-1}$): 3297, 1856, 1628 NMR(CDCl$_3$, δ): 0.62–0.90(m, 6H), 0.90–1.05(m, 6H), 1.30–1.60(m, 3H), 2.21(m, 1H), 3.46(m, 1H), 3.80(s, 3H), 4.49(m, 1H), 4.70–4.95(m, 1H), 6.20–6.50(m, 1H), 6.83(d, J=8.9 Hz, 2H), 7.33–7.58(m, 4H), 7.68–7.95(m, 3H), 7.87(d, J=7.8 Hz, 2H)

EXAMPLE 65

Preparation of 2-[(1S, 2S)-1-hydroxy-2-{(S)-2-(4-methoxycarbonylbenzoylamino)-4-methylvalerylamino}-3-methylbutyl]-3-phenylcyclopropenone (compd. No. 191 in Table 1)

mp: 125°–128° C. IR(KBr, cm$^{-1}$): 3301, 1856, 1728, 1634 NMR(CDCl$_3$, δ): 0.71(d, J=5.5 Hz, 3H), 0.73(d, J=5.3 Hz, 3H), 0.89(d, J=6.9 Hz, 3H), 0.93(d, J=7.0

Hz, 3H), 1.33–1.65(m, 3H), 2.18(m, 1H), 3.51(m, 1H), 3.92(s, 3H), 4.52(m, 1H), 4.84(dd, J=8.9 Hz, 3.5 Hz, 1H), 6.25(d, J=8.9 Hz, 1H), 7.35–7.55(m, 3H), 7.76(d, J=8.3 Hz, 2H), 7.85–8.03(m, 6H)

EXAMPLE 66

Preparation of 2-[(1S, 2S)-2-{(S)-2-(1-acetyl-4-piperidyl)carbonylamino-4-methylvalerylamino}-1-hydroxy-3-methylbutyl]-3-phenylcyclopropenone (compd. No. 196 in Table 1)

mp: 120°–124° C. IR(KBr, cm$^{-1}$): 3300, 1860, 1630 NMR(CDCl$_3$, δ): 0.72(d, J=2.7 Hz, 6H), 0.96(d, J=6.6 Hz, 3H), 1.08(d, J=6.9 Hz, 3H), 1.30–1.90(m, 7H), 2.06(s, 3H), 1.95–2.40(m, 2H), 2.55(m, 1H), 3.01(m, 1H), 3.70–3.93(m, 2H), 4.35–4.60(m, 2H), 5.14(m, 1H), 6.15(m, 1H), 6.70(t, J=8.8 Hz, 1H), 7.43–7.65(m, 4H), 7.97(d, J=6.8 Hz, 2H)

EXAMPLE 67

Preparation of 2-[(1S, 2S)-2-{(S)-2-(2-furoylamino)-4-methylvalerylamino}-1-hydroxy-3-methylbutyl]-3-phenylcyclopropenone (compd. No. 197 in Table 1)

mp: 101°–105° C. IR(KBr, cm$^{-1}$): 3300, 1857, 1640 NMR(CDCl$_3$, δ): 0.80(d, J=5.8 Hz, 6H), 1.01(d, J=7.1 Hz, 3H), 1.08(d, J=7.0 Hz, 3H), 1.40–1.65(m, 3H), 2.37(m, 1H), 3.67(m, 1H), 4.58(m, 1H), 5.14(d, J=4.4 Hz, 1H), 6.43(dd, J=3.7 Hz, 1.8 Hz, 1H), 6.79(d, J=8.7 Hz, 1H), 7.01(d, J=3.7 Hz, 1H), 7.35(d, J=1.8 Hz, 1H), 7.40–7.55(m, 3H), 7.78(d, J=8.2 Hz, 1H), 7.91(dd, J=8.1 Hz, 1.5 Hz, 2H)

EXAMPLE 68

Preparation of 2-[(1S, 2S)-1-hydroxy-3-methyl-2-{(S)-4-methyl-2-(2-thenoylamino)valerylamino}butyl]-3-phenylcyclopropenone (compd. No. 200 in Table 1)

mp: 171°–172° C. IR(KBr, cm$^{-1}$): 3301, 1856, 1665, 1624 NMR(CDCl$_3$, δ): 0.69(d, J=6.9 Hz, 3H), 0.72(d, J=6.6 Hz, 3H), 0.87(d, J=6.6 Hz, 3H), 0.92(d, J=6.6 Hz, 3H), 1.30–1.70(m, 3H), 2.15(m, 1H), 3.62(m, 1H), 4.48(m, 1H), 4.94(dd, J=8.4 Hz, 3.1 Hz, 1H), 6.34(d, J=8.4 Hz, 1H), 6.99(dd, J=4.5 Hz, 4.3 Hz, 1H), 7.38–7.62(m, 4H), 7.66(dd, J=3.5 Hz, 1H), 7.68–8.03(m, 4H)

EXAMPLE 69

Preparation of 2-[(1S, 2S)-2-{(S)-2-(1,3-dimethyl-5-pyrazolylcarbonylamino)-4-methylvalerylamino}-1-hydroxy-3-methylbutyl]-3-phenylcyclopropenone (compd. No. 203 in Table 1)

mp: 115°–118° C. IR(KBr, cm$^{-1}$): 3289, 1856, 1636 NMR(CDCl$_3$, δ): 0.80(d, J=5.9 Hz, 3H), 0.82(d, J=6.0 Hz, 3H), 1.01(d, J=6.7 Hz, 3H), 1.06(d, J=6.7 Hz, 3H), 1.42–1.60(m, 3H), 2.20(s, 3H), 2.37(m, 1H), 3.54(m, 1H), 4.00(s, 3H), 4.50(m, 1H), 5.06(m, 1H), 6.03(s, 1H), 6.27(s, 1H), 6.80(d, J=8.3 Hz, 1H), 7.43–7.54(m, 3H), 7.58(d, J=7.8 Hz, 1H), 7.89(dd, J=7.8 Hz, 1.5 Hz, 2H)

EXAMPLE 70

Preparation of 2-[(1S, 2S)-1-hydroxy-3-methyl-2-{(S)-4-methyl-2-(6-methyl-2-pyridylcarbonylamino)-valerylamino}butyl]-3-phenylcyclopropenone (compd. No. 207 in Table 1)

mp: 98°–100° C. IR(KBr, cm$^{-1}$): 3314, 1856, 1655 NMR(CDCl$_3$, δ): 0.81(d, J=5.7 Hz, 3H), 0.82(d, J=5.9 Hz, 3H), 1.02(d, J=6.7 Hz, 3H), 1.08(d, J=6.7 Hz, 3H), 1.56(m, 3H), 2.42(m, 1H), 2.49(s, 3H), 3.67(m, 1H), 4.56(m, 1H), 5.18(m, 1H), 6.33(d, J=7.8 Hz, 1H), 7.22(d, J=7.5 Hz, 1H), 7.36–7.44(m, 3H), 7.64(dd, J=7.7 Hz, 7.7 Hz, 1H), 7.77–7.90(m, 4H), 8.22(d, J=4.1 Hz, 1H)

EXAMPLE 71

Preparation of 2-[(1S, 2S)-1-hydroxy-3-methyl-2-((S)-4-methyl-2-nicotinoylaminovalerylamino)butyl]-3-phenylcyclopropenone (compd. No. 209 in Table 1)

mp: 108°–115° C.(dec.) IR(KBr, cm$^{-1}$): 3299, 1856, 1642 NMR(CDCl$_3$, δ): 0.63–0.80(m, 6H), 0.92(d, J=6.7 Hz, 3H), 0.96(d, J=6.8 Hz, 3H), 1.34–1.72(m, 3H), 2.23(m, 1H), 3.58(m, 1H), 4.59(m, 1H), 5.30(m, 1H), 6.58(m, 1H), 7.25(m, 1H), 7.35–7.55(m, 3H), 7.92(dd, J=6.7 Hz, 1.4 Hz, 2H), 8.02–8.18(m, 2H), 8.32(m, 1H), 8.59(dd, J=4.8 Hz, 1.5 Hz, 1H), 9.11(d, J=1.5 Hz, 1H)

EXAMPLE 72

Preparation of 2-[(1S, 2S)-1-hydroxy-2-((S)-2-isonicotinoylamino-4-methylvalerylamino)-3-methylbutyl]-3-phenylcyclopropenone (compd. No. 213 in Table 1)

mp: 202°–203° C.(dec.) IR(KBr, cm$^{-1}$): 3299, 1856, 1647, 1625 NMR(CD$_3$OD, δ): 0.54(d, J=6.4 Hz, 3H), 0.69(d, J=6.4 Hz, 3H), 1.01(d, J=6.7 Hz, 3H), 1.12(d, J=6.6 Hz, 3H), 0.95–1.60(m, 3H), 2.12(m, 1H), 4.07(m, 1H), 4.55(m, 1H), 5.24(d, J=2.2 Hz, 1H), 7.45–7.70(m, 3H), 8.07(d, J=8.0 Hz, 2H), 8.33(d, J=6.8 Hz, 2H), 8.44(d, J=9.7 Hz, 1H), 9.57(d, J=6.8 Hz, 2H)

EXAMPLE 73

Preparation of 2-[(1S, 2S)-2-{(S)-2-(2-chloroisonicotinoylamino)-4-methylvalerylamino}-1-hydroxy-3-methylbutyl]-3-phenylcyclopropenone (compd. No. 216 in Table 1)

mp: 136°–138° C.(dec.) IR(KBr, cm$^{-1}$): 3299, 1856, 1643 NMR(CDCl$_3$, δ): 0.76(d, J=6.4 Hz, 3H), 0.79(d, J=6.6 Hz, 3H), 0.95(d, J=6.7 Hz, 3H), 1.02(d, J=6.6 Hz, 3H), 1.40–1.63(m, 3H), 2.26(m, 1H), 3.50(m, 1H), 4.51(m, 1H), 5.00(d, J=3.5 Hz, 1H), 6.03(s, 1H), 7.43–7.53(m, 4H), 7.62(d, J=0.6 Hz, 1H), 7.75(m, 2H), 7.90(dd, J=7.9 Hz, 1.3 Hz, 2H), 8.41(d, J=5.2 Hz, 1H)

EXAMPLE 74

Preparation of 2-[(1S, 2S)-1-hydroxy-3-methyl-2-{(S)-4-methyl-2-(2-quinolylcarbonylamino)valerylamino}butyl-3-phenylcyclopropenone hydrochloride (compd. No. 219 in Table 1)

mp: 156°–157° C.(dec.) IR(KBr, cm$^{-1}$): 3252, 1854, 1684, 1620 NMR(CD$_3$OD, δ): 0.60(d, J=6.4 Hz, 3H), 0.74(d, J=6.4 Hz, 3H), 1.02(d, J=6.7 Hz, 3H), 1.12(d, J=6.6 Hz, 3H), 1.08–1.33(m, 1H), 1.52(m, 2H), 2.15(m, 1H), 4.09(dd, J=9.8 Hz, 2.4 Hz, 1H), 4.66(m, 1H), 5.25(d, J=2.3 Hz, 1H), 7.40–7.58(m, 3H), 7.92(m, 1H), 8.02–8.17(m, 3H), 8.26(d, J=8.3 Hz, 1H), 8.36(dd, J=8.6 Hz, 1.6 Hz, 9.02(d, J=8.5 Hz, 1H)

EXAMPLE 75

Preparation of 2-[(1S, 2S)-2-{(S)-2-(3-benzylureido)-4-methylvalerylamino}-1-hydroxy-3-methylbutyl]-3-phenylcyclopropenone (compd. No. 225 in Table 1)

mp: 160° C. IR(KBr, cm$^{-1}$): 3308, 1856, 1628 NMR(CD$_3$OD, δ): 0.53(d, J=6.6 Hz, 3H), 0.62(d,

J=6.5 Hz, 3H), 0.95(d, J=6.7 Hz, 3H), 1.08(d, J=6.7 Hz, 3H), 0.95-1.25(m, 2H), 1.39(m, 1H), 2.07(m, 1H), 4.01(dd, J=9.5 Hz, 2.4 Hz, 1H), 4.13(dd, J=9.9 Hz, 4.9 Hz, 1H), 4.20(d, J=14 Hz, 1H), 4.26(d, J=14 Hz, 1H), 5.19(d, J=2.4 Hz, 1H), 7.13-7.33(m, 5H), 7.50-7.70(m, 3H), 7.07(dd, J=7.6 Hz, 1.8 Hz, 2H)

EXAMPLE 76

Preparation of 2-[(1S, 2S)-1-hydroxy-3-methyl-2-{(S)-4-methyl-2-(3-phenylureido)valerylamino)}butyl]-3-phenylcyclopropenone (compd. No. 227 in Table 1)

mp: 165°-169° C.(dec.) IR(KBr, cm$^{-1}$): 3318, 1856, 1645, 1620 NMR(CD$_3$OD, δ): 0.55(d, J=6.6 Hz, 3H), 0.66(d, J=6.5 Hz, 3H), 0.99(d, J=6.7 Hz, 3H), 1.10(d, J=6.7 Hz, 3H), 1.0-1.35(m, 2H), 1.48(m, 1H), 2.11(m, 1H), 4.03(dd, J=9.6 Hz, 2.4 Hz, 1H), 4.20(dd, J=10 Hz, 5.0 Hz, 1H), 5.22(d, J=2.4 Hz, 1H), 6.94(t, J=7.2 Hz, 1H), 7.15-7.33(m, 4H), 7.50-7.67(m, 3H), 8.07(dd, J=8.2 Hz, 1.8 Hz, 2H)

EXAMPLE 77

Preparation of 2-[(1S, 2S)-1-hydroxy-3-methyl-2-((S)-4-methyl-2-propylsulfonylaminovalerylamino)butyl]-3-phenylcyclopropenone (compd. No. 232 in Table 1)

mp: 195°-196° C. IR(KBr, cm$^{-1}$): 3450, 3250, 1858, 1823, 1663, 1630 NMR(DMSO-d6): 0.37(d, J=6.9 Hz, 3H), 0.58(d, J=7.4 Hz, 3H), 0.70-1.15(m, 8H), 1.03(d, J=7.0 Hz, 3H), 1.50-1.80(m, 3H), 1.96(m, 1H), 2.72(m, 2H), 3.82(m, 1H), 3.93(m, 1H), 5.11(m, 1H), 6.34(d, J=5.4 Hz, 1), 7.14(d, J=10 Hz, 1H), 7.50-7.65(m, 3H), 7.93(d, J=7.4 Hz, 2H), 8.08(d, J=10 Hz, 1H)

EXAMPLE 78

Preparation of 2-[(1S, 2S)-2-((S)-2-benzylsulfonylamino-4-methylvalerylamino)-1-hydroxy-3-methylbutyl]-3-phenylcyclopropenone (compd. No. 237 in Table 1)

mp: 197° C.(dec.) IR(KBr, cm$^{-1}$): 3314, 1856, 1678, 1624 NMR(DMSO-d6): 0.39(d, J=6.6 Hz, 3H), 0.57(d, J=6.5 Hz, 3H), 0.78-1.0(m, 2H), 0.95(d, J=6.7 Hz, 3H), 1.04(d, J=6.6 Hz, 3H), 1.42(m, 1H), 1.99(m, 1H), 3.83-4.07(m, 2H), 4.05(d, J=14 Hz, 1H), 4.14(d, J=14 Hz, 1H), 5.14(m, 1H), 6.38(m, 1H), 7.33(s, 5H), 7.20-7.45(m, 1H), 7.53-7.73(m, 3H), 7.94(dd, J=7.1 Hz, 1.5 Hz, 2H), 8.14(d, J=9.4 Hz, 1H)

EXAMPLE 79

Preparation of 2-[(1R, 2S)-2-((S)-2-benzylsulfonylamino-4-methylvalerylamino)-1-hydroxy-3-methylbutyl]-3-phenylcyclopropenone (compd. No. 237 in Table 1)

mp: 122°-124° C. IR(KBr, cm$^{-1}$): 3280, 1858, 1662, 1625 NMR(CDCl$_3$, δ): 0.66(d, J=6.4 Hz, 3H), 0.69(d, J=6.3 Hz, 3H), 0.87(m, 1H), 1.10(d, J=6.6 Hz, 3H), 1.14(d, J=6.7 Hz, 3H), 1.47(m, 2H), 2.17(m, 1H), 3.77(m, 1H), 4.08-4.23(m, 3H), 4.92(d, J=6.4 Hz, 1H), 5.14(m, 1H), 5.60(d, J=8.5 Hz, 1H), 7.18(d, J=8.3 Hz, 1H), 7.31(s, 5H), 7.41(t, J=7.6 Hz, 2H), 7.53(t, J=7.2 Hz, 1H), 7.93(d, J=7.2 Hz, 2H)

EXAMPLE 80

Preparation of 2-[(1S, 2S)-1-hydroxy-3-methyl-2-((S)-4-methyl-2-phenylsulfonylaminovalerylamino)butyl]-3-phenylcyclopropenone (compd. No. 239 in Table 1)

mp: 207° C.(dec.) IR(KBr, cm$^{-1}$): 3450, 3300, 1858, 1665, 1625 NMR(CD$_3$OD, δ): 0.38(d, J=6.6 Hz, 3H), 0.40(d, J=6.5 Hz, 3H), 0.78(d, J=6.7 Hz, 3H), 1.02(d, J=6.6 Hz, 3H), 0.75-0.95(m, 2H), 1.34(m, 1H), 1.97(m, 1H), 3.71(dd, J=10 Hz, 4.4 Hz, 1H), 3.92(dd, J=9.4 Hz, 2.5 Hz, 1H), 5.14(d, J=2.5 Hz, 1H), 7.42-7.70(m, 6H), 7.81(dd, J=8.4 Hz, 1.6 Hz, 2H), 8.03(dd, J=7.6 Hz, 1.2 Hz, 2H)

EXAMPLE 81

Preparation of 2-[(1R, 2S)-1-hydroxy-3-methyl-2-((S)-4-methyl-2-phenylsulfonylaminovalerylamino)butyl]-3-phenylcyclopropenone (compd. No. 239 in Table 1)

mp: 193°-194° C.(dec.) IR(KBr, cm$^{-1}$): 3300, 1860, 1664, 1627 NMR(CDCl$_3$, δ): 0.45(d, J=5.9 Hz, 3H), 0.69(d, J=6.0 Hz, 3H), 0.99(d, J=6.6 Hz, 3H), 1.11(d, J=6.6 Hz, 3H), 1.30-1.55(m, 3H), 2.10(m, 1H), 3.64(m, 1H), 4.06(m, 1H), 4.81(d, J=8.0 Hz, 1H), 5.11(dd, J=7.9 Hz, 3.2 Hz, 1H), 6.04(d, J=7.7 Hz, 1H), 7.17(d, J=8.8 Hz, 1H), 7.40-7.65(m, 6H), 7.83(d, J=7.2 Hz, 2H), 7.97(d, J=7.0 Hz, 2H)

EXAMPLE 82

Preparation of 2-[(1S, 2S)-1-acetoxy-3-methyl-2-((S)-4-methyl-2-phenylsulfonylaminovalerylamino)butyl]-3-phenylcyclopropenone (compd. No. 241 in Table 1)

mp: 202°-204° C.(dec.) IR(KBr, cm$^{-1}$): 3274, 1863, 1751, 1678, 1630 NMR(CDCl$_3$, δ): 0.58(d, J=6.2 Hz, 3H), 0.68(d, J=6.4 Hz, 3H), 0.88(d, J=6.8 Hz, 3H), 0.92(d, J=6.8 Hz, 3H), 1.30-1.60(m, 3H), 1.92(m, 1H), 2.26(s, 3H), 3.67(m, 1H), 4.32(m, 1H), 5.48(d, J=7.5 Hz, 1H), 5.99(d, J=5.0 Hz, 1H), 6.42(d, J=9.9 Hz, 1H), 7.45-7.65(m, 6H), 7.75-7.90(m, 4H)

EXAMPLE 83

Preparation of 2-[(1S, 2S)-2-{(S)-2-(4-fluorophenylsulfonylamino)-4-methylvalerylamino}-1-hydroxy-3-methylbutyl]-3-phenylcyclopropenone (compd. No. 245 in Table 1)

mp: 207°-208° C.(dec.) IR(KBr, cm$^{-1}$): 3561, 3272, 1858, 1667, 1634 NMR(CD$_3$OD, δ): 0.39(d, J=6.7 Hz, 3H), 0.46(d, J=6.5 Hz, 3H), 0.74(d, J=6.7 Hz, 3H), 0.86(m, 1H), 1.02(d, J=6.7 Hz, 3H), 1.03(m, 1H), 1.39(m, 1H), 1.96(m, 1H), 3.72(dd, J=11 Hz, 4.2 Hz, 1H), 3.90(m, 1H), 5.14(d, J=2.4 Hz, 1H), 7.15-7.28(m, 2H), 7.50-7.65(m, 3H), 7.78-7.90(m, 2H), 7.98-8.18(m, 2H), 8.09(d, J=9.6 Hz, 1H)

EXAMPLE 84

Preparation of 2-[(1S, 2S)-2-{(S)-2-(2-chlorophenylsulfonylamino)-4-methylvalerylamino}-1-hydroxy-3-methylbutyl]-3-phenylcyclopropenone (compd. No. 246 in Table 1)

mp: 106°-109° C.(dec.) IR(KBr, cm$^{-1}$): 3327, 1856, 1624 NMR(CDCl$_3$, δ): 0.23(d, J=6.4 Hz, 3H), 0.53(d, J=6.5 Hz, 3H), 1.10(d, J=6.3 Hz, 3H), 1.12(d, J=6.3 Hz, 3H), 1.27(m, 2H), 1.41(m, 1H), 2.38(m, 1H), 3.50(m, 1H), 3.93(m, 1H), 5.21(d, J=4.3 Hz, 1H), 7.01(d, J=6.2

Hz, 1H), 7.31–7.42(m, 2H), 7.42–7.60(m, 5H), 8.01(dd, J=6.8 Hz, 1.4 Hz, 2H), 8.03(d, J=7.3 Hz, 1H)

EXAMPLE 85

Preparation of 2-[(1S, 2S)-2-{(S)-2-(4-chlorophenylsulfonylamino)-4-methylvalerylamino}-1-hydroxy-3-methylbutyl]-3-phenylcyclopropenone (compd. No. 248 in Table 1)

mp: 206° C.(dec.) IR(KBr, cm⁻¹): 3559, 3268, 1664, 1634 NMR(CD₃OD, δ): 0.39(d, J=6.7 Hz, 3H), 0.48(d, J=6.5 Hz, 3H), 0.71(d, J=6.7 Hz, 3H), 0.82(m, 1H), 1.01(d, J=6.6 Hz, 3H), 1.05(m, 1H), 1.41(m, 1H), 1.93(m, 1H), 3.74(dd, J=11 Hz, 4.1 Hz, 1H), 3.89(m, 1H), 5.13(d, J=2.4 Hz, 1H), 7.50–7.68(m, 5H), 7.75–7.83(m, 2H), 7.98–8.14(m, 3H)

EXAMPLE 86

Preparation of 2-[(1S, 2S)-1-hydroxy-3-methyl-2-{(S)-4-methyl-2-(4-trisulfonylamino)valerylamino}butyl]-3-phenylcyclopropenone (compd. No. 251 in Table 1)

mp: 203°–205° C.(dec.) IR(KBr, cm⁻¹): 3318, 1856, 1680, 1626 NMR(CDCl₃, δ): 0.19(d, J=6.4 Hz, 3H), 0.49(d, J=6.4 Hz, 3H), 1.07(d, J=6.6 Hz, 3H), 1.12(d, J=6.6 Hz, 3H), 0.90–1.40(m, 3H), 2.25(m, 1H), 2.38(s, 3H), 3.49(m, 1H), 4.01(m, 1H), 5.23(dd, J=7.8 Hz, 3.8 Hz, 1H), 5.82(d, J=8.0 Hz, 1H), 7.13–7.35(m, 3H), 7.44–7.60(m, 4H), 7.73(d, J=8.2 Hz, 2H), 8.0(d, J=6.4 Hz, 2H)

EXAMPLE 87

Preparation of 2-[(1S, 2S)-1-hydroxy-2-{(S)-2-(4-methoxyphenylsulfonylamino)-4-methylvalerylamino}-3-methylbutyl]-3-phenylcyclopropenone (compd. No. 257 in Table 1)

mp: 201°–202° C.(dec.) IR(KBr, cm⁻¹): 3335, 1856, 1680, 1626 NMR(CDCl₃, δ): 0.23(d, J=6.4 Hz, 3H), 0.51(d, J=6.5 Hz, 3H), 1.08(d, J=6.8 Hz, 3H), 1.12(d, J=6.7 Hz, 3H), 0.93–1.37(m, 3H), 2.30(m, 1H), 3.48(m, 1H), 3.83(s, 3H), 3.99(m, 1H), 5.22(dd, J=8.1 Hz, 3.8 Hz, 1H), 5.81(d, J=7.6 Hz, 1H), 6.91(d, J=9.0 Hz, 2H), 7.03(d, J=6.3 Hz, 1H), 7.42–7.61(m, 4H), 7.78(d, J=9.0 Hz, 2H), 7.95–8.08(m, 2H)

EXAMPLE 88

Preparation 2-[(1S, 2S)-1-hydroxy-3-methyl-2-{(S)-4-methyl-2-(1-naphtylsulfonylamino)valerylamino}butyl]-3-phenylcyclopropenone (compd. No. 259 in Table 1)

mp: 109°–115° C. IR(KBr, cm⁻¹): 3360, 1856, 1640, 1603 NMR(DMSO-d6, δ): −0.01(d, J=4.4 Hz, 3H), 0.12(d, J=6.3 Hz, 3H), 0.61(d, J=6.1 Hz, 3H), 0.89(d, J=6.6 Hz, 3H), 0.80–1.22(m, 3H), 1.79(m, 1H), 3.58–3.78(m, 2H), 5.02(m, 1H), 6.24(d, J=4.7 Hz, 1H), 7.45–7.65(m, 6H), 7.85–7.99(m, 3H), 7.99–8.07(m, 1H), 8.07–8.12(m, 3H), 8.59(d, J=9.1 Hz, 1H)

EXAMPLE 89

Preparation of 2-[(1S, 2S)-1-hydroxy-3-methyl-2-{(S)-4-methyl-2-(2-naphtylsulfonylamino)valerylamino}butyl]-3-phenylcyclopropenone (compd. No. 260 in Table 1)

mp: 214° C.(dec.) IR(KBr, cm⁻¹): 3551, 3474, 3264, 1856, 1669, 1634 NMR(DMSO-d6 δ): 0.23–0.45(m, 9H), 0.75(d, J=6.2 Hz, 3H), 0.65–0.85(m, 1H), 0.85–1.05(m, 1H), 1.34(m, 1H), 1.67(m, 1H), 3.64(m, 1H), 3.81(m, 1H), 4.99(m, 1H), 6.24(m, 1H), 7.46–8.10(m, 13H), 8.33(m, 1H)

EXAMPLE 90

Preparation of 2-[(1S, 2S)-1-hydroxy-3-methyl-2-{(S)-4-methyl-2-(3-pyridylsulfonylamino)valerylamino}butyl]-3-phenylcyclopropenone (compd. No. 262 in Table 1)

mp: 110°–112° C. IR(KBr, cm⁻¹): 3285, 1856, 1672, 1624 NMR(CDCl₃, δ): 0.13(d, J=6.4 Hz, 3H), 0.42(d, J=6.4 Hz, 3H), 0.87(m, 1H), 1.11(d, J=6.4 Hz, 3H), 1.13(d, J=6.5 Hz, 3H), 1.24(m, 2H), 2.24(m, 1H), 3.53(m, 1H), 4.15(m, 1H), 5.29(d, J=2.8 Hz, 1H), 5.76(s, 1H), 7.38–7.55(m, 4H), 7.68(s, 1H), 8.01(dd, J=7.6 Hz, 1.4 Hz, 2H), 8.17(ddd, J=8.1 Hz, 1.7 Hz, 1.7 Hz, 1H), 8.48(d, J=7.0 Hz, 1H), 8.74(dd, J=4.8 Hz, 1.5 Hz, 1H), 9.10(d, J=2.0 Hz, 1H)

EXAMPLE 91

Preparation of 2-[(1S, 2S)-1-hydroxy-3-methyl-2-{(S)-4-methyl-2-(8-quinolylsulfonylamino)valerylamino}butyl]-3-phenylcyclopropenone (compd. No. 265 in Table 1)

mp: 132°–137° C.(dec.) IR(KBr, cm⁻¹): 3287, 1856, 1665, 1626 NMR(CDCl₃, δ): −0.03(d, J=6.3 Hz, 3H), 0.41(d, J=6.4 Hz, 3H), 0.90–1.30(m, 3H), 1.07(d, J=6.6 Hz, 3H), 0.83(d, J=6.7 Hz, 3H), 2.42(m, 1H), 3.52(m, 1H), 3.79(m, 1H), 5.09(dd, J=7.8 Hz, 5.8 Hz, 1H), 5.70(d, J=7.8 Hz, 1H), 6.65(d, J=2.9 Hz, 1H), 7.35(d, J=8.4 Hz, 1H), 7.40–7.70(m, 5H), 8.02(dd, J=7.4 Hz, 2.0 Hz, 2H), 8.09(dd, J=8.3 Hz, 1.3 Hz, 1H), 8.27–8.39(m, 2H), 9.05(dd, J=4.3 Hz, 1.6 Hz, 1H)

EXAMPLE 92

Preparation of 2-[(1S, 2S)-2-((S)-2-benzyloxycarbonylamino-3-phenylpropionylamino)-1-hydroxy-3-methylbutyl]-3-phenylcyclopropenone (compd. No. 276 in Table 1)

mp: 175°–177° C. IR(KBr, cm⁻¹): 3300, 1850, 1697, 1648, 1620 NMR(CDCl₃, δ): 0.85(d, J=6.7 Hz, 3H), 0.95(d, J=6.6 Hz, 3H), 2.28(m, 1H), 2.80(dd, J=14 Hz, 7.9 Hz, 1H), 2.99(dd, J=14 Hz, 5.9 Hz, 1H), 3.60(m, 1H), 4.42(m, 1H), 4.85–5.05(m, 3H), 5.42(d, J=6.2 Hz, 1H), 5.99(d, J=8.0 Hz, 1H), 7.05–7.35(m, 10H), 7.35–7.60(m, 4H), 7.92–8.03(m, 2H)

EXAMPLE 93

Preparation of 2-[(2S)-2-((S)-2-benzyloxycarbonylamino-3-phenylpropionylamino)-1-hydroxy-3-methylbutyl]-3-phenylcyclopropenone (compd. No. 276 in Table 1)

IR(KBr, cm⁻¹): 3300, 1855, 1693, 1645, 1620 NMR(CDCl₃, δ): 0.84(d, J=6.2 Hz, 1.8H), 0.95(d, J=6.7 Hz, 1.2H), 1.02( d, J=6.4 Hz, 1.8H), 1.05(d, H=6.0 Hz, 1.2H), 2.03(m, 0.4H), 2.27(m, 0.6H), 2.75–2.88(m, 0.6H), 2.90–3.05(m, 1.4H), 3.58(m, 0.6H), 4.05(m, 0.4H), 4.41(q, J=6.8 Hz, 1H), 4.73(m, 0.4H), 4.85–5.05(m, 3.6H), 5.27–5.45(m, 1H), 5.94(d, J=7.9 Hz, 0.6H), 7.70(d, J=7.6 Hz, 0.4H), 7.50–7.37(m, 10H), 7.44–7.62(m, 3H), 7.95–8.05(m, 2H)

EXAMPLE 94

Preparation of
2-[(2S)-2-((S)-2-cyclohexylmethoxycarbonylamino-4-methylvalerylamino)-1-hydroxyhexyl]-3-phenylcyclopropenone (compd. No. 280 in Table 1)

IR(KBr, cm$^{-1}$): 3310, 1855, 1790, 1755, 1725 NMR(CDCl$_3$, δ): 0.65–0.75(m, 1.2H), 0.75–1.05(m, 7.8H), 1.10–2.0(m, 20H), 2.07(s, 1H), 3.65–3.90(m, 2H), 4.0–4.20(m, 1.7H), 4.20–4.35(m, 0.3H), 4.95–5.05(m, 1H), 5.10–5.30(m, 0.3H), 5.45–5.60(m, 0.7H), 5.60–5.85(m, 1H), 7.0–7.25(m, 0.7H), 7.45–7.56(m, 3.3H), 7.95–8.05(m, 2H)

EXAMPLE 95

Preparation of
2-[(2S)-2-((S)-2-benzyloxycarbonylamino-4-methylvalerylamino)-1-hydroxyhexyl]-3-phenylcyclopropenone (compd. No. 281 in Table 1)

IR(KBr, cm$^{-1}$): 3320, 1855, 1700, 1655, 1625 NMR(CDCl$_3$,δ): 0.60–0.70(m, 1.8H), 0.70–1.0(m, 7.2H), 1.20–1.65(m, 8H), 1.75–1.95(m, 1H), 2.0(s, 1H), 4.0–4.30(m, 2H), 4.90–5.10(m, 2.7H), 5.35(d, J=7 Hz, 0.3H), 5.70–5.85(m, 1H), 7.05–7.10(m, 0.7H), 7.30(s, 5H), 7.45–7.56(m, 3.3H), 7.95–8.10(m, 2H)

EXAMPLE 96

Preparation of 2-[(2S)-1-hydroxy-2-{(S)-4-methyl-2-(2-pyridylmethoxycarbonylamino)valerylamino]hexyl]-3-phenylcyclopropenone (compd. No. 282 in Table 1)

IR(KBr, cm$^{-1}$): 3320, 1855, 1715, 1655, 1628 NMR(CDCl$_3$, δ): 0.65–0.75(m, 1.8H), 0.75–0.95(m, 7.2H), 1.10–1.70(m, 8H), 1.70–2.0(m, 1H), 2.28(s, 1H), 4.05–4.35(m, 2H), 5.03(s, 1H), 5.16(s, 2H), 6.13(d, J=8 Hz, 1H), 7.13–7.25(m, 1H), 7.31(d, J=7 Hz, 1H), 7.35–7.60(m, 4H), 7.66(t, J=7 Hz, 1H), 7.95–8.05(m, 2H), 8.51(d, J=5 Hz, 1H)

EXAMPLE 97

Preparation of
2-[(RS)-2-((S)-2-tert-butoxycarbonylamino-4-methylvalerylamino)-1-hydroxy-2-methylpropyl]-3-phenylcyclopropenone (compd. No. 290 in Table 1)

IR(KBr, cm$^{-1}$): 3320, 1858, 1690, 1650, 1625 NMR(CDCl$_3$, δ): 0.60–0.95(m, 6H), 1.10–1.70(m, 18H), 3.92(m, 1H), 4.65–4.92(m, 2H), 6.63(d, J=13 Hz, 1H), 6.70–6.95(m, 1H), 7.20–7.45(m, 3H), 8.01(d, J=6.5 Hz, 2H)

EXAMPLE 98

Preparation of
2-[(RS)-2-((S)-2-cyclohexylmethoxycarbonylamino-4-methylvalerylamino)-1-hydroxy-2-methylpropyl]-3-phenylcyclopropenone (compd. No. 289 in Table 1)

IR(KBr, cm$^{31}$ $^1$): 3300, 1857, 1695, 1648, 1623 NMR(CDCl$_3$, δ): 0.65–1.05(m, 8H), 1.05–1.90(m, 18H), 3.68–3.95(m, 2H), 4.0(m, 1H), 4.70–4.88(m, 1H), 4.99(m, 1H), 6.50–6.93(m, 2H), 7.40–7.60(m, 3H), 8.01(dd, J=5.8 Hz, 1.8 Hz, 2H)

EXAMPLE 99

Preparation of
2-[(RS)-2-((S)-2-amino-4-methylvalerylamino)-1-hydroxy-2-methylpropyl]-3-phenylcyclopropenone hydrochloride (compd. No. 294 in Table 1)

IR(KBr, cm$^{-1}$): 3250, 1857 1678, 1615 NMR(CD$_3$OD, δ): 0.90–1.10(m, 6H), 1.29(s, 1.5H), 1.46(s, 1.5H), 1.51(s, 1.5H), 1.57(s, 1.5H), 1.55–1.85(m, 3H), 3.89(m, 1H), 5.42(s, 0.5H), 5.76(s, 0.5H), 7.55–7.75(m, 3H), 8.0–8.10(m, 2H)

EXAMPLE 100

Preparation of
2-[(RS)-1-hydroxy-2-methyl-2-((S)-4-methyl-2-phenylsulfonylaminovalerylamino)propyl]-3-phenylcyclopropenone (compd. No. 297 in Table 1)

IR(KBr, cm$^{-1}$): 3350, 3290, 3180, 1858, 1654, 1623, 1615 NMR(CDCl$_3$, δ): 0.41(d, J=6.4 Hz, 1.5H), 0.52(d, J=6.5 Hz, 1.5H), 0.56(d, J=6.6 Hz, 1.5H), 0.66(d, J=6.5 Hz, 1.5H), 1.08–1.38(m, 3H), 1.34(s, 1.5H), 1.39(s, 1.5H), 1.49(s, 1.5H), 1.51(s, 1.5H), 3.65(m, 1H), 4.67(d, J=10 Hz, 0.5H), 4.90(d, J=8.4 Hz, 0.5H), 5.73(d, J=8.2 Hz, 0.5H), 6.27(d, J=8.4 Hz, 0.5H), 6.53(d, J=7.6 Hz, 0.5H), 6.90(s, 0.5H), 6.98(d, J=10 Hz, 0.5H), 7.26(s, 0.5H), 7.45–7.65(m, 6H), 7.84(t, J=6.7 Hz, 2H), 8.00(d, J=7.1 Hz, 2H)

EXAMPLE 101

Preparation of
2-[(RS)-1-hydroxy-2-methyl-2-{(S)-4-methyl-2-(N-(methylthiomethyl)phenylsulfonylamino)valerylamino}propyl]-3-phenylcyclopropenone (compd. No. 298 in Table 1)

IR(KBr, cm$^{-1}$): 3350, 3280, 1856, 1670, 1624 NMR(CDCl$_3$, δ): 0.33(d, J=6.3 Hz, 1.5H), 0.38(d, J=6.3 Hz, 1.5H), 0.48(d, J=6.4 Hz, 1.5H), 0.54(d, J=6.5 Hz, 1.5H), 0.65–1.15(m, 3H), 1.51(s, 1.5H), 1.59(s, 1.5H), 1.62(s, 1.5H), 1.71(s, 1.5H), 2.27(s, 1.5H), 2.28(s, 1.5H), 3.92(m, 0.5H), 3.95(m, 0.5H), 4.23(d, J=15 Hz, 0.5H), 4.33(d, J=15 Hz, 0.5H), 4.61(d, J=15 Hz, 0.5H), 4.70(d, J=15 Hz, 0.5H), 4.82(d, J=9.4 Hz, 0.5H), 5.05(d, J=7.8 Hz, 0.5H), 6.28(d, J=7.9 Hz, 0.5H), 6.70(d, J=9.5 Hz, 0.5H), 6.73(s, 0.5H), 7.18(s, 0.5H), 7.45–7.70(m, 6H), 7.80–7.92(m, 2H), 7.99–8.12(m, 2H)

EXAMPLE 102

Preparation of
2-[2-((S)-2-cyclohexylmethoxycarbonylamino-4-methylvalerylamino)-2-methylpropionyl]-3-phenylcyclopropenone (compd. No. 299 in Table 1)

mp: 42°–49° C. IR(KBr, cm$^{-1}$): 3350, 1768, 1720, 1680 NMR(CDCl$_3$, δ): 0.85–1.35(m, 14H), 1.50(s, 3H), 1.50–1.87(m, 9H), 3.91(m, 2H), 4.52(m, 1H), 4.58–4.63(m, 1H), 5.09(m, 1H), 7.30–7.55(m, 3H), 7.93–8.06(m, 2H)

EXAMPLE 103

Preparation of
2-[2-methyl-2-((S)-4-methyl-2-phenylsulfonylaminovalerylamino)propionyl]-3-phenylcyclopropenone (compd. No. 301 in Table 1)

mp: 53°–59° C. IR(KBr, cm$^{-1}$): 3430, 3260 1765 1678 NMR(CDCl$_3$, δ): 0.60(s, 2H), 0.79(s, 1H), 0.95(d, J=6.4 Hz, 3H), 0.97(d, J=5.1 Hz, 3H), 1.23(s, 1H), 1.35(s, 2H), 1.60(m, 2H), 1.85(m, 1H), 3.86(s, 0.3H), 4.11(m, 1H), 4.15(s, 0.7H), 5.24(m, 1H), 7.33–7.62(m, 7H), 7.80–7.95(m, 4H)

EXAMPLE 104

Preparation of 2-[(1S, 2S)-2-((S)-2-cyclohexylmethoxycarbonylamino-4-methylvalerylamino)-1-hydroxy-3-methylbutyl]-3-(4-fluorophenyl)cyclopropenone (compd. No. 311 in Table 1)

mp: 86°–90° C. IR(KBr, cm⁻¹): 3320, 1858, 1693, 1656, 1625, 1602 NMR(CDCl₃, δ): 0.79(d, J=5.9 Hz, 6H), 1.01(d, J=6.6 Hz, 3H), 1.09(d, J=6.6 Hz, 3H), 0.70–1.45(m, 7H), 1.45–1.83(m, 7H), 2.39(m, 1H), 3.50–3.85(m, 3H), 4.08(m, 1H), 5.10(dd, J=8.6 Hz, 4.7 Hz, 1H), 5.25(m, 1H), 6.23(m, 1H), 7.19(dd, J=8.5 Hz, 8.5 Hz, 2H), 7.47(m, 1H), 8.01(dd, J=8.5 Hz, 5.5 Hz, 2H)

EXAMPLE 105

Preparation of 2-[(1S, 2S)-2-((S)-2-cyclohexylmethoxycarbonylamino-4-methylvalerylamino)-1-hydroxy-3-methylbutyl]-3-(4-fluorophenyl)cyclopropenone (compd. No. 311 in Table 1)

mp: 166°–168° C. IR(KBr, cm⁻¹): 3340, 3260, 1861, 1714, 1655, 1625 NMR(CDCl₃, δ): 0.63–1.03(m, 8H), 1.07(d, J=6.6 Hz, 3H), 1.14(d, J=6.6 Hz, 3H), 1.03–1.80(m, 12H), 2.14(m, 1H), 3.55–3.85(m, 2H), 3.95–4.15(m, 2H), 5.0–5.23(m, 2H), 5.29(d, J=5.7 Hz, 1H), 6.90(d, J=7.0 Hz, 1H), 7.18(dd, J=8.5 Hz, 8.5 Hz, 2H), 8.04(dd, J=8.5 Hz, 5.8 Hz, 2H)

EXAMPLE 106

Preparation of 2-[(1S, 2S)-2-((S)-2-tert-butoxycarbonylamino-4-methylvalerylamino)-1-hydroxy-3-methylbutyl]-3-(4-fluorophenyl)cyclopropenone (compd. No. 312 in Table 1)

mp: 90°–96° C. IR(KBr, cm⁻¹): 3340, 1858, 1687, 1655, 1635, 1600 NMR(CDCl₃, δ): 0.77(d, J=6.3 Hz, 6H), 1.02(d, J=6.6 Hz, 3H), 1.09(d, J=6.4 Hz, 3H), 1.20–1.65(m, 3H), 1.39(s, 9H), 2.40(m, 1H), 3.68(m, 1H), 4.07(m, 1H), 5.03–5.31(m, 2H), 6.23(m, 1H), 7.10–7.25(m, 3H), 7.95–8.13(m, 2H)

EXAMPLE 107

Preparation of 2-[(1R, 2S)-2-((S)-2-tert-butoxycarbonylamino-4-methylvalerylamino)-1-hydroxy-3-methylbutyl]-3-(4-fluorophenyl)cyclopropenone (compd. No. 312 in Table 1)

IR(KBr, cm⁻¹): 3320, 1859, 1686, 1627 NMR(CDCl₃, δ): 0.71(d, J=5.7 Hz, 6H), 1.08(d, J=6.6 Hz, 3H), 1.14(d, J=6.7 Hz, 3H), 1.20–1.70(m, 3H), 1.37(s, 9H), 2.14(m, 1H), 3.98–4.15(m, 2H), 4.98(m, 1H), 5.13(m, 1H), 5.39(d, J=5.8 Hz, 1H), 6.88(d, J=6.9 Hz, 1H), 7.17(dd, J=8.6 Hz, 8.6 Hz, 2H), 8.03(dd, J=8.6 Hz, 5.5 Hz, 2H)

EXAMPLE 108

Preparation of 2-[(1S, 2S)-2-((S)-2-amino-4-methylvalerylamino)-1-hydroxy-3-methylbutyl]-3-(4-fluorophenyl)cyclopropenone hydrochloride (compd. No. 314 in Table 1)

mp: 141°–145° C.(dec.) IR(KBr, m⁻¹): 3250, 1857, 1683, 1620, 1600 NMR(CD₃OD, δ): 0.52(d, J=6.5 Hz, 3H), 0.74(d, J=6.5 Hz, 3H), 1.02(d, J=6.8 Hz, 3H), 1.13(d, J=6.6 Hz, 3H), 1.0–1.35(m, 2H), 1.43(m, 1H), 2.11(m, 1H), 3.81(m, 1H), 4.11(m, 1H), 5.23(d, J=2.1 Hz, 1H), 7.18–7.42(m, 2H), 8.10–8.25(m, 2H)

EXAMPLE 109

Preparation of 2-[(1R, 2S)-2-((S)-2-amino-4-methylvalerylamino)-1-hydroxy-3-methylbutyl]-3-(4-fluorophenyl)cyclopropenone hydrochloride (compd. No. 314 in Table 1)

IR(KBr, cm⁻¹): 3300, 3250, 1860, 1683, 1620, 1603 NMR(CD₃OD, δ): 0.84(d, J=5.9 Hz, 3H), 0.88(d, J=5.9 Hz, 3H), 1.04(d, J=6.8 Hz, 3H), 1.10(d, J=6.8 Hz, 3H), 1.58–1.78(m, 3H), 2.16(m, 1H), 3.84(m, 1H), 4.02(m, 1H), 5.17(d, J=6.7 Hz, 1H), 7.22–7.35(m, 2H), 8.05–8.16(m, 2H)

EXAMPLE 110

Preparation of 2-(4-fluorophenyl)-3-[(1R, 2S)-1-hydroxy-3-methyl-2-{(S)-4-methyl-2-(phenoxyacetylamino)valerylamino} butyl]cyclopropenone (compd. No. 315 in Table 1)

mp: 75°–79° C. IR(KBr, cm⁻¹): 3410, 3290, 1853, 1650, 1620 NMR(CDCl₃, δ): 0.66(d, J=6.2 Hz, 6H), 1.05(d, J=6.6 Hz, 3H), 1.14(d, J=6.7 Hz, 3H), 1.36(m, 2H), 1.56(m, 1H), 2.14(m, 1H), 4.02(m, 1H), 4.41(d, J=15 Hz, 1H), 4.48(d, J=15 Hz, 1H), 4.51(m, 1H), 5.13(dd, J=6.4 Hz, 2.5 Hz, 1H), 5.29(d, J=6.4 Hz, 1H), 6.91(d, J=7.9 Hz, 2H), 7.03(t, J=7.4 Hz, 1H), 7.12–7.28(m, 3H), 7.31(dd, J=8.5 Hz, 7.5 Hz, 2H), 8.04(dd, J=8.7 Hz, 5.5 Hz, 2H)

EXAMPLE 111

Preparation of 2-(4-fluorophenyl)-3-[(1S, 2S)-1-hydroxy-3-methyl-2-((S)-4-methyl-2-phenylsulfonylaminovalerylamino)butyl]cyclopropenone (compd. No. 317 in Table 1)

mp: 211°–212° C.(dec.) IR(KBr, cm⁻¹): 3400, 3300, 1853, 1670, 1619 NMR(CDCl₃, δ): 0.16(d, J=6.4 Hz, 3H), 0.48(d, J=6.4 Hz, 3H), 0.93(m, 1H), 1.10(d, J=6.7 Hz, 3H), 1.13(d, J=6.7 Hz, 3H), 1.15–1.35(m, 2H), 2.29(m, 1H), 3.47(m, 1H), 4.10(m, 1H), 5.26(dd, J=7.9 Hz, 5.3 Hz, 1H), 5.76(d, J=7.3 Hz, 1H), 7.17(dd, J=8.6 Hz, 2H), 7.38–7.57(m, 4H), 7.54(d, J=7.4 Hz, 1H), 7.86(d, J=6.7 Hz, 2H), 8.04(dd, J=8.6 Hz, 5.5 Hz, 2H)

EXAMPLE 112

Preparation of 2-[(2S)-2-((S)-2-benzyloxycarbonylamino-4-methylvalerylamino)-1-hydroxyhexyl]-3-(4-fluorophenyl)cyclopropenone (compd. No. 319 in Table 1)

IR(KBr, cm⁻¹): 3310, 1857, 1698, 1652, 1625, 1600 NMR(CDCl₃, δ): 0.75–0.98(m, 9H), 1.15–1.95(m, 9H), 3.95–4.30(m, 2H), 4.88–5.12(m, 3H), 5.39(d, J=7.8 Hz, 0.3H), 5.70–5.90(m, 1.7H), 7.08–7.35(m, 3H), 7.30(s, 5H), 7.90–8.10(m, 2H)

EXAMPLE 113

Preparation of 2-[(2S)-2-((S)-2-cyclohexylmethoxycarbonylamino-4-methylvalerylamino)-1-hydroxyhexyl]-3-(2-tolyl)cyclopropenone (compd. No. 328 in Table 1)

IR(KBr, cm⁻¹): 3320, 1845, 1692, 1655, 1615 NMR(CDCl₃, δ): 0.60–1.05(m, 11H), 1.05–2.0(m, 18H), 2.66(s, 2.1H), 2.68(s, 0.9H), 3.65–3.95(m, 2H), 3.95–4.35(m, 2H), 4.95–5.12(m, 1H), 5.24(m, 0.3H), 5.55(m, 0.7H), 7.05–7.35(m, 6H), 7.35–7.50(m, 3H), 8.05–8.20(m, 2H)

EXAMPLE 114

Preparation of 2-[(2S)-2-((S)-2-cyclohexylmethoxycarbonylamino-4-methylvalerylamino)-1-hydroxy-1-hexyl]-3-(5-trimethylsilyl-2-furil)cyclopropenone (compd. No. 376 in Table 1)

IR(KBr, cm$^{-1}$): 3310, 1865, 1695, 1655, 1623 NMR(CDCl$_3$, δ): 0.35(s, 9H), 0.70–1.05(m, 11H), 1.05–2.0(m, 18H), 3.70–3.95(m, 2H), 3.95–4.35(m, 2H), 4.92(m, 1H), 5.0–5.50(m, 1H), 6.45–6.85(m, 1H)n6.76(d, J=3.4 Hz, 1H), 7.20–7.28(m, 1H)

EXAMPLE 115

Preparation of 2-[(2S)-2-((S)-2-cyclohexylmethoxycarbonylamino-4-methylvalerylamino)-1-hydroxy-1-hexyl]-3-(5-trimethylsilyl-2-thienyl)cyclopropenone (compd. No. 387 in Table 1)

IR(KBr, cm$^{-1}$): 3320, 1853, 1695, 1655, 1615 NMR(CDCl$_3$, δ): 0.35(s, 9H), 0.70–1.05(m, 11H), 1.10–2.0(m, 18H), 3.73–3.90(m, 2H), 3.90–4.15(m, 2H), 4.92(d, J=4.8 Hz, 1H), 4.95–5.10(m, 0.3H), 5.10–5.30(m, 0.7H), 6.50–6.65(m, 0.3H), 6.80–6.95(m, 0.7H), 7.29(d, J=3.6 Hz, 1H), 7.82(d, J=3.6 Hz, 0.7H), 7.84(d, J=3.6 Hz, 0.3H)

EXAMPLE 116

Preparation of 2-[(2S)-2-((S)-2-benzyloxycarbonylamino-4-methylvalerylamino)-3-methylbutyl]-3-(1-hydroxy-1-methylethyl)cyclopropenone (compd. No. 422 in Table 1)

IR(KBr, cm$^{-1}$): 3316, 1840, 1696, 1655 NMR(CD$_3$OD, δ): 0.80–1.0(m, 9.9H)n1.03(d, J=6.6 Hz, 2.1H), 1.49(s, 2.1H), 1.52(s, 1.8H), 1.53(s, 2.1H), 1.40–1.80(m, 3H), 1.86–2.20(m, 1H), 4.02(m, 1H), 4.18(m, 1H), 5.03(d, J=2.2 Hz, 1H), 5.08(s, 2H), 7.18–7.41(m, 5H), 7.82(d, J=8.3 Hz, 0.3H), 7.98(d, J=8.7 Hz, 0.7H)

EXAMPLE 117

Preparation of 2-[(2S)-2-((S)-2-benzyloxycarbonylamino-4-methylvalerylamino)-1-hydroxy-3-methylbutyl]-3-(1-hydroxy-1-phenylmethyl)cyclopropenone (compd. No. 444 in Table 1)

IR(KBr, cm$^{-1}$): 3399, 1846, 1696, 1647 NMR(CD$_3$OD, δ): 0.85–1.10(m, 12H), 1.30–1.75(m, 3H), 1.85–2.10(m, 1H), 3.85–4.23(m, 2H), 4.94(m, 0.3H), 5.03(m, 0.7H), 5.08(s, 2H), 5.75–5.90(m, 1H), 7.13–7.55(m, 10H)

EXAMPLE 118

Preparation of 2-[(1S, 2S)-2-{(S)-2-((S)-2-cyclohexylmethoxycarbonylamino-4-methylvalerylamino)-4-methylvalerylamino}-1-hydroxy-3-methylbutyl]-3-phenylcyclopropenone (compd. No. 467 in Table 2)

mp: 190°–192° C. IR(KBr, cm$^{-1}$): 3310, 1848, 1687, 1638, 1625 NMR(CDCl$_3$, δ): 0.77(d, J=4.9 Hz, 6H), 0.91(d, J=5.4 Hz, 3H), 0.94(d, J=6.1 Hz, 3H), 1.01(d, J=6.5 Hz, 3H), 1.08(d, J=6.5 Hz, 3H), 0.80–1.85(m, 17H), 2.37(m, 1H), 3.62(m, 1H), 3.75–4.0(m, 3H), 4.08(m, 1H), 4.42(m, 1H), 5.10(s, 1H), 5.28(m, 1H), 6.12(m, 1H), 6.88(d, J=7.5 Hz, 1H), 7.45–7.85(m, 4H), 7.98(d, J=7.1 Hz, 2H)

EXAMPLE 119

Preparation of 2-[(1R, 2S)-2-{(S)-2-((S)-2-cyclohexylmethoxycarbonylamino-4-methylvalerylamino)-4-methylvalerylamino}-1-hydroxy-3-methylbutyl]-3-phenylcyclopropenone (compd. No. 467 in Table 2)

mp: 109°–116° C. IR(KBr, cm$^{-1}$): 3300, 1858, 1699, 1645 NMR(CDCl$_3$, δ): 0.52(d, J=5.6 Hz, 3H), 0.59(d, J=5.6 Hz, 3H), 0.85(d, J=6.4 Hz, 3H), 0.89(d, J=6.4 Hz, 3H), 0.80–1.0(m, 2H), 1.01(d, J=6.4 Hz, 3H), 1.13(d, J=6.5 Hz, 3H), 1.05–1.40(m, 4H), 1.40–1.85(m, 11H), 2.20(m, 1H), 3.70–3.93(m, 2H), 3.98–4.10(m, 2H), 4.52(m, 1H), 5.15(m, 1H), 5.39(s, 1H), 5.85(d, J=6.5 Hz, 1H), 7.01(d, J=6.8 Hz, 1H), 7.35–7.65(m, 4H), 8.01(d, J=6.9 Hz, 2H)

EXAMPLE 120

Preparation of 2-[(1S, 2S)-2-{(S)-2-((S)-2-benzyloxycarbonylamino-3-phenylpropionylamino)-4-methylvalerylamino}-1-hydroxy-3-methylbutyl]-3-phenylcyclopropenone (compd. No. 478 in Table 2)

mp: 128°–130° C. IR(KBr, cm$^{-1}$): 3297, 1856, 1703, 1649, 1615 NMR(CDCl$_3$, δ): 0.69(d, J=6.0 Hz, 3H), 0.74(d, J=5.8 Hz, 3H), 1.02(d, J=6.5 Hz, 3H), 1.09(d, J=6.5 Hz, 3H), 1.25–1.50(m, 3H), 2.42(m, 1H), 2.95–3.10(m, 2H), 3.49(m, 1H), 4.33–4.53(m, 2H), 4.95–5.15(m, 3H), 5.35(m, 1H), 6.25(d, J=8.9 Hz, 1H), 6.84(m, 1H), 7.08–7.19(m, 2H), 7.19–7.38(m, 8H), 7.40–7.60(m, 3H), 7.64(d, J=7.1 Hz, 1H), 7.96(dd, J=7.7 Hz, 1.7 Hz, 2H)

The following experiments were conducted to evaluate the biological activity of compound (I) prepared in the above Examples.

EXPERIMENT 1

Assay of Thiol Protease Inhibitory Activity

Inhibitory activity against papain (P-3125, Sigma) and cathepsin B (C-6286, Sigma) was assayed according to the method described in a literature [Biochemical Journal, 201, 189 (1982)]. Capthesin L was purified from rat kidney according to the method in a literature [Journal of Biochemistry, 100, 35 (1986)], and the inhibitory activity against it was assayed in the same manner as described in the above literature for cathepsin B. Further, m-calpain was purified from rat brain according to a known method [Journal of Biological Chemistry, 254, p.3210 (1984)] and the inhibitory activity against it was assayed by a method described in a literature [Journal of Biological Chemistry, 259, 12489 (1984)]. The results are shown in Tables 3 and 4. It is evident from Tables 3 and 4 that the compounds in the present invention have a potent inhibitory activity against thiol proteases such as papain, cathepsin B, cathepsin L,

TABLE 3

| Compd. of Ex. No. (Compd. No. in Table 1) | IC$_{50}$ (μM) | | | |
|---|---|---|---|---|
| | papain | cathepsin B | cathepsin L | m-calpain |
| 1 (No. 77) | 0.054 | 0.71 | 0.00086 | 1.6 |
| 2 (No. 77) | 22 | 0.044 | 0.0012 | 3.3 |
| 4 (No. 4) | 5.8 | 0.41 | — | 0.50 |
| 5 (No. 10) | >100 | 3.0 | 0.75 | 2.3 |
| 6 (No. 15) | 0.076 | 0.16 | 0.54 | 0.81 |

TABLE 3-continued

| Compd. of Ex. No. (Compd. No. in Table 1) | IC$_{50}$ ($\mu$M) | | | |
|---|---|---|---|---|
| | papain | cathepsin B | cathepsin L | m-calpain |
| 7 (No. 16) | 0.14 | 0.32 | 0.24 | 2.4 |
| 25 (No. 83) | 13 | 32 | 5.7 | 2.1 |
| 26 (No. 83) | 4.2 | 43 | 5.8 | 1.6 |
| 94 (No. 280) | 0.074 | 1.0 | 0.062 | 2.7 |
| 95 (No. 281) | 13 | 11 | 1.27 | 3.0 |
| 96 (No. 282) | 7.0 | 28 | 4.60 | 5.7 |
| 114 (No. 376) | 0.68 | 2.5 | 0.58 | 5.6 |
| 115 (No. 387) | 0.48 | 1.5 | 0.27 | 11 |

TABLE 4

(Inhibitory activity against m-calpain)

| Compd. of Ex. No. (Compd. No. in Table 1,2) | IC$_{50}$ ($\mu$M) |
|---|---|
| 9 (No. 26) | 5.0 |
| 20 (No. 72) | 1.3 |
| 21 (No. 72) | 3.0 |
| 29 (No. 97) | 1.7 |
| 31 (No. 99) | 1.3 |
| 32 (No. 99) | 1.2 |
| 33 (No. 102) | 0.84 |
| 37 (No. 114) | 2.1 |
| 38 (No. 120) | 4.0 |
| 39 (No. 124) | 1.9 |
| 40 (No. 129) | 2.6 |
| 41 (No. 132) | 1.4 |
| 42 (No. 133) | 1.5 |
| 43 (No. 134) | 1.7 |
| 44 (No. 137) | 3.0 |
| 45 (No. 140) | 1.0 |
| 48 (No. 148) | 0.63 |
| 50 (No. 152) | 1.2 |
| 51 (No. 154) | 0.75 |
| 52 (No. 155) | 0.74 |
| 53 (No. 161) | 2.3 |
| 54 (No. 166) | 1.1 |
| 55 (No. 167) | 0.80 |
| 56 (No. 168) | 2.2 |
| 57 (No. 170) | 3.1 |
| 59 (No. 175) | 1.6 |
| 60 (No. 178) | 1.1 |
| 62 (No. 180) | 1.4 |
| 63 (No. 184) | 1.6 |
| 65 (No. 191) | 1.8 |
| 67 (No. 197) | 0.88 |
| 68 (No. 200) | 3.1 |
| 69 (No. 203) | 3.0 |
| 71 (No. 209) | 1.3 |
| 72 (No. 213) | 0.40 |
| 73 (No. 216) | 1.4 |
| 74 (No. 219) | 0.80 |
| 75 (No. 225) | 3.3 |
| 76 (No. 227) | 4.6 |
| 77 (No. 232) | 0.95 |
| 78 (No. 237) | 0.44 |
| 79 (No. 237) | 1.8 |
| 80 (No. 239) | 0.35 |
| 81 (No. 239) | 4.3 |
| 83 (No. 245) | 3.0 |
| 84 (No. 246) | 0.85 |
| 85 (No. 248) | 0.84 |
| 86 (No. 251) | 0.75 |
| 87 (No. 257) | 1.0 |
| 88 (No. 259) | 0.65 |

TABLE 4-continued (Inhibitory activity against m-calpain)

| Compd. of Ex. No. (Compd. No. in Table 1,2) | IC$_{50}$ ($\mu$M) |
|---|---|
| 89 (No. 260) | 0.46 |
| 91 (No. 265) | 1.9 |
| 105 (No. 311) | 1.5 |
| 111 (No. 317) | 2.9 |
| 112 (No. 319) | 4.3 |
| 118 (No. 467) | 0.84 |
| 120 (No. 478) | 1.2 |

EXPERIMENT 2

Acute toxicity

A suspension of the compound in the present invention in 0.5% CMC-Na aqueous solution was orally administered to SD female and male rats, and the rats were observed for 7 days. The LD$_{50}$ value of the compound (I) prepared in Example 1 is: >2,000 mg/kg.

The following formulation examples are illustrative only.

FORMULATION 1

(1) Tablet

The following ingredients were admixed in a conventional manner and compressed on customary tablet machine.

| | |
|---|---|
| Compound in Example 1 | 30 mg |
| Crystalline cellulose | 60 mg |
| Corn starch | 100 mg |
| Lactose | 200 mg |
| Magnesium stearate | 4 mg |

(2) Soft gelatin capsule

The following ingredients were admixed in a conventional manner and filled in soft capsules.

| | |
|---|---|
| Compound in Example 1 | 30 mg |
| Olive oil | 300 mg |
| Lecithin | 20 mg |

(3) Injection

The following ingredients were admixed in a conventional manner and filled in an ampoule in a volume of 1 ml.

| | |
|---|---|
| Compound in Example 29 | 2.5 mg |
| Sodium chloride | 3.5 mg |
| Distilled water for injection | 1 ml |

What we claim is:

1. 2-[(1S, 2S)-1-hydroxy-3-methyl-2-((S)-4-methyl-2-phenylsulfonylaminovalerylamino)butyl]-3-phenylcyclopropenone or a pharmaceutically acceptable salt thereof.

2. A pharmaceutical composition which comprises, as an active ingredient, a compound of claim 1 together with pharmaceutically acceptable carriers.

* * * * *